United States Patent [19]

Bauer et al.

[11] Patent Number: 5,772,992
[45] Date of Patent: Jun. 30, 1998

[54] COMPOSITIONS FOR CO-ADMINISTRATION OF INTERLEUKIN-3 MUTANTS AND OTHER CYTOKINES AND HEMATOPOIETIC FACTORS

[75] Inventors: S. Christopher Bauer, New Haven; Mark Allen Abrams; Sarah Ruth Braford-Goldberg, both of St. Louis; Maire Helena Caparon, Chesterfield; Alan Michael Easton, Maryland Heights; Barbara Kure Klein, St. Louis; John Patrick McKearn; Peter O. Olins, both of Glencoe; Kumnan Paik, Ballwin; John Warren Thomas, Town & Country, all of Mo.

[73] Assignee: G.D. Searle & Co., Chicago, Ill.

[21] Appl. No.: 191,973

[22] Filed: Feb. 4, 1994

Related U.S. Application Data

[63] Continuation-in-part of Ser. No. 411,796, Apr. 6, 1995, which is a continuation-in-part of Ser. No. 981,044, filed as PCT/US93/11198, Nov. 22, 1993, abandoned.

[51] Int. Cl.[6] .......................... A61K 38/20; A61K 38/19
[52] U.S. Cl. ..................... 424/85.2; 424/85.1; 435/69.52
[58] Field of Search ................................ 424/85.1, 85.2; 435/69.5, 69.52

[56] References Cited

U.S. PATENT DOCUMENTS

| | | |
|---|---|---|
| 4,438,032 | 3/1984 | Golde et al. . |
| 4,810,643 | 3/1989 | Souza . |
| 4,877,729 | 10/1989 | Clark et al. . |
| 4,959,455 | 9/1990 | Clark et al. . |
| 4,999,291 | 3/1991 | Souza . |
| 5,114,711 | 5/1992 | Bell et al. . |
| 5,218,092 | 6/1993 | Sasaki et al. . |

FOREIGN PATENT DOCUMENTS

| | | |
|---|---|---|
| 0 183 350 | 6/1986 | European Pat. Off. . |
| 0 337 359 | 10/1989 | European Pat. Off. . |
| 0413383 | 2/1991 | European Pat. Off. . |
| 4063595 | 2/1992 | Japan .................. C12N 15/00 |
| WO88/05469 | 7/1988 | WIPO . |
| 89/05824 | 6/1989 | WIPO ................. C07K 13/00 |
| WO90/01039 | 2/1990 | WIPO . |
| WO90/12877 | 11/1990 | WIPO . |
| WO91/07988 | 6/1991 | WIPO . |
| 93/07171 | 4/1993 | WIPO ................. C07K 13/00 |
| 94/12639 | 6/1994 | WIPO ................. C12N 15/24 |

OTHER PUBLICATIONS

Lokker, N.A.,et al. (1991) *EMBO J.* 8: 2125–31.
Lokker, N.A., et al. (1991) *J. Biol. Chem.* 266: 10624–31.
Olins, P.O. et al. (1995) J. Biol. Chem. 270: 23754–60.
Aglietta, M., et al., *Stem Cells Dayt* 2(83):83–7 (1993).
Appelbaum, F.R. *Cancer* 72(11 Suppl):3387–92 (1993).
Bodine, D.M.et al., *Blood* 78(4):914–20 (1991)
Brandt, J., et al. *Blood* 79(3):634–641 (1992).
Brandt, J.E., et al., *Blood* 83(6):1507–1514 (1994).
Briddell, R.A. et al., *Blood* 76(3):516–522 (1990).
Broxmeyer, H.E., et al. *J. Immun* 141:3852–3862 (1988).
Broxmeyer, H.E., et al. *Blood* 77(10):2142–2149 (1991).
Brugger, W., et al., *Blood* 81(10):2679–2584 (1993).
Bruno, E., et al., *Blood* 73 (3):671–677 (1989).
Bruno, E., et al., *Blood* 77(11):2339–2346 (1991).
Donahue, R.E., et al., *Science* 241:1820–1823 (1988).
Donahue, R.E., et al., *Annals N. Y. Acad. of Sci* 511:10–16 (1987).
Emerson, S.G., et al.,*J. Clin. Invest.* 82:1282–1287 (1988).
Farese, A.M., et al., *Blood* 82(10):3012–3018 (1993).
Ganser, A.,et al., *Blood* 79(10):2583–2591 (1992).
Gordon, M.S. et al., *Blood* 80(2):302–307 (1992).
Grosh, W.W. et al., *Clin Immunol Immunopathol* 62(1 Pt 2):s25–38 (1992).
Heyworth, C.M., et al., *Growth Factors* 2(2–3): 197–211 (1990).
Iscova, N.N., et al., *J. Immun* 142:2332–2337 (1989).
Ikebuchi, K., et al., *Proc. Natl. Acad. Sci. USA* 84:9035–9039 (1987).
Jacobsen, S.E.W.et al., *Blood* 80(3):678–687 (1992).
Jacobsen, F.W., et al., *Blood* 84(3):775–779 (1994).
Jacobsen, S.E.W., et al., *J. Exp. Med.* 181:1357–1363 (1995).
Kaushansky, K., et al., *Proc. Natl. Acad. Sci. USA* 92:3234–3238 (1995).
Kawano, Y., et al., *Blood* 77(10):2118–2121 (1991).
Kawano, Y., et al., *Stem Cells* 12:514–520 (1994).
Krumwieh, D., et al., *Int J Cell Cloning* 1(229):229–47 (1990).
Lopez, A.F., et al., *Proc. Natl. Acad. Sci. USA* 89:11842–11846 (1992).
Mayani, H., et al., *Blood* 81(12):3252–3258 (1993).
MacVittie, T.J., et al., *Blood* 84(8):2515–2522 (1994).
Metcalf, D. et al., *Blood* 79(11):2861–2866 (1992).
Metcalf, D. *Stem Cells Dayt* 2(1):1–11 (1993).
Metcalf, D. *Blood* 82(12):3515–3523 (1993).
Moore, M.A. *Cancer* 65(3 Suppl):836–44 (1990).
Moore, M.A. *Blood* 78(1):1–19 (1991).
Nand, S., et al., *Blood* 83(2):357–360 (1994).
Neidhart, J.A. *Cancer Supplement* 72(11):3381–3386 (1993).
Ogawa, M. *Blood* 81(11):2844–53 (1993).
Pietsch, T.,et al., *Blood* 80(5):1199–206 (1992).
Ploemacher, R.E., et al., *Leukemia* 7(9):1381–1388 (1993).
Rennick, D., et al., *Experimental Hematology* 22:136–141): (1994).
Robinson, B.E., et al.,*J. Clin. Invest.* 79:1648–1652 (1987).

(List continued on next page.)

Primary Examiner—David L. Fitzgerald
Attorney, Agent, or Firm—Dennis A. Bennett

[57] ABSTRACT

The invention provides compositions comprising a human interleukin-3 (hIL-3) variant or mutant protein (mutein) and another colony stimulating factor, cytokine, lymphokine, interleukin, or hematopoietic growth factor. The compositions are useful for the therapeutic co-administration of the proteins, as for example in hematopoietic reconstitution. factors or IL-3 variants.

23 Claims, 1 Drawing Sheet

OTHER PUBLICATIONS

Sekhsaria, S. et al., *Blood* 81(8):2152–2130 (1993).
Seiff, C.A., et al., *Blood* 73(3):688–693 (1989).
Smith, S.L., et al., *Exp. Hem.* 21(7):870–77 (1993).
Sonoda, Y., et al., *Proc. Natl. Acd. Sci. USA* 85:4360–4364 (1988).
Stahl, C.P., et al., *Blood* 80(10):1479–2485 (1992).
Sutherland, H.J., et al., *Blood* 81(6):1465–1470 (1993).
Takaue, Y., et al., *Blood* 76(2):330–5 (1990).
Tsuji, K., et al., *Blood* 79(11):2855–60 (1992).
Warren, D.J. et al., *J. of Immunology* 140:94–99 (1988).
S.S. Fojo et al, Biochem., vol. 17, No. 15, 3109–3115.

```
    1                           5                              10
ATG GCT CCA ATG ACT CAG ACT ACT TCT CTT AAG ACT TCT
Met Ala Pro Met Thr Gln Thr Thr Ser Leu Lys Thr Ser 15                       20                      25
TGG GTT AAC TGC TCT AAC ATG ATC GAT GAA ATT ATA ACA
Trp Val Asn Cys Ser Asn Met Ile Asp Glu Ile Ile Thr 30                   35
CAC TTA AAG CAG CCA CCT TTG CCT TTG CTG GAC TTC AAC
His Leu Lys Gln Pro Pro Leu Pro Leu Leu Asp Phe Asn 40                      45                      50
AAC CTC AAT GGG GAA GAC CAA GAC ATT CTG ATG GAA AAT
Asn Leu Asn Gly Glu Asp Gln Asp Ile Leu Met Glu Asn 55                       60
AAC CTT CGA AGG CCA AAC CTG GAG GCA TTC AAC AGG GCT
Asn Leu Arg Arg Pro Asn Leu Glu Ala Phe Asn Arg Ala 65                      70                      75
GTC AAG AGT TTA CAG AAT GCA TCA GCA ATT GAG AGC ATT
Val Lys Ser Leu Gln Asn Ala Ser Ala Ile Glu Ser Ile 80                       85                      90
CTT AAA AAT CTC CTG CCA TGT CTG CCC CTG GCC ACG GCC
Leu Lys Asn Leu Leu Pro Cys Leu Pro Leu Ala Thr Ala 95                   100
GCA CCC ACG CGA CAT CCA ATC CAT ATC AAG GAC GGT GAC
Ala Pro Thr Arg His Pro Ile His Ile Lys Asp Gly Asp 105                      110                     115
TGG AAT GAA TTC CGT CGT AAA CTG ACC TTC TAT CTG AAA
Trp Asn Glu Phe Arg Arg Lys Leu Thr Phe Tyr Leu Lys 120                  125
ACC TTG GAG AAC GCG CAG GCT CAA CAG ACC ACT CTG TCG
Thr Leu Glu Asn Ala Gln Ala Gln Gln Thr Thr Leu Ser

130
CTA GCG ATC TTT TAA TAA     [SEQ ID NO:10]
Leu Ala Ile Phe END END     [SEQ ID NO:9]
```

Fig-1

COMPOSITIONS FOR CO-ADMINISTRATION OF INTERLEUKIN-3 MUTANTS AND OTHER CYTOKINES AND HEMATOPOIETIC FACTORS

This is a continuation-in-part of allowed U.S. Ser. No. 08/411,796, filed Apr. 6, 1995, as international application PCT/U.S. 93/11198 and in the national stage under 35 U.S.C. §371 on Nov. 22, 1993 filed Nov. 24, 1992 which is now abandon.

FIELD OF THE INVENTION

The present invention relates to the coadministration or sequential treatment using mutants or variants of human interieukin-3 (hIL-3) and other colony stimulating factors (CSFs), cytokines, lymphokines, interleukins, hematopoietic growth factors or IL-3 variants.

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixedSerythroid colonies (when erythropoietin is also added).

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to tnerapeutic treatments such as radiation and chemotherapy.

Interleukin-3 (IL-3) is a hema copoietic growth factor which has the property oL being able Lc promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 126:2184 (1981) as a factor which induced expression of a T cell associated enzyme, 20-hydroxsteroid dehydrogenase. The factor was purified to homogeneity and shown to regulate the growth and differentiation of numerous subclasses of early hematopoietic and lymphoid progenitor cells.

In 1984, CDNA clones coding for murine IL-3 were isolated (Fung, et al., NATURE 307:233 (1984) and Yokota, et al., PROC. NATL. ACAD. SCI. USA 81:1070 (1984)). The murine DNA sequence coded for a polypeptide of 166 amino acids including a putative signal peptide.

The gibbon IL-3 sequence was obtained using a gibbon CDNA expression library. The gibbon IL-3 sequence was then used as a probe against a human genomic librar s to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two ailelic forms of hIL-3.

Dorssers, et al., GENE 55:115 (1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. No. 4,877,729 and U.S. Pat. No. 4,959,454 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231:134 (1986) performed a functional analysis of murine IL-3 analogues synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $CysI^{140}$ →$Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. I TATL. aCAD. SCI. USA 85:7897 (1988)

International Patent Application (PCT) WO 88/00598 discloses gibbon- and human-like IL-3. The hIL-3 contains a $Ser^8$ →$Pro^8$ replacement. Suggestions are ade to replace Cys by Ser, thereby breaking the disulfide bridge, and to replace one or more amino acids at the glycosylation sires.

EP-A-0275598 (WO 88/04691) illustrates that Alal can be deleted while retaining biological activity. Some mutant hIL-3 sequences are provided, e.g., two double mutants,$Ala^1$ →$Asp^1$, $Trp^{13}$ →$ArgI^{13}$ (pGB/IL-302) and $Ala^1$ →$Asp^1$, $Met^3$ →$Thr^3$ (pGB/IL-304) and one triple mutant $Ala^1$ →$Asp^1$, $Leu^9$ →$Pro^9$, $Trp^{13}$ →$Arg^{13}$ (pGB/IL-303).

Wo 88/05469 describes how deglycosylation mutants can be obtained and suggests mutants of $Arg^{54}Arg^{55}$ and $Arg^{108}Arg^{109}Lys^{110}$ might avoid proteolysis upon expression in *Saccharomvces cerevisiae* by KEX2 protease. No mutated proteins are disclosed. Glycosylation and the KEX2 protease activity are only important, in this context, upon expression in yeast.

Wo 88/06161 mentions various mutants which theoretically may be conformationally and antigenically neutral. The only actually performed mutations are $Met^2$ →$Ile^2$ and $Ile^{131}$ →$Leu^{131}$. It is not disclosed whether the contemplated neutralities were obtained for these two mutations.

Wo 91/00350 discloses nonglycosylated hIL-3 analog proteins, for example, hIL-3 (Pro$^8$Asp$^{15}$Asp$^{70}$), Met$^3$ rhuI-3 (Pro$^8$Asp$^{15}$Asp$^{70}$); Thr$^4$ rhuL-3 (Pro8Aspl5Asp$^{70}$)and Thr$^6$ rhuIL-3 (Pro$^8$Asp$^{15}$Asp$^{70}$). It is said that these protein compositions do not exhibit certain adverse side effects associated with native hIL-3 such as urticaria resulting from infiltration of mast cells and lymphocytes into the dermis. The disclosed analog hIL-3 proteins may have N termini at Met$^3$, Thr$^4$, or Thr$^6$.

We 91/12874 discloses cysteine added variants (CAVs) of IL-3 which have at least one Cys residue substituted for a naturally occurring amino acid residue.

U.S. Pat. No. 4,810,643 discloses the DNA sequence encoding human G-CSF.

WO 91/07988 discloses a method to increase megakaryocyte production comprised of administration of G-CSF with IL-3 or GM-CSF. Also disclosed is a method for increasing platelet production comprised of administration of IL-6 with IL-3, G-CSF or GM-CSF.

SUMMARY OF THE INVENTION

The present invention encompasses recombinant human interleukin-3 (hIL-3) variant or mutant proteins (muteins) These hIL-3 muteins contain one to three amino acid substitutions and may also have amino acid deletions at either/ or both the N- and C- termini. This invention encompasses coadministration or sequential treatment using IL-3 variants of the present invention with other colony stimulating factors (CSFs), cytokines, lymphokines, interleukins, hematopoietic growth factors (herein after collectively referred to as "colony stimulating factors") which may have the potential for therapeutic use in restoring hematopoietic cells to normal amounts in those cases where the number of cells has been reduced due to diseases or to therapeutic treatments such as radiation and/or chemotherapy. Coadministration or sequential treatment using IL-3 variants of the present invention with other colony stimulating factors may enhance therapeutic value due to the synergistic effects of the proteins that make up the treatment. The use o f multiple factors may also have the potential advantage by lowering the demands placed on factor-producing cells and their induction systems. If there are limitations in the ability of a cell to produce a factor then by lowering the required concentrations of each of the factors by using them in combination may usefully reduce demands on the factor-producing cells. The use of multiple factors may lower the amount of the factors that would be needed, probably reducing the likelihood of adverse responses.

Coadministration or sequentiaL treatment may have the usua L activit v c f the peptides forming the mixture or it ma y be furthe characterized by having a bioloaicaL or physiological activity greater than simply the additive function of the presence of IL-3 or the other growth factor alone. Coadmiristration or sequential treatment may also unexpectedly provide an enhanced effect on the activity or an activity different from that expected by the presence of IL-3 or the other colony stimulating factors, The IL-3 variants of the present invention may also have an improved activity profile which may include reduction of undesirable biological activities associated with native hIL-3.

The present invention includes mutants of hIL-3 in which from 1 to 14 amino acids have been deleted from the N-terminus and/or from 1 to 15 amino acids have been deleted from the C-terminus, containing one to three amino acid substitutions, which are used with other colony stimulating factors or IL-3 variant Preferred IL-3 variants of the present invention include variants in which amino acids 1 to 14 have been deleted from the N-terminus, amino acids 126 to 133 have been deleted from the C-terminus and contain from one to three amino acid substitutions in the polypeptide sequence.

The present invention also provides IL-3 variants which may function as IL-3 antagonists or as discrete antigenic fragments for the production of antibodies useful in immunoassay and immunotherapy protocols. Antagonists of hIL-3 would be particularly useful in blocking the growth of certain cancer cells like AML, CML and certain types of B lymphoid cancers. Other conditions where antagonists would be useful include those in which certain blood cells are produced at abnormally high numbers or are being activated by endogenous ligands. Antagonists would effectively compete for ligands, presumably naturally occurring hemopoietins including and not limited to IL-3, GM-CSF and IL-5, which might trigger or augment the growth of cancer cells b ar virtue of their abilit t bind to the receptor complex while intrinsic activation properties of the ligand are diminished. IL-3, GM-CSF and/or IL-5 also play a role in certain asthmatic responses. An antagonist of the IL-3 receptor may have the utility in this disease by blocking receptor-mediated activation and recruitment of inflammatory cells.

In addition to the use of the IL-3 variants of the present invention with other colony stimulating factors in vivo, it is envisioned that in vitro uses would include the ability to stimulate bone marrow and blood cell activation and growth before infusion into patients.

BRIEF DESCRIPTION OF THE DRAWINGS

FIG. 1 is the human IL-3 gene for *E. coli* expression (pMON5873), encoding the polypeptide sequence of natural (wild type) human IL-3 [SEQ ID NO:9], plus an initiator methionine, as expressed in *E. coli*, with the amino acids numbered from the N-terminus of the natural hIL-3.

DETAILED DESCRIPTION OF THE INVENTION

The present invention encompasses the coadministration or sequential treatment with recombinant human interleukin-3 (hIL-3) variant or mutant proteins (muteins) with other colony stimulating factors (CSFs), cytokines, lymphokines, interleukins, hematopoietic growth factors and variants thereof (herein after collectively referred to as "colony stimulating factors)". This invention encompasses the coadministration or sequential treatment using IL-3 variants and other colony stimulating factors colony stimulating factors, each of which may act through a different and specific cell receptor to initiate complementar y biological activities.

Hematopoiesis requires a complex series of cellular events in which stem cells generate continuously into large populations of maturing cells in all major lineages. There are currently at least 20 Known egulators with hematopoietic proliferative activity. ost of these proliferative regulators can stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf, 1989). Other mechanism could explain synergy. For example, if one signalling pathway is limited by an intermediate activation of an additional signalling pathway by a second factor may result in a superadditive response. In some cases, activation of one receptor type can induce an enhanced expression of other receptors (Metcalf, 1993). Two or more factors may result in a different pattern of cell lineages then from a single factor. The use of the IL-3 variants of -he uresent invention with other colony stimulating factors may have the potential clinical advantage resultin fror a proliferative resoonse that is not possible by any single factor. Hematopoietic and other growth factors can be grouped in to two distinct families of related receptors: (1) tyrosine kinase receptors, including those for epidermal growth factor, M-CSF (Sherr, 1990) and SCF (Yarden et al., 1987): and (2) hematopoietic receptors, not containing a tyrosine kinase domain, but exhibiting obvious homology in their extracellular domain (Bazan, 1990). Included in the later group areSerythropoietin (D'Andrea et al., 1989), GM-CSF (Gearing et al., 1989), IL-3 (Kitamura et al., 1991), G-CSF (Fukunaga et al., 1990), IL-4 (Harada et al., 1990), IL-5 (Takaki et al., 1990), IL-6 (Yamasaki et al., 1988), IL-7 (Goodwin et al., 1990), LIF (Gearing et al., 1991) and IL-2 (Cosman et al., 1987). Most of the later group of receptors exists in high-affinity form as a heterodimers. After ligand binding, the specific α-chains become associated with at least one other receptor chain (β-chain, γ-chain). Many of these factors share a common receptor subunit. The α-chains for GM-CSF, IL-3 and IL-5 share the same β-chain (Miyajima et al., 1992) and receptor complexes for IL-6, LIF and IL-11 share a common β-chain (gp130) (Taga et al., 1989; Taga et al., 1992; Gearing et al., 1992). The receptor complexs of IL-2, IL-4 and IL-7 share a common γ-chain (Motonari et al., 1993; Russell et al., 1993; Masayuki et al., 1993).

GM-CSF accelerates recovery of neutrophils and maintains functional capacity, yet has little demonstrable effect on platelet recovery. In contrast IL-3 promotes a slower increase recovery in neutrophils and monocytes while accelerating the recovery of platelets.

Recenr studies in normal primates indicate that when IL-3 was admin istered before GM-CSF that the combination of IL-3 and GM-CSF promoted a synergistic rise in peripheral white blood cells and platelets (Donahue R. R. et al., 198 8; Krumwileh . et al., 1988; and Stahl C.P. et al., 1992). The synergistic effect observed in the sequential combination of IL-3 before GM-CSF may result from the expansion of GM-CSF sensitive cells by IL-3 resulting in a more efficien production of neutrophils. The coadministration of GM-CSF and IL-3 resulted in diminished neutrophils production relative to GM-CSF alone (Farese et al., 1993). The coadministration of IL-3 and GM-CSF, may result in down regulation of GM-CSF receptors by IL-3 thereby dampening the GM-CSF induced increase in neutrophils. However the coadministration of IL-3 and GM-CSF in a marrow-ablated rhesus monkeys promoted accelerated platelets and neutrophil recovery relative to sequential cytokine treatment or with either IL-3 or GM-CSF alone (Farese et al., 1993).

The in vitro activity of both IL-3 and GM-CSF has been shown to be additive with respect to stimulating larger colonies than either cytokine alone (Robinson et al., 1987; Bruno et al., 1989; Metcalf et al., 1992; Bruno et al., 1991; Bridell et al., 1990). Recently IL-12 has been shown to synergize with IL-3 and c-kit stem cell factor) to enhance the recovery of hemopoietic stem cells in liquid culture (Ploemacher et al., 1993).

Recent in vitro (Emerson et al., 1988: Sonodo et al., 1988) and in vivo (Ganser et al., 1992; Donahue R. E. et al., 1988; Krumwieh D. et al., 1988; and Stahl C.P. et al., 1992) results of combined IL-3 and GM-CSF treatment suggests an increased clinical efficacy in cytokine combination treatment.

As mentioned earlier some of the factors that are involyed in hematopoiesis are limited to a specific cell lineage and others have much broader effect and may result in the proliferation and support of multi-lineages and there may be considerable overlap between these factors but that the proliferative profiles are distinct. This suggests that the coadministration or sequential treatment with multiple factors may have a clinical advantage. IL-3 variants of the present invention that have an increased therapeutic index, compared to native IL-3, may have a distinct clinical advantage when coadministered or used sequentially in treatment.

The use of multiple factors may also have potential advantage by lowering the demands placed on factor-producing cells and their induction systems. If there are limitations in the ability of a cell to produce a factor then by lowering the required concentrations of each of the factors by using them in combination may usefully reduce demands on the factor-producing cells. The use of multiple factors may lower the amount of the factors that would be needed, probably reducing the likelihood of adverse responses.

A non-exclusive list of growth factors, colony stimulating factors (CSFs) include, cytokines, lymphokines, interleukins, and hematopoietic growth factors, which can be used in coadministration or sequential treatment with the hIL-3 variants of the present invention include GM-CSF, CSF-1, G-CSF, Meg-CSF, M-CSF,Serythropoietin (EPO), IL-I, IL-4, IL-2, IL-5, IL- 6, IL-7, IL-8, IL-9, IL-10, IL-11, IL-12, IL-13, LIF, flt3/flk2, human growth hormone, B-cell growth factor, B-cell differentiation factor, eosinophil differentiation factor and stem cell factor (SCF) also known as steel factor or c-kit ligand.

The present invention relates to novel variants of human interleukin-3 (hIL-3) in which amino acid substitutions have been made at one to three positions in amino acid se quence of the polypeptide used in sequential treatment or coadmiristration with other colony stimulating factors. Preferred IL-3 variants of the present invention which have deletions of amino acids 1 to 14 at the N-terminus and 126 to 133 at the C-terminus and which also have one to three amino acid substitutions in the polypeptlde used in coadministered or sequential treatment with other colony stimulating factors or IL-3 variants. The present invention includes mutant polypeptides comprising minimally amino acids 15 to 118 of hIL-3 with or without additional amino acid extensions to the N-terminus and/or C-terminus which further contain one to three amino acid substitutions in the amino acid sequence of the polypeptide.

As used herein human interleukin-3 corresponds to the amino acid sequence (1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "nvariant protein" or "mutein" means a protein comprising a mutant amino acid sequence and includes polype ptides which differ from the amino acid sequence of native hIL-3 due to amino acid deletions, substitutions, or both. "Native sequence" refers tc an amino acid or nuclec acid sequence which is identical to a wild-type or native form of a gene or protein.

Human IL-3 can be characterized by its ability to stimulate colonv formation by human hematopoietic progenitor cells. The colonies formed include erythroid, granulocyte, megakaryocvte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. (1990); Ganser, A, et al. (1990); Falk, S., et al. (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Many or all of these biological activities of hIL-3 involye signal transduction and high affinity receptor binding. Coadministration or sequential treatment using the IL-3 variants of the present invention with other colony stimulating factors may exhibit useful properties such as having similar or greater biological activity when compared to native hIL-3 or by having improved half-life or decreased adverse side effects, or a combination of these properties. The IL-3 variants of the present invention may also be useful as antagonists. IL-3 variants which have little or no activity when compared to native hIL-3 may still be useful as antagonists, as antigens for the production of antibodies for use in immunology or immunotherapy, as genetic probes or as intermediates used to construct other useful hIL-3 muteins.

The use of IL-3 variants of the present invention when coadministered or as part of sequential treatment will preferably have at least one biological property of human IL-3. Coa dminis-ration or sequential treatment mav also have more than one IL-3-like biological prooertv, or an improved property, or a reduction in an undesirable biological property of human IL-3. Some mutant polypeptides of the present invention may also exhibit an improved side effect profile. For example, they may exhibit a decrease in leukotriene release or histamine release when compared to native hIL-3 or (15–125) hIL-3. Such hIL-3 or hIL-3-like biological properties may include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3-like biological property is the stimulation of granulocytic type colonies, megakaryocytic type colonies, monocyte/macrophage type colonies, andSerythroid bursts. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Human IL-3 also has some biological activities which may in some cases be undesirable, for example the ability to stimulate leukotriene release and the ability to stimulate increased histamine synthesis in spleen and bone marrow cultures and in vivo.

Biological activity of hIL-3 and hIL-3 variant proteins of the present invention is determined by DNA synthesis by human acute myelogenous leukemia cells (AML). The factor-dependent ceil line S OIL 193 was adapted for use in testing biological activity. The biological actlyitv of h TL-3 and hIL-3 vartant proteins of the presernt invention is also determined by counting the colony forming units in a none marrow assay.

Other in vitro cell based assays may also be useful to determine the svnergistic effect of multiple colony stimulating factors that comprise the mixture. The following are examples of other useful assays.

TF-1 proliferation assay: The TF-1 cell line was derived from bone marrow of a patient with erythroleukemia (Kitamura et al., 1989). TF-1 cells respond to IL-3, GM-CSF, EPO and IL-5.

32D proliferation assay: 32D is a murine IL-3 dependent cell line which does not respond to human IL-3 but does respond to human G-CSF which is not species restricted. T1165 proliferation assay: T1165 cells are a IL-6 dependent murine cell line (Nordan et al., 1986) which respond to IL-6 and IL-11.

Human Plasma Clot meg-CSF Assay: Used to assay megakaryocyte colony formation activity (Mazur et al., 1981).

One object of the present invention is to provide hIL-3 variant with one to three amino acid substitutions in the polypeptide sequence used in coadministration or sequential treatment with other colony stimulating factors or IL-3 variants, which have similar or improved biological activity in relation to native hIL-3 or the other colony stimulating factors or IL-3 variant.

The hIL-3 variants of the present invention may have hIL-3 or hIL-3-like activity. For example, they may possess one or more of the biological activities of native hIL-3 and may be useful in stimulating the production of hematopoietic cells by human or primate progenitor cells. The IL-3 variants of the present invention and pharmaceutical compositions containing them may be useful in the treatment of conditions in which hematopoietic cell populations have been reduced or destroyed due to disease or to treatments such as radiation or chemotherapy. Pharmaceutical compositions containing IL-3 variants of the present invention can be administered parenterally, intravenously, or subcutaneously.

Native hIL-3 possesses considerable inflammatory activity and has been shown to stimulate synthesis of the arachidonic acid metabolites $LTC_4$, $LTD_4$, and $LTE_4$; histamine synthesis and histamine release. Human clinical trials with native hIL-3 have documented inflammatory responses (Biesma, et al., BLOOD, 80:1141–1148 (1992) and Postmus, et al., J. CLIN. ONCOL., 10:1131–1140 (1992)). A recent study indicates that leukotrienes were involved in IL-3 actions in vivo and may contribute significantly to the biological effects of IL-3 treatment (Denzlinger, C., et al., BLOOD, 81:2466–2470 (1993))

Some IL-3 variants of the present invention, when co-administered with other CSFs, cytokines, lymphokines, interleukins, hematopoietic growth factors or IL-3 variants, may have an improved therapeutic profile as compared to native hIL-3 or (15–125)hIL-3. For example, some IL-3 variants of the present invention may have a similar or more potent growth factor activity relative to native hIL-3 or (15–125)hIL-3 without having a similar or corresponding increase in the stimulation of leukotriene or histamine. These IL-3 variants would be expected to have a more favorable therapeutic profile since the amount of polypeptide which needs to be given to achieve the desired growth factor activity (e.g. cell proliferation) would have a diminished leukotriene or histamine stimulating effect. In studies with native hIL-3, the stimulation of inflammatory factors has been an undesirable side effect of the treatment. Reduction or elimination of the stimulation of mediators ot inflammation would provide an advantage over the use of native h IL-3.

Novel IL-31 variants of the present invention may also be useful as anta gonists which block the hIL-3 receptor by binding specifically to it and preventing binding of the agonist.

One potential advantage of the novel IL-3 variants of the present invention, particularly those which retain activity similar to or better than that of native hL-3, is that it may be possible to use a smaller amount of the biologically active mutein to produce the desired therapeutic effect. This may make it possible to reduce the number of treatments necessary to produce the desired therapeutic effect. The use of smaller amounts may also reduce the possibility of any potential antigenic effects or other possible undesirable side effects. For example, if a desired therapeutic effect can be achieved with a smaller amount of polypeptide it may be possible to reduce or eliminate side effects associated with the administration of native IL-3 such as the stimulation of leukotriene and/or histamine release. The novel IL-3 variants of the present invention may also be useful in the activation of stem cells or progenitors which have low receptor numbers.

Compounds of this invention are preferably made by genetic engineering techniques now standard in the art U.S. Pat. No. 4,935,233 and Sambrook et al., "Molecular Cloning. A Laboratory Manual", Cold Spring Harbor Laboratory (1989). One method of creating the preferred hIL-3 (15–125) mutant genes is cassette mutagenesis [Wells, et al. (1985)] in which a portion of the coding sequence c f hIL-3 in a plasmid is replaced with synthetic oligorucleotides that encode the desired amino acid substitutions in a portion of the gene between two restriction sites. In a similar manner amino acid substitutions could be made In the full-length hIL-3 gene, or genes encoding variants of hIL-3 in which from 1 to 14, amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed directed mutagenesis [Zoller and Smith (1982, 1983, 1984), Smith (1985), Kunkel (1985), Taylor, et al. (1985), Deng and Nickoloff (1992)] or polymerase chain reaction (PCR) techniques [Saiki, (1985)].

Plasmid DNA can be treated with the chosen restriction endonucleases then ligated to the annealed oligonucleotides. The ligated mixtures can be used to transform competent JMl101 cells to resistance to an appropriate antibiotic. Single colonies can be picked and the plasmid DNA examined by restriction analysis and/or DNA sequencing to identify plasmids with mutant hIL-3 genes.

Suitable cells or cell lines for the production of the proteins claimed in the present invention mav be bacterial cells. For example, the various strains of E. coli are well-known as host cells in the field of biotechnology. Examples of such strains include E. coli strains JMl101 [Yanish-Perron, et al. (1985)]and MON 105 [Obukowicz, et al. (1992)]. Also included in the present invention is the expression of the IL-3 variant protein utilizing a chromosomal expression vector for E. coli based on the bacterio phage Mu (Weinberg et al., 1993). Various strains of B. subtilis may also be employed as host cells for expression of the polypeptides of the present invention. Manv strains of yeast cells known Go those skilled in the art are also available as host cells for expression of the polypeptides of the present invention. When expressed in the E. coli cytoplasm, the above-men-ioned mutant hIL-3 variants of the present invention may also be construct with Met-Ala at the N-terminus so that upon expression te Met is a cleaved off leaving Ala at the N-terminus. The IL-3 variant proteins of the present invention may include polypeptides havinq Met-, Ala- or Met-Ala- attached to the N-terminus. When the IL-3 variant polypeptides are expressed in the cytoplasm of E. coli, polypeptides with and without Met attached to the N-terminus are obtained. The N-termini of proteins made in the cytoplasm of E. coli are affected by posttranslational processing by methionine aminopeptidase (Ben-Bassat et al., 1987) and possibly by other peptidases. These IL-3 variant proteins may also be expressed in E. coli by fusing a signal peptide to the N-terminus. This signal peptide is cleaved from the polypeptide as part of the secretion process. Secretion in E. coli can be used to obtain the correct amino acid at the N-terminus (e.g., $Asn^{15}$ in the (15–125) hIL-3 polypeptide) due to the precise nature of the signal peptidase. This is in contrast to the heterogeneity which may be observed at the N-terminus of proteins expressed in the cytoplasm in E. coli.

Also suitable for use in the present invention are mammalian cells, such as Chinese hamster ovary cells (CHO). General methods for expression of foreign genes in mammalian cells are reviewed in: Kaufman, R. J. (1987) High level production of proteins in mammalian cells, in Genetic Enoineerin Q, Principles and Methods, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally fused to the coding region for the IL-3 variant. For example, plasmids such as pcDNA I/Neo, pRcl/RSV, and pRc/CMV (obtained from Invitrogen Corp., San Die go, Calif. can be used. The eukaryotic secretion signal peptide coding region can be from the hIL-3 gene Itself or it can be from another secreted mammalian protein (Bayne, M. L. et al. (1987) Pro, Natl. Acad. Sci. USA 84, 2638–2642). After construction of the vector containing the hIL-3 variant gene, the vector DNA is transfected into mammalian cells. Such cells can be, for example, the COS7, HeLa, BHK, CHO, or mouse L lines. The cells can be cultured, for exam ple, in DMEM media (JRH Scientific). The hIL-3 variant secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.* , 5(7) :1750–1759 (1985) or Howley et al., U.S. Pat. No. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, *Genetic Engineering*, 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus oromoter (such as the polyhedron promoter drives transcription of a eukarvotic secretion signal peptide coding region, which is translat ionally fused t ic the coding region for the IL-3 variant polypectide. For example, the plasm id pVL1392 (obtained from Invitrogen Corp., San Diego, Calif.) can be used. After construction of the vector carrying the gene encooina the IL-3 variant polypeptide, two micrograms of this DNA is cotransfected with one microgram of Baculovirus DNA (see Summers & Smith, 1987) into insect cells, strain SF9. Pure recombinant Baculovirus carrying the IL-3 variant gene is used to infect cells cultured, for example, in Excell 401 serum-free medium (JRH Biosciences, Lenexa, Kansas). The IL-3 variant protein secreted into the medium can be recovered by standard biochemical approaches. Supernatants from mammalian or insect cells expressing the IL-3 variant protein can be first concentrated using any of an number of commercial concentration units.

Coadministration or sequential treatment using IL-3 variants of the present invention with other colony stimulating factors may be useful in the treatment of diseases characterized by a decreased levels of either myeloid,Serythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage. Therapeutic treatment of leukopenia with these IL-3 variants of the present invention with other colony stimulating factors may avoid undesirable side effects caused by treatment with presently available drugs.

Coadministered or sequential treatment using IL-3 variants of the present invention with other colony stimulatino factors may be useful in the treatment of neutropenia and, for example, in the treatment of such conditions as aplastic anemia, cyclic neutropenia, idiopathic neutropenia, Chediak-Higashi syndrome, systemic lupusSerythematosus (SLE), leukemia, myelodysplastic syndrome and myeiofibrosis. The IL-3 variants of the present invention, when coadministered or used in sequential treatment, may be useful in the treatment or prevention of thrombocytopenia.

Currently the only therapy for thrombocytopenia is platelet transfusions which are costly and carry the significant risks of infection (HIV, HBV) and alloimunization. The IL-3 variants, when coadministered or used in sequential treatment, may alleviate or diminish the need for platelet transfusions. Severe thrombocytopenia may result from genetic defects such as Fanconi's Anemia, Wiscott-Aldrich, or May-Hegglin syndromes. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valyes may result in thrombocytopenia. Severe thrombocytopenia may also result from chemotherapy and/or radiation therapy or cancer. Thrombocytopenia may also result from marrow invasion b y carcinoma, lymphoma, leukemia or fibrosis.

The IL-3 variants of the present invention, when coadministered or used in sequential treatment, may be useful in the mobilization of hematopoietlc progenitors and stem cells into peripheral blood. Peripheral blood derived progenitors have been shown to be effective in reconstituting patients in the setting of autologous marrow transplantation. Hematopoietic growth factors includin g G-CSF and GM-CSF have been shown to enhance the number of circulating progenitors and stem cells in the peripheral blood. This has simplified the procedure for peripheral stem cell collection and dramatically decreased the cost of the procedure by decreasing the number of pheresis required. The IL-3 variants, when coadministered or used in sequential treatment, may be useful in mobilization of stem cells and further enhance the efficacy of peripheral stem cell transplantation.

Another projected clinical use of growth factors has been in the in vitro activation of hematopoietic progenitors and stem cells for gene therapy. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenytoin or carbamazepine, antithyroids such as propylthiouracil and methimazole and diuretics. Coadministration or sequential treatment using IL-3 variants of the present invention with other colony stimulating factors may be useful in preventing or treating the bone marrow suppression or hematopoietic deficiencies which often occur in patients treated with these drugs.

Hematopoietic deficiencies may also occur as a result of viral, microbial or parasitic infections an d as a result o f treatment for renal disease or renal failure, e.g., dialysis. Coadministration or sequential treatment using IL-3 variants of the present invention with other colony stimulating factors may be useful in treating such hematopoietic deficiency.

The treatment of hematopoietic deficiency may include administration of a pharmaceutical composition containing the IL-3 variants with other colony stimulating factors to a patient. Coadministration or sequential treatment using IL-3 variants of the present invention with other colony stimulating factors may also be useful for the activation and amplification of hematopoietic precursor cells by treating these cells in vitro with the coadministration or sequential treatment using IL-3 variants of the present invention with other colony stimulating factors prior to injecting the cells into a patient.

Various immunodeficiencies e.g., in T and/or B lymphocytes, or immune disorders, e.g., rheumatoid arthritis, may also be beneficiall y affected by treatment with the coadministration or sequential treatment using IL-3 variants of the present invention with other colony stimulating factors molecules of the present invention. Immunodeficiencies may be the result of viral infections e.g. HTLVI, H mLVII, HTLVIII, severe exposure to radiation, cancer therapy or the result of other medical treatment. IL-3 variants of the present invention may also be employed, alone or in combination with other hematopoietins, in the treatment of other blood cell deficiencies, including thrombocytopenia (platelet deficiency), or anemia. Other uses for these novel polypeptides are in the treatment of patients recovering from bone marrow transplants in vivo and ex vivo, and in the development of monoclonal and polyclonal antibodies generated by standard methods for diagnost ic or therapeutic use.

Other aspects of the present invention are methods and therapeutic comoositions for treating the conditions referred to above. Such compositions comprise a therapeutically effective amount of one or more of the IL-3 variants of the present invention with otner colony stimulating factors in a mixture with a pharmaceutically acceptable carrier. This composition can be administered either parenterally, intravenously or subcutaneously. when administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.2–150 μg/kg of IL-3 variant protein per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given IL-3 variant protein vs. the activity of native (reference) IL-3 and it would not be unreasonable to note that dosage regimens may include doses as low as 0.1 microgram and as high as 1 milligram per kilogram of body weight per day. In addition, there may exist specific circumstances where dosages of IL-3 variant protein would be adjusted higher or lower than the range of 10–200 micrograms per kilogram of body weight. These include co-administration with other CSF, t ytokine, lymphokine, interleukin, hematopoietic growth factor or IL- 3 variant or growth factors; coadministration with chemotherapeutic drugs and/or radiation; the use of glycosylated IL-3 proteins; and various patient-related issues mentioned earlier in this section. A indicated above, the threaputic method and compositions may also include coadministration with other human factors. A non-exclusive list of other appropriate hema copoietins, CSFs, cytokines, lymphokines, hematopoietic growth factors and interleukins for simultaneous or serial coadministration with the polypeptides of the present invention includes GM-CSF, CSF-1, G-CSF, Meg-CSF, M-CSF, erythropoie cin (EPO,, IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count and the like.

The present invention includes the following compositions:

1. A composition comprising:
A human interleukin-3 mutant polypeptide of the Formula:

```
Ala Pro Met Thr Gln Thr Thr Ser Leu Lys Thr Ser Trp Val Asn
 1           5                    10                  15

Cys Xaa Xaa Xaa Xaa Xaa Xaa Xaa Xaa Xaa Xaa Xaa Xaa Xaa
                20              25              30

Xaa Xaa Xaa Xaa Xaa Xaa Xaa Xaa Asn Xaa Xaa Xaa Xaa Xaa
            35              40              45

Xaa Xaa Xaa Xaa Xaa Xaa Xaa Xaa Xaa Xaa Xaa Xaa Xaa Xaa
            50              55              60

Xaa Xaa Xaa Xaa Xaa Xaa Xaa Xaa Xaa Xaa Xaa Xaa Xaa Xaa
            65              70              75

Xaa Xaa Xaa Xaa Xaa Xaa Xaa Xaa Xaa Xaa Xaa Xaa Xaa Xaa
            80              85              90

Xaa Xaa Xaa Xaa Xaa Xaa Xaa Xaa Xaa Xaa Xaa Xaa Xaa Xaa
            95              100             105

Xaa Phe Xaa Xaa Xaa Xaa Xaa Xaa Xaa Xaa Xaa Xaa Xaa Xaa
            110             115             120

Xaa Xaa Xaa Gln Gln Thr Thr Leu Ser Leu Ala Ile Phe
            125             130
```

[SEQ ID NO:1]

wherein Xaa at position 2is Ser, Lys, Gly, Asp. Met, Gln, or Ar g;
 Xaa at positior 12 is Asn His, Leu, Ile, Phe, Ar g, or Gin;
 Xaa at position 19 is Met, Phe, Ile, Arg, Gly, Ala, or Cys;
Xaa at nosition 20 is Ile, Cys, Gly, Glu, Arg, Pro, or Ala ;
Xaa at position 21 is As, Ph- Lvs, Ar a Ala, Gly, Glu, Gln, Asr . Thr, Ser or Val;
Xaa at position 22 is Glu, Trp, Pro, Ser, Ala, His, Asp. Asn, Gln, Leu, Val or Gl y,;
Xaa at position 23 is Ile, Val, Ala, Leu, Gly, Trp, Lys, Phe, Leu, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp. Gln, Ser, Leu, or Lys;
Xaa at position 31 is Pro, Asp. Gly, Ala, Arg, Leu, or Gln;
Xaa at position 32 is Leu, Val, Ar a, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Val;
Xaa at position 36 is Asp. Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp. Ser, Cys, Asn, Lys, Thr, Leu, Val, Glu, Phe, Tyr, Ile, Met or Ala;
Xaa at position 43 is Glu, Asn, Tyr, Leu, Phe, Asp. Ala, Cys, Gln, Arg, Thr, Gly or Ser;
Xaa at position 44 is Asp, Sen, Leu, Arg, Lys, Thr, Met, Trp, Glu, Asn, Gln, Ala or Prc;
Xaa at position 4, is Gn-., Pro, Phe, Val, Met, Len, Thr,, Lys, Trp, Asp. Asn, Arc, Se :, Alu, Il-,u His;
Xaa at position 4 6 1S Asp. Phe, S2, Tr. - C . Glu, Asn, Gin,
Xaa at position 4 7 iS Il e, Si-, Val, Ser, Arg, PLo, or His;
Xaa at position 4-s Leu, Ser, Cys, Arg, Ile, His, Phe, Glu, Lys, Th-, Ala ; Met- V _ c a r Asn;
Xaa at position 49 is Met, Arg, Ala, Gly, Pro, Asn, His, or Asp;
Xaa at position 50 is Glu, Leu, Thr, Asp. Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp. !le, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp. Arg, Gln, Val, or Cys;
Xaa at position 59 is Glu Tyr, His, Leu, Pro, or Arg;
Xaa at position 60 is Ala, Ser, Pro, Tyr, Asn, or Thr;
Xaa at position 61 is Phe Asn, Glu, Pro, Lys, Arg, or Ser;
Xaa at position 62 is Asn His, Val, Arg, Pro, Thr, Asp. or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa an position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Vat, Trp, Ser, Ile, Phe, Thr, or His;
Xaa at position 69 is Sln, Ala, Pro, Thr, Slu, Arg, Trp, Gly, or Leu;
Xaa at position 70 is Asn, Le ., Val, T-p, Pr :c, or Ala;
Xaa at position 71 is Ala, Met, Leu, Pro, Ar a, Glu, Thr, Gln,
Xaa at position is la, Glu. Asn, Leu, Ser, G1-. - Th : C Arg;
Xaa at position 74 is Ile, Met, Thr, Pro, Arg, G -l, Ala;
Xaa at position 75 is Glu, Lys, Sly, Asp. Pro, Trp, Arg, Ser, Gln, or Leu;
Xaa at position 76 is Ser, Val, Ala, Asn, Trp, Glu, Pro, Sly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, GSu, or Arg;
Xaa at position 81 is Leu, Gln, Gly, Ala, Trp, Arg, Val, or Lys;
Xaa at position 82 is Leu, Sln, Lys, Trp, Arg, Asp. Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;

Xaa at position 86 is Pro, Cys, Arg, Ala, or Lys;
Xaa at position 87 is Leu, Ser, Trp, or Gly;
Xaa at position 88 is Ala, Lys, Arg, Val. or Trp;
Xaa at position 89 is Thr, Asp. Cys, Leu, Val, Glu, His, Asn, or Ser;
Xaa at position 90 is Ala, Pro, Se -, Thr, Gly, Asp. Ile, or Met;
Xaa at position 91 is Ala, Pro, Se -, Thr, Phe, Leu, Asp. or His;
Xaa at position 92 is Pro, Phe, Arg, Ser, Lys, His, Ala, Gly, Ile or Leu;
Xaa at position 93 Thr, Asp. Ser., Asn, Pro, Ala, Leu, or Arg;
Xaa at position 94 Arg, I , S G, Len, V . _, Slt, His, Ala, or Pro;
Xaa at position 9 3 His, Ser., R yt, Arg, va _, L - U , Sl . , hr, Asr., Lvs, Se - Al., Tit , Ph-, _ i-, Co T.
Xaa at position 96 is Pro, Lys, Tyr, Gly, Ile, cr Thr;
Xaa at position 97 is Ile, Val, Lys, Ala, or Asr.;
Xaa at position 98 is His, Ile, Asn, Leu, Asp. Ala, Thr, Glu, Gln, Ser, Phe, Met, Val, Lys, Arg, Tyr or Pro;
Xaa at position 99 is Ile, Leu, Arg, Asp. Val, Pro, Gln, Gly, Ser, Phe, or His;
Xaa at position 100 is Lys, Tyr, Leu, His, Arg, Ile, Ser, Gln, or Pro;
Xaa at position 101 is Asp. Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp. or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp. or His;
Xaa at position 106 is Glu, Ser, Ala, Lys, Thr, Ile, Gly, or Pro;
Xaa at position 108 is Arg, Lys, Asp. Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp. or Met;
Xaa at position 112 is Thr, Val, Gln, Tyr, Glu, His, Ser, or Phe;
Xaa at position 113 is Phe, Ser, Cys, His, Gly, Trp, Tyr, Asp. Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp. Val, Glu, Arg, Trp, Ser, Asn, His, Ala, Tyr, Phe, Gln, or Ile;
Xaa at position 117 is Thr, Ser, Asn, Ile, Trp, Lvs, or Pro;
Xaa at position 118 is Leu, Ser, Pro, Ala, Glu, Cys, Asp. or
Xaa at position 119 is Glu, Ser, Lys, Pro, Leu, Thr, Tyr, or Arg;
Xaa at position 120 is Asn, Ala, Pro, Leo, His, Val, of Glr;
Xaa at positior 121 is Ala, Ser, Ile, Asn, Pro, Lys, Asp. or Gly;
Xaa at position 122 is Gln, Ser, Met, Trip Arg, Phe, Pro, His, Ile, Tyr, or Cys;
Xaa at position 123 is Ala, Met, Glu, His, Ser, Pro, Tyr, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 1 to 3 of the amino acids designated by Xaa are different from the corresponding amino acids of native (1–133) human interleukin-3;

A colony stimulating factor selected from the group consisting of GM-CSF, CSF- L, G-CSF, Meg-CSF, M-CSF, Serythropoietin (EPO IL-1, IL-4, IL-2, IL-5, IL-6, IL-7, IL-8, IL-9, IL-10, IL-l1, IL-12, IL-13, LIF, flt3/flk2, human growth hormone, B-cell rowth factor, B-cell differentiation factor and eosinophil differentiation factor, stem cell factor (SCF); and At least one non-toxic pharmaceutically acceptable carrier.

Preferably the CSF is G-CSF or GM-GSF more preferably the CSF is G-CSF.

2. A composition, comprising:

A human interleukin-3 mutant polypeptide of the Formula:

Ala Pro Met Thr Gln Thr Thr Ser Leu Lys Thr Ser Trp Val Asn
1            5                    10                  15

Cys Xaa Xaa Xaa Ile  Xaa Glu Xaa Xaa Xaa Xaa Leu Lys Xaa Xaa
              20                   25                  30

Xaa Xaa Xaa Xaa Xaa Asp Xaa Xaa Asn Leu Asn Xaa Glu Xaa Xaa
              35                   40                  45

Xaa Ile  Leu Met Xaa Xaa Asn Leu Xaa Xaa Xaa Asn Leu Glu Xaa
              50                   55                  60

Phe Xaa Xaa Xaa Xaa Xaa Xaa Xaa Xaa Asn Xaa Xaa Xaa Ile  Glu
              65                   70                  75

Xaa Xaa Leu Xaa Xaa Leu Xaa Xaa Cys Xaa Pro Xaa Xaa Thr Ala
              80                   85                  90

Xaa Pro Xaa Arg Xaa Xaa Xaa Xaa Xaa Xaa Gly Asp Xaa Xaa
              95                   100                 105

Xaa Phe Xaa Xaa Lys Leu Xaa Phe Xaa Xaa Xaa Xaa Leu Glu Xaa
              110                  115                 120

Xaa Xaa Xaa Gln Gln Thr Thr Leu Ser Leu Ala Ile  Phe
              125                  130

[SEQ ID NO:2]

wherein
Xaa at position 17 is Ser, Gly, Asp. Met, or Gln;
Xaa at position 18 is Asn, His, or Ile;
Xaa at position 19 is Met or Ile;
Xaa at position 21 is As p or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Glr;
Xaa at position 31 is Pro, As , Gi- . , or Gln;
Xaa at position 32 is Leu, Arg, Gln, Asn, Gly, Ala, or Glu;
Xaa at position 33 is Pro or Glu;
Xaa at position 34 is Leu, Val, Ser, Lys, Ala, Arg, Gln Glu, Ile, Phe, Thr or Met;
Xaa at position 35 is Leu, Ala, Asn, Pro, Gin, or Val;
Xaa at position 37 is Phe; Ser, Pro, or Trp,
Xaa at position 38 is Asn or Ala;
Xaa at position 42 is Gly, Asp. Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp. Phe, Ser, Thr, Ala, Asn Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gin, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gin, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Slu, Pro, or Gly;
Xaa at position 77 is Ile or Leu;
Xaa at position 79 is Lys, Thr, Gly, Asn, Met, Ag, Ile, Gly, or Asp;
Xaa at position 80 is Asn, Gly, Glu, or Arg;
Xaa at position 82 is Leu, Gln, Trp, Arg, Asp. Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Tro;
Xaa at position 91 is Ala or Pro;
Xaa at position 93 is Thr, Asp. Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Leu, Arg, Gin, Leu, Lys, Met, Ser, Tyr, Val or Pro;
Xaa at position 99 is Ile, Leu, or Val;
Xaa at position 100 is Lys, Arg, Ile, Gin, Pro, or Ser;
Xaa at position 101 is Asp. Pro, Met, Lys, His, Thr, Pro, Asn, Ile, Leu or Tyr;
Xaa at position 104 is Trp or Leu;
Xaa at position 105 is Asn, Pro, Ala, Ser, Trp, Gin, Tyr, Leu, Lys, Ile, Asp. or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys, Thr, Val, Trp, Ser, Ala, His, Met, Phe, Tyr or Ile;
Xaa at position 117 is Thr or Ser;
Xaa at position 120 is Asn, Pro, Leu, His, Val, or Glin;
Xaa at position 121 is Ala, Ser, Ile, Asn, Pro, Asp. or Gly;
Xaa at position 122 is Gin, Ser, Met, Trp, Arg, Phe, Pro, His, Ile, Tyr, or Cys;
Xaa at position 123 is Ala, Met, Glu, His, Ser, Pro, Tyr, or Leu.

and which can additionally have Met- preceding the amino acid in position 1; and wherein from 1 to 14 amino acids can be deleted from the N-terminus and,or from 1 to 15 amino acids can be deleted from the C- cerminus; and wherein from 3 of the amino acids designated by Xaa are different from the corresponding amino acids of native (1–133) human interleukin-3;

A colony stimulating factor; and
At least one non- coxic pharmaceutically acceptable carrier.

3. The composition of 2, wherein said human interleukin-3 mutant polypeptide is of the Formula:

Ala Pro Met Thr Gln Thr Thr Ser Leu Lys Thr Ser Trp Val Asn
1               5                        10                    15

Cys Xaa Xaa Met Ile Asp Glu Xaa Ile Xaa Xaa Leu Lys Xaa Xaa
                20                      25                  30

Pro Xaa Pro Xaa Xaa Asp Phe Xaa Asn Leu Asn Xaa Glu Asp Xaa
              35                      40                    45

Xaa Ile Leu Met Xaa Xaa Asn Leu Arg Xaa Xaa Asn Leu Glu Ala
                50                      55                  60

Phe Xaa Arg Xaa Xaa Lys Xaa Xaa Xaa Asn Ala Ser Ala Ile Glu
                65                      70                  75

Xaa Xaa Leu Xaa Xaa Leu Xaa Pro Cys Leu Pro Xaa Xaa Thr Ala
                80                      85                  90

Xaa Pro Xaa Arg Xaa Pro Ile Xaa Xaa Xaa Xaa Gly Asp Trp Xaa
              95                      100                  105

Glu Phe Xaa Xaa Lys Leu Xaa Phe Tyr Leu Xaa Xaa Leu Glu Xaa
              110                     115                  120

Xaa Xaa Xaa Gln Gln Thr Thr Leu Ser Leu Ala Ile Phe
              125                     130

[SEQ ID NO:3]

where in
Xaa at position 17 is Ser, Gly, Asp. or Gln;
Xaa at position 18 is Asn, His, or Ile;
Xaa at position 23 is Ile, Ala, Leu, or Gly;
Xaa at position 25 is Thr, His, or Gln;
Xaa at position 26 is His or Ala;
Xaa at position 29 is Gln or Asn;
Xaa at position 30 is Pro or Gly;
Xaa at position 32 is Leu, Arg, Asn, or Ala;
Xaa at position 34 is Leu, Val, Ser, Ala, Arg, Gln, Glu, Ile, Phe, Thr, or Met;
Xaa at position 35 is Leu, Ala, Asn, or Pro;
Xaa at position 38 is Asn or Ala;
Xaa at position 42 is Gly, Asp. Ser, Ala, Asn, Ile, Leu, Met, Tyr or Arg;
Xaa at position 45 is Gln, Val, Met, Leu, Ala, Asn, Glu, or Lys;
Xaa at position 46 is Asp. Phe, Ser, Gln, Glu, His, Val or Thr;
Xaa at position 50 is Glu Asn, Ser or Asp;
Xaa at position 51 is Asn, Arg, Pro, Thr, or His;
Xaa at position 55 is Arg, Leu, or Gly;
Xaa at position 56 is Pro, Gly, Ser, Ala, Asr ., Val, Leu or Gln;
Xaa at position 62 is Asn, Pro, or Thr;
Xaa at position 64 is Ala or Asn;
Xaa at position 65 is Val or Thr;
Xaa at position 67 is Ser or Phe;
Xaa at position 68 is Leu or Phe;
Xaa at position 69 is Gin, Ala, Glu, or Ara;
Xaa at position 76 is Ser, Val, Asn, Pro, or Gly;
Xaa at position 77 is Ile or Leu;
Xaa at position 79 is Lys, Asn, Met, Ar c, Ile, or Gly,
Xaa at position 80 is Asn, Gly, Glu, or Arg;
Xaa at position 82 is Leu, Gln, Trp, Arg, Asp. Asn, Glu, His, Met, Phe, Ser, Thr, Try, or Val;
Xaa at position 87 is Leu or Ser;
Xaa at position 88 is Ala or Trp;
Xaa at position 91 is Ala or Pro;
Xaa at position 93 is Thr, Asp. or Ala;
Xaa at position 95 is His, Pro, Arg, Val, Gly, Asn, Ser or Thr;
Xaa at position 98 is His, Ile, Asn, Ala, Thr, Gln, Glu, Lys, Met, Ser, Tyr, Val or Leu;
Xaa at position 99 is Ile or Leu;

Xaa at position 100 is Lys or Arg;
Xaa at position 101 is Asp. Pro, Met, Lys, Thr, His, Pro, Asn, Ile, Leu or Tyr;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;
Xaa at position 116 is Lys, Val, Trp, Ala, His, Phe, Tyr or Ile;
Xaa at position 117 is Thr or Ser;
Xaa at position 120 is Asn, Pro, Leu, His, Val, or Gln;
Xaa at position 121 is Ala, Ser, Ile, Pro, or Asp;
Xaa at position 122 is Gln, Met, Trp, Phe, Pro, His, Ile, or Tyr;
Xaa at position 123 is Ala, Met, Glu, Ser, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 1 to 3 of the amino acids designated by Xaa are d irrereot from the corresponding amino acids of native (1–133) human interleukirt-3.

4. The composition of 3 wherein said human interleukin-3 mutant polypeptide is of the Formula:
Xaa at nosition 42 is Gly, Asp. Ser, Ile, Leu, Met, Tyr, or Ala;
Xaa at position 45 is Gln, Val, Met or Asn;
Xaa at position 46 is Asp. Ser, Gln, His or Val;
Xaa at position 50 is Glu or Asp;
Xaa at position 51 is Asn, Pro or Thr;
Xaa at position 62 is Asn or Pro;
Xaa at position 76 is Ser, or Pro;
Xaa at position 82 is Leu, Trp, Asp. Asn Glu, His, Phe, Ser or Tyr;
Xaa at position 95 is His, Arg, Thr, Asn or Ser;
Xaa at position 98 is His, Ile, Leu, Ala, Gln, Lys, Met, Ser, Tyr or Val;
Xaa at position 100 is Lys or Arg;
Xaa at position 101 is Asp. Pro, His, Asn, Ile or Leu;
Xaa at position 105 is Asn, or Pro;
Xaa at position 108 is Arg, Ala, or Ser;
Xaa at position 116 is Lys, Val, Trp, Ala, His, Phe, or Tyr;
Xaa at position 121 is Ala, or Ile;
Xaa at position 122 is Gln, or Ile; and
Xaa at position 123 is Ala, Met or Glu.

5. The composition, comprising:
A human interleukin-3 mutant polypeptide of the Formula:

Asn Cys Xaa Xaa Xaa Xaa Xaa Xaa Xaa Xaa Xaa Xaa Xaa Xaa Xaa
1               5                        10                    15

Xaa Xaa Xaa Xaa Xaa Xaa Xaa Xaa Asn Xaa Xaa Xaa Xaa Xaa
                20                      25                  30

Xaa Xaa Xaa Xaa Xaa Xaa Xaa Xaa Xaa Xaa Xaa Xaa Xaa Xaa Xaa
                35                      40                    45

Xaa Xaa Xaa Xaa Xaa Xaa Xaa Xaa Xaa Xaa Xaa Xaa Xaa Xaa Xaa
                50                      55                  60

Xaa Xaa Xaa Xaa Xaa Xaa Xaa Xaa Xaa Xaa Xaa Xaa Xaa Xaa Xaa
                65                      70                  75

Xaa Xaa Xaa Xaa Xaa Xaa Xaa Xaa Xaa Xaa Xaa Xaa Xaa Xaa Xaa
                80                      85                  90

Xaa Xaa Xaa Xaa Xaa Xaa Xaa Xaa Xaa Xaa Xaa Xaa Xaa Xaa Xaa
              95                      100                  105

Xaa Xaa Xaa Xaa Gln Gln  [SEQ ID NO:4]
              100 wherein
Xaa at position 3 is Ser, Lys, Gy, Asp. Met, Gin, or Arg;

Xaa at position 4 is Asn, His, Leu, Ile, Phe, Arg, or Gin;
Xaa at position 5 is Met, Phe, Ile, Arg, Gly, Ala, or Cys;
Xaa at position 6 is Ile, Cys, Gin, Glu, Arg, Pro, or Ala;
Xaa at position 7 is Asp. Phe, Lys, Arg, Ala, Gly, Glu, Gin, Asn, Thr, Ser or VaL;
Xaa at position 8 is Glu, Trp, Pro, Ser, Ala, His, Asp. Asn, Gin, Leu, Val, or Gly;
Xaa at position 9 is Ile, Val, Ala, Leu, G i y, Trp, Lys, Phe, Leu, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at positior 13 is Leu, Gly, Arg, Thr, or Ala;
Xaa at position 14 is Lys, Arg, Leu, Gln, Gly, Pro, Val or Trp;
Xaa at oosition 15 is Gln Asn, L ieu Pro, Arg, or Val;
Xaa at position 16 is Pro, His. Thr, Gly, Asp. Gin, Ser, Leu, or Lys;
Xaa at position 17 is Pro, Asp. Gly, Ala, Arg, Leu, or Gin;
Xaa at position 18 is Leu, Val, Arg, Gin, Asn, Gly, Ala, or Glu;
Xaa at position 19 is Pro, Leu, Gin, Ala, Thr, or Glu;
Xaa at position 20 is Leu, Val, GI,, Ser, Lys, Glu, Gin, Thr, Arg, Ala, Phe, Ile or Met;
Xaa at position 21 is Leu, Ala, Gly, Asn, Pro, Gin, or Val;
Xaa at position 22 is Asp. Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn i, Cys, Ar a, Leu, His, Met, Pro;
Xaa at position 28 is Gly, Asp. Set, Cys, Ala, Lys, Asn, Thr, Leu, Val, Glu, Phe, Tyr, Ile or Met;
Xaa at position 29 is Glu, Asn, Tyr, Leu, Phe, Asp. Ala, Cys, Gin, Arg, Thr, Gly or Ser;
Xaa at position 30 is Asp. Ser, Leu, Arg, Lys, Thr, Met, Trp, Glu, Asn, Gin, Ala or Pro;
Xaa at position 31 is Gin, Pro, Phe, Val, Met, Leu, Thr, Lys, Asp. Asn, Arg, Ser, Ala, Ile, Glu, His or Trp;
Xaa at position 32 is Asp. Phe, Ser, Thr, Cys, Glu, Asn, Gin, Lys, His, Ala, Tyr, Ile, Val or Gly;
Xaa at position 33 is Ile, Gly, Val, Ser, Arg, Pro, or His;
Xaa at position 34 is Lieu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at posiytion 36 is Glu, Leu, Thr, Asp. Tyr, Lys, Asn, Ser, Ala, Ile, Va,, His, Phe, Met or Gin;
Xaa at position 38 is Asn, His, Arg, Leu, Gly, Ser, or Thr;
Xaa at position 39 is Leu, ThL, Ala, Gly, Glu, Pro, Lys; Ser, Met, or;
Xaa at position 40 is Arg, Asp. Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp. Arg, Gln, Val, or Cys;
Xaa at position 45 is Glu Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp. or Ile;
Xaa at position 49 is Arg, Tyr, Trp, L ys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Ph e, Val, Gly, Asn, Ile, Pro, or His;
Xaa at position 54 is Leu, Val, Trp, Se, Ile, Phe, Thr, or His;

Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at oosition 58 is Ser, Glu, Met, Ala, His, Asn, Arg,
Xaa at position 59 is Ala, Glu, Asp. Leu, Ser, Gly, Thr, or Arg;
Xaa at position 60 is Ile, Met, Thr, Pro, Arg, Gly, Ala;
Xaa at position 6 1 is Glu, Lys, Gly, Asp. Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp. Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp. Cys, Leu, Val, Glu, His, Asn, or Ser;
Xaa at position 76 is Ala, Pro, Ser, Thr, Gl y, Asp. Ile, or Met;
Xaa at position 77 is Ala, Pro, Ser, Thr, Phe, Leu, Asp. or His;
Xaa at position 73 is Pro, Phe, Arg, Ser, Lys, His, Ala, Gly, Ile or Leu;
Xaa at position 79 is Thr, Asp. Ser, Asrn, Pro, Ala, Leu, or Arg;
Xaa at position 80 is Arg, Ile, Ser, Glu, Leu, Val, Cys, Lys, His, Ala or Pro;
Xaa at position 81 is His, Glu, Pro, Arg, Val, Leu, Gly, Thr, Asn, Lys, Ser, Ala, Trp, Phe, Ile, or Tyr;
Xaa at position 82 is Pro, Lys, Tyr, Gly, Ile, or Thr;
Xaa at position 83 is Ile, Val, Lys, Ala, or Asn;
Xaa at position 84 is His, Asn, Leu, Asp. Ala, Thr, Glu, Gln, Ser, Phe, Met, Val, Lys, Arg, Tyr, or Pro;
Xaa at position 85 is Ile, Leu, Arg, Asp. Val, Pro, Gln, Gly, Ser, Phe, or His;
Xaa at position 86 is Lys, Tyr, Leu, His, Arg, Ile, Ser, Gln, Pro;
Xaa at position 87 is Asp. Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp. or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp. or His;
Xaa at position 92 is Glu, Ser, Ala, Lys, Thr, Ile, Gly, or Pro;
Xaa at position 94 is Arg, Lys, Asp. Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp. or Met;
Xaa at position 98 is Thr, Val, Gln, Tyr, Glu, His, Ser, or Phe;

Xaa at position 99 is Phe, Ser, Cys, His, Gly, Trp, Tyr, Asp. Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at positior 102 is Lys, Leu, Pro, Thr, Met, Asn, Val, Glu, Arg, Trp, Ser, Asn, His, Ala, Tyr, Phe, Gln, or Ile;
Xaa at position 103 is Thr, Ser, sn, Ile, Trp, Lys, or Pro;
Xaa at position 104 is Leu, Ser, Pro, Ala, Glu, Cys, Asp. or Tvr;
Xaa at position 105 is Glu. Ser, Lys, Pro, Leu, Thr, Tyr, 5 or Ar a;
Xaa at position 10 6 iS Asn, Ala, Pro, Leu, His, Val, or Gin;
Xaa at position 10, is Ala, Ser, Ile, Asn, Pro, Lys, Asp. or Gly;
Xaa at position 108 is Gin, Ser, Met, Trp, Arg, Phe, Pro, His, Ile, Tyr, or Cys;
Xaa at position 109 is Ala, Met, Glu, His, Ser, Pro, Tyr, or Leu;
and which can additionally have Met- or Met-Ala- preceding the amino acid in position 1; and wherein from 1 to 3 of the amino acids designated by Xaa are different from the corresponding native amino acids of (1–133) human interleukin-3;

A colony stimulating factor; and

At least one non-toxic pharmaceutically acceptable carrier.

6. The composition of 5, wherein said human interleukin-3 mutant polypeptide is of the Formula:

Asn Cys Xaa Xaa Ile   Xaa Glu Xaa Xaa Xaa Xaa Leu Lys Xaa
  1           5                10                    15

Xaa Xaa Xaa Xaa Xaa Xaa Asp Xaa which can additionally have Met- or Me -Ala- preceding the amino acid in position 1; and wherein from 1 to 3 of the amino acids designated by Xaa are different from corresponmding amino acids of native human interleukin-3.

7. The composition of 6, wherein said human interleukin-3 munant polypeptide is of the FormuLa:

Asn Cys Xaa Xaa Met Ile  Asp Glu Xaa Ile  Xaa Xaa Leu Lys Xaa
1          5                10              15

Xaa Pro Xaa Pro  Xaa Xaa Asp Phe Xaa Asn Leu Ans Xaa Glu Asp
           20              25              30

Xaa Xaa Ile  Leu Met Xaa Xaa Asn Leu Arg Xaa Xaa Asn Leu Glu
              35              40              45

Ala Phe Xaa Arg Xaa Xaa Lys Xaa Xaa Xaa Asn Ala Ser  Ala Ile
              50              55              60

Glu Xaa Xaa Leu Xaa Xaa Leu Xaa Pro Cys Leu Pro Xaa Xaa Thr
              65              70              75

Ala Xaa Pro Xaa Arg Xaa Pro Ile  Xaa Xaa Xaa Xaa Gly Asp Trp
              80              85              90

Xaa Glu Phe Xaa Xaa Lys Leu Xaa Phe Tyr Leu Xaa Xaa Leu Glu
              95              100             105

Xaa Xaa Xaa Xaa Gln Gln [SEQ ID NO:6]
              110 wherein
Xaa at position 3 is Ser, Gly, Asdp, or Gln;
Xaa at position 4 is Asn, His, or Ile;
Xaa at position 9 is Ile, Ala, Len, or Gly;
Xaa at position 11 is Thr, His, or Gin;
Xaa at position 12 is His or Ala;
Xaa at position 15 is Gin or Asn;
Xaa at Dosition 16 is Pro or Gly;
Xaa at position 18 is Leu, Arg, Asn, or Ala;
Xaa at position 20 is Leu, Val, Ser, Ala, Arg, Gln, Glu, Ile, Phe, Thr, or Met;
Xaa an posItion 21 is Leu, Ala, Asn, or Pro;
Xaa at position 24is Asn or Ala;
Xaa at position 28 is Gly, Asp. Ser, Ala, Asn, Ile, Leu, Met, Tyr or Arg;
Xaa at position 31 is Gln, Val, Met, Leu, Ala, Asn, Giu or MLys;
Xaa at position 32 is Asp. Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Ar g;
Xaa at position 62 is Ser, Val, Asn, Pro, or Gly;
Xaa at position 63 is Ile or Leu;
Xaa at position 65 is Lys, Asn, Met, Arg, Ile, or Gl,;
Xaa at position 66 is Asn, Gly, Glu, or Arg;
Xaa at position 68 is Leu, Gln, Trp, Ar g, Asp. Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp. or Ala;
Xaa at position 81 is His, Pro, Arg, Val, Gly, Asn, Ser or Thr;

Xaa at position 84 is His, Ile, , Asn, Ala, Thr, Arg, Gln, Glu, Lys, Men, Ser, Tyr, Val or Leu;
Xaa at position 85 is Ile or Leu;
Xaa at position 86 is Lyo or Arg;
Xaa at position 87 is Asp. Pro, Met, Lys, His, Pro, Asn, Ile, Leu or Tyr;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys, Val, Trp, or Ile;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
and which can additionally have Met- or Met-Ala- proceding the amino acid in position 1; and wherein from 1 to 3 of the amino acids designated by Xaa are different from the corresponding amino acids of native (1–133)human interleukin-3.

8. The composition of 7, wherein said human inrerleukln-3 mutant polypeptide is of the Formula:
Xaa at position 17 is Ser, Lys, Asp. Met, Gln, or Arg;
Xaa at position 18 is Asn, His, Leu, Ile, Phe, Arg, or Gln;
Xaa at position 19 is Met, Arg, Gly, Ala, or Cys;
Xaa at position 20 is Ile, Cys, Gln, Glu, Arg, Pro, or Ala;
Xaa at position 21 is Asp. Phe, Lys, Arg, Ala, Gly, or Val;
Xaa at position 22 is Glu, Trp, Pro, Ser, Ala, His, or Gly;
Xaa at position 23 is Ile, Ala, Gly, Trp, Lys, Leu, Ser, or Arg;
Xaa at position 24 is Ile, Gin, Arg, or Ser;
Xaa at position 25 is Thr, His, Gly, Gln, Arg, Pro, or Ala;
Xaa at position 26 is His, Thr, Phe, Gly, Ala, or Trp;
Xaa at position 27 is Leu, Gly, Arg, Thr, Ser, or Ala;
Xaa at position 28 is Lys, Leu, Gln, Pro, Val or Trp;
Xaa at position 29 is Gln, Asn, Pro, Arg, or Val;
Xaa at position 30 is Pro, His, Tnr, Gly, Asp. Gln, Ser, Leu, or Lys;
Xaa at position 31 is Pro, Asp. Gly, Arg, Leu, or Gin;
Xaa at position 32 is Leu, Arg, Gln, Asn, Gly, Ala, or Glu;
Xaa at position 33 is Pro, Leu, Gln, Thr, or Glu;
Xaa at position 34 is Leu, Gly, Ser, or Lys;
Xaa at position 35 is Leu, Ala, Gly, Asn, Pro, or Gin;
Xaa at position 36 is Asp. Leu, or Val;
Xaa at position 37 is Phe, Ser, or Pro;
Xaa at position 38 is Asn, or Ala;
Xaa at position 40 is Leu, Trp, or Arg;
Xaa at position 41 is Asn, Cys, Arg, Leu, His, Met, Pro;
Xaa at position 42 is Gly, Asp. Ser, Cys, or Ala;
Xaa at position 42 is Glu, Asn, Tyr, Leu, Phe, Asp. Ala, Cys, or Ser;
Xaa at position 44 is Asp. Ser, Leu, Arg, Lys, Thr, Met, Trp, or Pro;
Xaa at position 45 is Gln, Pro, Phe, Val, Met, Leu, Thr, Lys, or Trp;
Xaa at position 46 is Asp. Phe, Ser, Thr, Cys, or Gly;
Xaa at position 47 is Ile, Gly, Ser, Arg, Pro, or His;
Xaa at position 48 is Leu, Ser, Cys, Arg, His, Phe, or Asn;
Xaa at position 49 is Met, Arg, Ala, Gly, Pro, Asn, His, or Asp;
Xaa at position 50 is Glu, Leu, Thr, Asp. or Tyr;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or;
Xaa at position 54 is Arg, Asp. Ile, Ser, Val, Thr, Gln, or Leu;
Xaa at position 55 is Arg, Thr, Val, Ser, Leu, or Gly;
Xaa at position 56 is Pro, Gly, Cys, Ser, Gln, or Lys;

Xaa at position 57 is Asr or Gly;
Xaa at position 58 is Leu, Ser, Asp. Arg, Gln, Val, or Cys;
Xaa at position 59 is Glu, His, Leu, Pro; or Arg;
Xaa at position 60 is Ala, Ser, Tyr, Asn, or Thr;
Xaa at position 61 is Phe, Asn, Glu, Pro, Lys, Arg, or Ser;
Xaa at position 62 is Asn His, Val, Arg, Pro, Thr, or Ile;
Xaa at position 63 is Arg, Tyr, Trp, Ser, Pro, or Val;
Xaa at position 64 is Ala, Asn, Ser, or Lys;
Xaa at position 65 is Val, Thr, Pro, His, Leu, Phe, or Ser;
Xaa at position 66 is Lys, Ile, Val, Asn, Glu, or Ser;
Xaa at position 67 is Ser, Ala, Phe, Val, Gly, Asn, Ile, Pro, or His;
Xaa at position 68 is Leu, Val, Trp, Ser, Thr, or His;
Xaa at position 69 is Gln, Ala, Pro, Thr, Arg, Trp, Gly, or Leu;
Xaa at position 70 is Asn, Leu, Val, Trp, Pro, or Ala;
Xaa at position 71 is Ala, Met, Leu, Arg, Glu, Thr, Gln, Trp, or Asn;
Xaa at position 72 Is Ser, Glu, Met, Ala, His, Asn, Arg, or Asp;
Xaa at position 73 is Ala, Glu, Asp. Leu, Ser Gly, Thr, or Arg;
Xaa at position 74 is Ile, Thr, Pro, Arg, Gly, Ala;
Xaa at position 75 is Glu, Lys, Gly, Asp. Pro, Trp, Arg, Ser, or Leu;
Xaa at position 76 is Ser, Val, Ala, Asn, Trp, Glu, Pro, Gly, or Asp;
Xaa at position 77 is Ile, Ser, Arg, or Tho;
Xaa at position 78 is Leo, Ala, Ser, Glu, Gly, or Arg;
Xaa at position 79 is Lys, Thr, Gly, Asn, Met, Ile, or Arg;
Xaa at position 80 is Asn, Trp, Val, Gl y, Thr, Leu, or Arg;
Xaa at position 81 is Leu, Gln, Gly, Ala, Arg, or Lys;
Xaa at position 82 is Leu, Gln, Lys, Trp, Arg, or Asp;
Xaa at position 83 is Pro, Thr, Trp, Arc, or Met;
Xaa at position 84 is Cys, Glu, Gly, Arg, Met, or Val;
Xaa at position 85 is Leu, Asn, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp. Cys, Leu, Val, Glu, His, or Asn;
Xaa at position 90 is Ala, Ser, Asp. Ile, or Met;
Xaa at position 91 is Ala, Ser, Thr, Phe, Leu, Asp or His;
Xaa at position 92 is Pro, Phe, Arg, Ser, Lys, His, or Leu;
Xaa at position 93 is Thr, Asp. Ser, Asn, Pro, Ala, Leu, or Arg;
Xaa at position 94 is Arg, Ile, Ser, Glu, Leu, Val, or Pro;
Xaa at position 95 is His, Gln, Pro, Val, Leu, Thr or TyL;
Xaa at position 96 is Pro, Lys, Tyr, Gly, Ile, or Thr;
Xaa at position 97 is Ile, Lys, Ala, or Asn;
Xaa at position 98 is His, Ile, Asn, Leu, Asp. Ala, Thr, or Pro;
Xaa at position 99 is Ile, Arg, Asp. Pro, Gln, Gly, Phe, or His;
Xaa at position 100 is Lys, Tyr, Leu, His, Ile, Ser, Gln, or Pro;
Xaa at position 101 is Asp. Pro, Met, Lys, His, Thr, Val, Tyr, or Gln;
Xaa at position 102 is Gly, Leu, Glu, Leu, Ser, Tyr, or Pro;
Xaa at position 103 is Asp. or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, or Hus;
Xaa at position 106 is Glu, Ala, Lys, Thr, Ile, Gly or Pro;
Xaa at position 108 is Arg, Asp. Leu, Thr, Ile, or Pro;
Xaa at position 109 is Arg, Thr, Pro, Glu, Tyr, Leu, Ser, or Gly.

9. A composition of 8, wherein said human interleukin-3 mutant polypeptide is of the Formula:

```
                    1                    5                       10
(Met)m—Ala  Pro  Met  Thr  Gln  Thr  Thr  Ser  Leu  Lys  Thr
                          15                      20
        Ser  Trp  Val  Asn  Cys  Ser  Xaa  Xaa  Xaa  Asp  Glu  Xaa  Ile
        25                         30                       35
        Xaa  His  Leu  Lys  Xaa  Pro  Pro  Xaa  Pro  Xaa  Leu  Asp  Xaa
                     40                      45                      50
        Xaa  Asn  Leu  Asn  Xaa  Glu  Asp  Xaa  Asp  Ile  Leu  Xaa  Xaa
                            55                      60
        Xaa  Asn  Leu  Arg  Xaa  Xaa  Asn  Leu  Xaa  Xaa  Phe  Xaa  Xaa
                     65                      70                      75
        Ala  Xaa  Lys  Xaa  Leu  Xaa  Asn  Ala  Ser  Xaa  Ile   Glu  Xaa
                            80                      85
        Ile  Leu  Xaa  Asn  Leu  Xaa  Pro  Cys  Xaa  Pro  Xaa  Xaa  Thr
        90                         95                       100
        Ala  Xaa  Pro  Xaa  Arg  Xaa  Pro  Ile   Xaa  Ile   Xaa  Xaa  Gly
                     105                     110                     115
        Asp  Trp  Xaa  Glu  Phe  Arg  Xaa  Lys  Leu  Xaa  Phe  Tyr  Leu
                            120                     125
        Xaa  Xaa  Leu  Glu  Xaa  Ala  Gln  Xaa  Gln  Gln  Thr  Thr  Leu
                     130
        Ser  Leu  Ala  Ile   Phe     [SEQ ID NO:7]
``` wherein m is 0 or 1; Xaa at position 18 is Asn or Ile; Xaa at position 19 Met, Ala or Ile; Xaa at position 20 is Ile, Pro or Leu; Xaa at position 23 is Ile, Ala or Leu; Xaa at position 25 is Thr or His; Xaa at position 29 as Gln, Arg, Val or Ile; Xaa at position 32 is Leu, Ala Asn, or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gln;

Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, Tyr; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp. Ala or Met; Xaa at position 105 is Asn or Glu; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; with the proviso that from one to three of the amino acids designated by Xaa are different from the corresponding amino acids of native human interleukin-3.

10. The composition of 9, wherein said human interleukin-3 mutant p plypeptide is of the Formula:

```
                    1              5                    10
  (Met_m—Ala_n)_p—Asn Cys Ser Xaa Xaa Xaa Asp Glu Xaa Ile
                   15                   20
  Xaa His Leu Lys Xaa Pro Pro Xaa Pro Xaa Leu Asp Xaa
             25              30                   35
  Xaa Asn Leu Asn Xaa Glu Asp Xaa Xaa Ile Leu Xaa Glu
                   40              45
  Xaa Asn Leu Arg Xaa Xaa Asn Leu Xaa Xaa Phe Xaa Xaa
        50              55              60
  Ala Xaa Lys Xaa Leu Xaa Asn Ala Ser Xaa Ile Glu Xaa
             65              70              75
  Ile Leu Xaa Asn Xaa Xaa Pro Cys Xaa Pro Xaa Xaa Thr
                   80              85
  Ala Xaa Pro Xaa Arg Xaa Pro Ile Xaa Ile Xaa Xaa Gly
             90              95             100
  Asp Trp Xaa Glu Phe Arg Xaa Lys Leu Xaa Phe Tyr Leu
                  105             110
  Xaa Xaa Leu Glu Xaa Ala Gln Xaa Gln Gln
```

[SEQ ID NO:8]

wherein m is 0 or 1; n is 0 or 1; p is 0 or 1; Xaa at position 4 is Asn or Ile; Xaa at position 5 is Met, Ala or Ile:

Xaa at position 6 is Ile, Pro or Leu; Xaa at position 9 is Ile, Ala or Leu; Xaa at position 11 is Thr or His; Xaa at position 15 is Gln, Arg, Val or Ile; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at pos it ior 35 is Met, Ile or Asp; Xaa at position 36 is Glu or Asp; Xaa at position 37 is Asn, Ara or Ser; Xaa at position 41 is Arg, Leu, or Thr; Xaa at position 42 is Pro or Ser; Xaa at position 45 is Glu or Leu; Xaa at position 46 is Ala or Ser; Xaa at P Jsition 48 is Asn, Val or Pro;

Xaa at position r Ar g or His; Xaa at position 51 is Val or Ser; Xaa at position 53 Ser, Asn, His or Gln; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Tyr; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp. Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from one to three of the amino acids designated by Xaa are different from the corresponding amino acids of native (15–125) human interieukin-3.

Also included in the present invention is a method of increasing multi-lineage hematopoietic cell production in a mammal in need thereof comprising administering a pharmaceutically effective amount of a human interleukin-3 mutant polypeptide as disclosed above with CSF, preferably G-CSF or GM-CSF simultaneously as a composition or one after the other.

Materials and methods for IL-3 variant Expression in E. coli

Unless noted otherwise, all specialt y chemicals were obtained from Sigma Co, (St. Louis, Mo.). Restriction endonucleases, T4 poly-nucleotides kinase, E. coli DNA polymerase I large fragment (klenow) and T4 DNA ligase were obtained from New England Biolabs (Beverly, Mass.).

Escherichia coli strains

Strain JM101: delta (pro lac), supE, thi, F' (traD36, rpoAB, lacI-Q, lacZdeltaM15) (Messing, 1979). This strain can be obtained from the American Type Culture Collection (ATCC), 12301 Parklawn Drive, Rockville, Md. 20852, accession number 33876. MON 105 (W3110 rpoH358) is a derivative of W3110 (Bachmann, 1972) and has been assigned ATCC accession number 55204. Strain GM48: dam-3, dcm-6, gal, ara, lac, thr, leu, tonA, tsx (Marinus, 1973) was used to make plasmid DNA that is not methylated at the sequence GATC.

Genes and plasmids

The gene used for hIL-3 production in E. coli was obtained from British Biotechnology Incorporated, Cambridge, England, catalogue number BBG14. This gene is carried on a pUC based plasmid designated pP0518. Many other human CSF genes can be obtained from R&D Systems, Inc. (Minn, Minn.) including IL-1 alpha, IL-1 beta, IL-2, IL-4, IL-5, IL-6, IL-7, IL-8, G-CSF, GM-CSF and LIF.

The plasmids used for production of hIL-3 in E. coli contain genetic elements whose use has been described (Olins et al, 1988; Olins and Rangwala, 1990). The replicon used is that of pBR327 (Covarrubias, et al, 1981) which is maintained at a copy number of about 100 in the cell (Soberon et al., 1980). A gene encoding the beta-lactamase protein is present on the plasmids. This protein confers amoicillin resistance on the cell. This resistance serves as a selectable phenotype for the presence of the plasmid in the cell.

For cytoplasmic expression vectors the transcription promoter Is derived from the recA gene of E. coli (Sancar et al., 1980). This promoter, designated precA, in clude- the RNA polymerase binding site and the lexA repressor binding site (the operator). This segment of DNA orovides high level transcription that is regulated even when the recA promoter is on a plasmid with the pBR327 origin of replication (Olins et al, 1988) incorporated herein by reference.

The ribosome binding site used is that from gene 10 of phage T7 (Olins et al, 1988). This is encoded in a 100 base pair (bp) fragment placed adjacent to precA. In the plasmids used herein, the recognition sequence for the enzyme NcoI (CCATGG) follows the g10-L. It is at this NcoI site that the hIL-3 genes were joined to the plasmid. It is expected that the nucleotide sequence at this junction will be recognized in mRNA as a functional start site for translation (Olins et al., 1988). The hIL-3 genes used were engineered to have a HindIII recognition site (AAGCTT) downstream from the coding sequence of the gene. At this Hindiii site is a 514 base pair RsaI fragment containing the origin of replication of the single stranded phage f1 (Dente et al, 1983; Olins, et al, 1 990) both incorporated herein by reference. A plasmid containing these elements is pMON2341. Another plasmid containing these elements is pMON5847 which has been deposited at the American Type Culture Collection, 12301 Parklawn Drive, Rockville, Md. 20852 under the accession number ATCC 68912.

In secretion expression plasmids the transcription promoter is derived from the ara B, A, and D genes of E. coli (Greenfield et al, 978). This promoter is designated pAra-BAD and is contained on a 323 base pair SacII, BglII restriction fragment. The LamB secretion leader (Wong et al, 1988, Ilement et al, 1981) is fused to the N-terminus of the hIL-3 gene at the recognition sequence tor the enzyme NcoI O (5'CCATGG3'). The hIL-3 genes used were engineered to have a HindIII recognition site (5'AAGCTT3') following the coding sequenceof the gene.

Recombinant DNA methods

Synthetic gene assembly

The hIL-3 varian- genes and other CSF genes can be constructed by the assembly of synthetic oligonucleotides. Synthetic oligonucleotides were designed so that they would anneal in complementary pairs, with protruding single stranded ends, and when the pairs were properly assembled would result in a DNA sequence that encoded a portion of the desired gene. Amino acid substitutions in the hIL-3 gene were made by designing the oligonucleotides to encode the desired substitutions. The complementary oligonucleotides were annealed at concentration of 1 picomole per microliter in ligation buffer plus 50 mM NaCl. The samples were heated in a 100 ml beaker of boiling water and permitted to cool slowly to room temperature. One picomole of each of the annealed pairs of oligonucleotides were ligated with approximately 0.2 plcomoles of plasmid DNA, digested with the appropriate restriction enzymes, in ligation buffer (25 mM Tris pH 8.0, 10 mM $MgCl_2$, 10 mM dithiothreitol, 1 mM ATP, 2mM spermidine) with T4 DNA ligase obtained from New England Biolabs (Beverly, Mass.) in a total volume of 20 Al at room temperature overnight.

Polymerase Chain Reaction

Polymerase Chain Reaction (hereafter referred to as PCR) techniques (Saiki, 1985) used the reagent kit and thermal cvcler from Perkin-Elmer Cetus (Norwalk, Conn.). PCR is based on a thermostable DNA polymerase from *Thermus anuaticus*. The PCR technique is a DNA amplification method that mimics the natural DNA replication process in that the number of DNA molecules doubles after each cycle, in a way similar to in vivo replication. The DNA polymerase mediated extension is in a 5' to 3' direction. The term "primer" as used herein refers to an oilgonucleoioce sequence that provides an end to which the DNA polymerase can add nuc deonioes that were complementary to a nucleoicde sequence. The faster nucleotide sequence is referred to as the "template", to which the primers were annealed. The amplified PCR product is defined as the region comprised between the 5' ends of the extension primers. Since the primers have defined sequences, the product will have discrete ends, corresponding to the primer sequences. The primer extension reaction is carried out using 20 picomoles (pmoles) of each of the oligonucleotides and 1 picogram of template plasmid DNA for 35 cycles (1 cycle is defined as 94 degrees C for one minute, 50 degrees C for two minutes and 72 degrees for three minutes.). The reaction mixture was extracted with an equal volume of phenol/chloroform (50% phenol and 50% chloroform, volume to volume) to remove proteins. The aqueous phase, containing the amplified DNA, and solyent phase were separated by centrifugation for 5 minutes in a microcentrifuge (Model 5414 Eppendort Inc, Fremont Calif.). To precipitate the amplified DNA the aqueous phase was removed and transferred to a fresh tube to which was added ½ volume of 3M NaoAc (pH 5.2) and 2.5 volumes of ethanol (100% stored an minus 20 degrees C.). The solution was mixed and placed on dry ice for 20 minutes. The DNA was pelleted by centrifugation for 10 minutes in a microcentrifuge and the solution was removed from the pellet. The DNA pellet was washed with 70% ethanol, ethanol removed and dried in a speedvac concentrator (Savant, Farmingdale, N.Y.). The pellet was resuspended in 25 microliters of TE (20mM Tris-HCl pH 7.9, 1 mM EDTA). Alternatively the DN A was precipitated by adding equal volume of 4M $NHg_4OAc$ and one volume of isopropanol [Treco et al., (1988)]. The solution was mixed and incubated at room temperature for minutes and centrifuged. These conditions selectively precipitat DNA fragments larger than ~20 bases and, were used to removed oligonucleotide primer. One quarter of the reaction was digested with restriction enzymes [Higuchi, (1989)] an on completion heated to 70 degrees C to inactivate the enzymes.

Recovery of recombinant plasmids from ligation mixes

*E. coli* JMll cells were made competent to take up DNA. Typically, 20 to 100 ml of cells were grown in LB medium to a density of approximately 150 Klett units and then collected by centrifugation. The cells were resuspended in one half culture volume of 50 mM CaCl2 and held at 4° C. for one hour. The cells were again collected by centrifugation and resuspended in one tenth culture volume of 50 mM CaCl2. DNA was added to a 150 microliter volume of these cells, and the samples were held at 4° C. for 30 minutes. The samples were shifted to 42° C. for one minute, one milliliter of LB was added, and the samples were shaken at 37° C. for one hour. Cells from these samples were spread on plates containing ampicillin to select for transformants. The plates were incubated overnight at 37° C. Single colonies were picked, grown in LB supplemented with ampicillin overnight at 37° C. with shaking. From these cultures DNA was isolated for restriction analysis.

Culture medium

LB medium (Maniatis et al, 1982) was used for growth of cells for DNA isolation. M9 minimal medium supplemented with 1.0% casamino acids, acid hydrolyzed casein, Difco (Detroit, Michigan) was used for cultures in which recombinant IL-3 variant was produced. The ingredients in the M9 medium were as follows: 3g/liter $KH_2PO_4$, 6g/l $Na_2HPO_4$, 0.5 g/l NaCl, 1 g/l $NH_4Cl$, 1.2 mM $MgSO_4$, 0.025 mM $CaCl_2$, 0.2% glucose (0.2% glycerol with the AraBAD promoter), 1% casamino acids, 0.1 ml/l trace minerals (per liter 108 g $FeCl_3 \cdot 6H_2O$, 4.0 g $ZnSO_4 \cdot 7H_2O$, 7·0 $COCl_2 \cdot 2H_2O$, 7.0 g $Na_2MoO_4 \cdot 2H_2O$, 8. 0 g $CuSO_4 \cdot 5H_2O$, 2·0 g $H_3BO_3$, 5·0 g $MnSO_4 \cdot H_2O$, 100 ml concentrated HCl). Bacto agar was used for solid media and ampicillin was added to both liquid and solid LB media at 200 micrograms per milliliter.

Production of IL-3 variants in *E. coli* with vectors employing the recA promoter

*E. coli* strains harboring the plasmids of interest were grown at 37° C. in M9 plus casamino acids medium with shaking in a Gyrotory water bath Model G76 from New Brunswick Scientific (Edison, N.J.). Growth was monitored with a Klett Summerson meter (green 54 filter), Klett Mfg. Co. (New York, N.Y.). At a Klett value of approximately 150, an aliquot of the culture (usually one milliliter) was removed for protein analysis. To the remaining culture, nalidixic acid (10mg/ml) in 0.1 N NaOH was added to a final concentration of 50 $\mu g$/ml. The cultures were shaken at 37° C. for three to four hours after addition of nalidixic acid. A high degree of aeration was maintained throughout the bacterial growth in order to achieve maximal production of the desired gene product. The cells were examined under a light microscope for the presence of retractile bodies (RBs). One milliliter aliquots of the culture were removed for analysis of protein content.

Extraction, RefoldinQ and Purification of IL-3 Variant Proteins Expressed as Refractile bodies in *E. coli*

Extraction of refractile bodies (RB's):

For each gram of RB's (and typically one gram is obtained from a 300 ml *E. coli* culture), 5 ml of a solution containing 6M guan idine hydrochloride (GnHCl), 50 mM 2-N-cyclohexylaminoethanesulfonic acid (CHES) pH 9.5 and 20 mM dithiothreitol (DTT) was added. The RB's were extracted with a Bio-Homogenizer for 15–30 seconds and gently rocked for 2 hours at 5 degrees centigrade (5° C.) to allow the protein on completely reduce and Refolding of the IL-3 Muteins The protein solution was transferred to dialysis tubing (100 molecular weight cut-off) and dialyzed against at least 100 volumes of 4M GnHCl–50 mM CHES pH 8.0. The dialysis was continued overnight at 5° C. while gently stirring. Subsequently dialysis was continued against at least 100 volumes of 2M GnHCl–50 mM CHES pH 8.0 and dialyzed overnight at 5° C. while gently stirring.

Purification of the IL-3 muteins

The protein solution was removed from the dialysis tubing and acidified by the addition of 40% acetonitrile ($CH_3CN$)–0.2% trifluoroacetic acid (TFA) to a final concentration of 20% $CH_3CN$–0.1% TFA. This was centrifuged (16,000×g for 5 minutes) to clarify and the supernatant was loaded onto a Vvdac C-18 reversed phase column (10×250 mm) available from Vydac (Hesperia, Calif. ) previously equilibrated in 20% $CH_3CN$–0.1% TFA. The column was eluted with a linear gradient (0.2% $CH_3CN$/minute) between 40–50% $CH_3CN$–0.1% TFA at a flow rate of 3 ml/minute while collecting 1.5 ml fractions. The fractions were analyzed by polyacrylamide gel electrophoresis (SDS-PAGE) and the appropriate fractions pooled. The pooled material was dried by lyophilization or in a Speed Vac concentrator. The dry powder was reconstituted with 10 mM ammonium bicarbonate pH 7.5, centrifuged (16,000×g for 5 minutes) to clarify and assayed for protein concentration by the method of Bradford (1976) with bovine serum albumin as the standard. Such protein can be further analyzed by additional techniques such as, SDS-PAG E, electrospra- y mass spectrometry, reverse phase HPLC, capillary zone electrophoresis, amino acid composition analysis, and ELIS (enzyme-linked immunosorbernt assay).

hIL-3 SANDWICH ELISA

The IL-3 variant protein concentrations can be determined using a sandwich ELISA based on an affinity purified polyclonal goat ant--rhIL-3. Microtiter plates (Dynatech Immulon II were coated with 150 µl goat-anti-rhIL-3 at a concentration of approximately 1µg/m L in 100 mI q NaHCO3, pH 8.2. Plates were incubated overnight at room temperature in a chamber maintaining 100% humidity. Wells were emptied and the remaining reactive sites on the plate were blocked with 200 µl of solution containing 10 mM PBS, 3% BSA and 0.05% Tween 20, pH 7.4 for 1 hour at 37° C. and 100% humiditv. Wells were emptied and washed 4× with 150 mM NaCi containing 0.05% Tween 20 (wash buffer). Each well then receives 150 µl of dilution buffer (10 mM PBS containing 0.1% BSA, 0.01% Tween 20, pH 7.4), containing rh IL-3 standard, control, sample or dilution buffer alone. A standard curve was preparec with concentrations ranging from 0.125 ng/T.l to 5 ng/ml using a stock solution of rhIL-3 (concentration determined by amino acid composition analysis). Plates were incubated 2.5 hours at 37° C. and 100% humidity. Wells were emptied and eac h plate was washed 4× with wash buffer. Each well then received 150 µl of an optimal dilution (as determined in a checkerboard assay format) of goat anti-rhIL-3 conjugated to horseradish neroxidase. Plates were incubated 1.5 hours at 37° C. and 100% humidity. Wells were emptied and eaon plate was washed 4× witn wash buffer. Each wel then received 150 µl of ABTS substrate so -ntion (Kirkegaard and Perry) Plates were Lncubated at room temperature unt, tne color of tne standard wells containing 5 ng/ml rhIiL-3 had developed enough to yield an absorbance between 0.5–1.0 where read at a test wavelength of 410 nm and a reference wavelength of 570 nm on a Dynatech microliter plate reader. Concentrations of immunoreactive rhIL-3 in unknown samples were calculated from the standard curve using software supplied with the plate reader.

AML Proliferation Assay for Bioactive Human Interleukin-3

The factor-dependent cell line AML 193 was obtained from the American Type Culture Collection (ATCC, Rockville, Md.). This cell line, established from a patient with acute myelogenous leukemia, was a growth factor dependent cell line which displayed enhanced growth in GM/CSF supplemented medium (Lange, B, et al., (1987); Valtieri, M, et al, (1987). The ability of AML 193 cells to proliferate in the presence of human IL-3 has also been documented. (Santoli, D, et al., (1987)). A cell line variant was used, AML 193 1.3, which was adapted for long term growth in IL-3 by washing out the growth factors and starving the cytokine dependent AML 193 cells for growth factors for 24 hours. The cells were then replated at $1\times10^5$ cells/well in a 24 well plate in media containing 100 U/ml IL-3. It took approximately 2 months for the cells to grow rapidly in IL-3. These cells were maintained as AML 193 1.3 thereafter by supplementing tissue culture medium (see below) with human IL-3.

AIL 193 1.3 cells were washed 6 times in cold Hanks balanced salt solution (HBSS, Gibco, Grand Island, N.Y.) by centrifuging cell suspensions at 250×g for 10 minuses followed by decantation of supernatant. Pelleted cells were resuspended in HBSS and the procedure was repeated until six wash cvcles were compleyed. Cells washed six times by this procedure were resuspended n tissue culture medium at a densit y ranging from $2\times10^5$ to $5\times10^5$ viable cells/ml. This medium was prepared by supplementing Iscove's modified Dulbecco's Medium (IMDM, HazIleton, Lenexa, Kans.) with albumin, transferrin, lipids and 2-mercaptoethanol. Bovine albumin (Boehringer-Mannheim, Indianapolis, Ind.) was added at 500 µg/ml; human transferrin (Boehringer-Mannheim, Indianapolis, Ind.) was added at 100 µg/ml; soybean lipid (Boehringer-Mannheim, Indianapolis, Ind.) was added at 50 µg/ml; and 2-mercaptoethanol (Sigma, St. Louis, Mo.) was added at $5\times10^{-5}$M.

Serial dilutions of human interleukin-3 or human interleukin-3 variant protein (hIL-3 mutein) were made in triplicate series in tissue culture medium supplemented as stated above in 96 well Costar 3596 tissue culture plates. Each well contained 50 µl of medium containing interleukin-3 or interleukin-3 variant protein once serial dilutions were completed. Control wells contained tissue culture medium alone (negative control). AML 193 1.3 cell suspensions prepared as above were added to each well by pipetting 50 µl ($2.5\times10^4$ cells) into each well. Tissue culture plates were incubated at 37° C. with 5% $CO_2$ in humidified air for 3 days. On day 3, 0.5 µCi $^3$H-thymidine (2 Ci/mM, New England Nuclear, Boston, Mass.) was added in 50 µl of tissue culture medium. Cultures were incubated at 37° C. with 5% $CO_2$ in humidified air for 18–24 hours. Cellular DNA was harvested onto glass filter mats (Pharmacia LKB, Gaithersburg, Md.) using a TOMTEC cell harvester (TOMTEC, Orange, CT) which utilized a water wash cycle followed by a 70% ethanol wash cycle. Filter mats were allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) was added. Beta emissions of samples from individual tissue culture wells were counted in a LKB Be caplate model 1205 scintillation counter (Pharmacia LKB, Gaithersburg, Md.) and data was expressed as counts per minute of $^3$H-thymidine incorporated int c cells from each tissue culture well. Activity of each human interleukin-3 preparation or human interleukin-3 variant preparation was quantitated by measuring cell proliferation ($^3$H-thymidine incorporation induced by graded concentrations of interleukin-3 or interleukin-3 variant. Typicall y, concentration ranoes from 0.05 pM -$10^5$ pM were quantitated in these assays. Activity was determined by measuring the dose of interleukin-3 or interleukin-3 variant which provides 50% of maximal proliferation [EC50=0.5× (maximum average counts per minute of $^3$H-thymidine incorporated per well among triplicate cultures of all concentrations of interleukin-3 tested– background proliferation measured by $^3$H-thymidine incorporation observed in triplicate cultures lacking interleukin-3]. This $EC_{50}$ value is also equivalent to 1 unit of bloactivity. Every assay was performed with native interleukin-3 as a reference standard so that relative activity levels could be assigned.

Methylcellulose Assay

This assay provides a reasonable approximation of the growth activity of colony stimulating factors to stimulate normal bone marrow cells to produce different types of hematopoietic colonies in vitro (Bradley et al, 1966, Pluznik et al, 1965).

Methods

Approximately 30 ml of fresh, normal, healthy bone marrow aspirate are obtained from individuals. Under sterile conditions samples are diluted 1:5 with a 1XPBS (#14040.059 Life Technologies, Gaithersburg, Md.) solution in a 50 ml conical tube (#25339-50 Corning, Corn ingn Md.). Ficoll (Histopaque-1077 Sigma H-8889) is layered under the diluted sample and centrifuged, 300 x g for 30 min. The mononuclear cell band is removed and washed two times in 1XPBS and once with 1% BSA PBS (CellPro Co., Bothel, Wash.). Mononuclear cells are counted and CD34+ cells are selected using the Cetrate LC (CD34) Kit (CellPro Co., Bothel, Wash. column. This fractionation is performed since all stem and progenitor cells within the bone marrow display CD34 surface antigen. Alternatively whole bone marrow or oeripheral blood may be used. Cultures are set up in triplicate wells with a final volume of 0.1 ml in 48 well tissue culture plates (#3548 CoStar, Cambridge, Mass.). Culture medium is purchased from Terry Fox Labs. (HCC-4330 medium (Terry Fox Labs, Vancouver, B.C, Canada)). 600–1000 CD34+cells are added per well. Native IL-3 and IL-3 variants are added to give final concentrations ranging from ·001nM-lOnm. G-CSF and GM-CSF and C-Kit licand are added at a final concentration of 0.1nm. Native IL-3 and IL-3 variants are supplied in house. C-Kit Ligand (#255-CS), G-CSF (#214-CS) and GM-CSF (#215-GM) are purchased from R&D Systems (Minneapolis, Minn.). Cultures are resuspended using an Eppendorf repeater and 0.1 ml is dispensed per well. Control (baseline response) cultures received no colony stimulating factors. Positive control cultures received conditioned media (PHA stimulated human cells:Terry Fox Lab. $H_{2400}$). Cultures are incubated at 37° C., 5% CO02 in humidified air. Hematopoietic colonies which are defined as greater than 50 cells are counted on the day of peak response kdays 10–11) using a Nikon inverted phase microscope with a 40× objective combination. Groups of cells containing fewer than 50 cells are referred to as clusters. Alternatively colonies can be identified bv spreading the colonies on a slide and stained or thev can be picked, resuspended and spun onto cvtospin s -i aes for staining.

Human Cord Blood Hemooolectic Growth Factor Assavs

Bone marrow cells are traditionally used for in vitro assa ys of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al, 1992; Mayani et al, 1993). In contrast to bone marrow, cord blood is more readily available on a regular basis. There is also a potential to reduce assay variability by pooling cells obtained fresh from severa donors, or to create a bank of cryopreserved cells for this purpose. By modifying the culture conditions, and/or analyzing for lineage specific markers, it should be possible to assay specifically for granulocyte / macrophage colonies (CFU-GM), for megakaryocyte CSF activity, or for high proliferative potential colony forming cell (HPP-CFC) activity.

METHODS

Mononuclear cells (MNC) are isolated from cord blood within 24 hrs of collection, using a standard density gradient (1.077g/ml Histopaque). Cord blood MNC have been further enriched for stem cells and progenitors by several procedures, including immunomagnetic selection for CD14–, CD34+ cells; panning for SBA-, CD34+fraction using coated flasks from Applied Immune Science (Santa Clara, Calif.); and CD34+ selection using a CelIlPrc (Bothell, Wash.) avidin column. Either freshly isolated or cryopreserved CD34+ cell enriched fractions are used for the assay. Duplicate cultures for each serial dilution of sample (concentration range from 1pm to 1204pm) are prepared with 1×104 cells in 1ml of 0.9% methocellulose conta ining medium without additional growth factors (Methocult H4230 from Stemr Cell Technologies, Vancouver, BC.). In some experiments, Methocult H4330 containing ervthropoietin (EPO) was used instead of Methocult H4230, or Stem Cell Factor (SCF), 50ng/m I (Biosource International, Camarillo, Calif.) was added. After culturing for 7–9 days, colonies containing >30 cells are counted. In order to rule out subjective bias in scoring, assays are scored blind.

IL-3 mediated sulfidoleukotriene release from human mononuclear cells

The following assay was used to measure IL-3 mediated sulfidoleukotriene release from human mononuclear cells. Heparin-containing human blood was collected and lavered onto an equal volume of Ficoll-Paque (Pharmacia #17-0840-02) ready to use medium (density 1.077 g/ml.). The Ficoll was warmed to room temperature prior to use and clear 50 ml polystyrene tubes were utilized. The Ficoll gradient was spun at 300×g for 30 minutes at room temperature using a H1000B rotor in a Sorvall RT6000B refrigerated centrifuge. The band containing the mononuclear cells was carefully removed, the volume adjusted to 50 mls with Dulbecco's phosphate-buffered saline (Gibco Laboratories cat. #310-4040PK), spun at 400×g for 10 minutes at 4° C. and the supernatant was carefully removed. The cell pellet was washed twice with HA Buffer [ 20 mM Hepes (Sigma # H-3375) 125 mM NaCl (Fisher # S271–500), 5 mM KCl (Sigma # P-9541), 0.5 mM glucose (Sigma # G-5000), 0.025% Human Serum Albumin (Calbiochem # 126654and spun at 300×g, 10 min, 4° C. The cells were resuspended in HACM Buffer (HA buffer supplemented with 1 mM CaC12 (Fisher # C.79-500) and 1 nM Mgcl2 (Fisher #M-33) at a concentration of 1×106 cell/ml and 180 $\mu$l were transferres into each well of 96 well tissue culture plates.

The cells were allowed to acclimate at 37° C. for 15 minutes. The cells were primed by adding 10 $\mu$ls of a 20× stock of various concentrations of cytokine to each well (typically 100000, 20000, 4000, 800, 160, 32, 6.4, 1.28, 0 fM IL3). The cells were incubated for 15 minutes at 37° C. Sulfidoleukotriene release was activated by the addition of 10 μls of 20×(1000 nM) fmet-leu, phe (Calbiochem # 344252) final concentration 50nM 10 FMLP and incubated for 10 minutes at 37° C. The plates were spun at 350×g at 4° C. for 20 minutes. The supernatants were removed and assayed for sulfidoleukotrienes using Cayman's Leukotriene C4 EIA kit (Cat. #420211) according to manufacturers' directions. Native (15–125)hIL-3 was run as a standard control in each assay.

Further details of genetic engineering techniques known to those skilled in the art may 20 be found in T. Maniatis, et al, *Molecular Clonin g A Laboratorv Manual*, Cold Spring Harbor Laboratory (1982) and references cited therein, incorporated herein by reference; and in J.

Sambrook, et al, *Molecular Cloning, A Laboratory Manual*, 2nd edition, Cold Spring Harbor Laboratory (1989) and references cited therein, incorporated herein by reference.

Amino acids are shown herein bv standard one letter or three letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Compositions of the present invention comprise a therapeutically effective amount of one or more of the hIL-3 muteins of the oresent invention in a mixture with a pharmaceuticall acceptable carrier with CSF. This composilion can be administered either parenterally, intravenously or subcutaneously. When administered, the therapeutic composition for use in this invention is preferably in the form of a pyrogen-free, parenterally acceptable aqueous solution. The preparation of such a parenteraily acceptable protein solution, having due regard to pH, isotonicity, stability and the like, is within the skill of the art.

The dosage regimen involved in a method for treating the above-described conditions will be determined by the attending physician considerin g various factors which modify the action of drugs, e.g. the condition, body weight, sex and diet of the patient, the severity of any infection, time of administration and other clinical factors. Generally, a daily regimen may be in the range of 0.2–150 μg/kg of non-glycosylated IL-3 protein per kilogram of body weight and 0.2–150 μg/kg of CSFS per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given mutein vs. the activity of native (reference) IL-3 and it would not be unreasonable to note that dosage regimens may include doses as low as 0.1 microgram and as high as 1 milligram per kilogram of body weight per day. As indicated above, the therapeutic method and compositions may also include co-administration with other human factors. A non-exclusive list of other appropriate hematopoletins, CSFs and interleukins for simultaneous or serial co-administration with the polypeptides of the present invention includes GM-CSF, CSF-1, G-CSF, Meg-CSF, M-CSF,Serythropoietin (EPO), IL-1, IL-4, IL-2, IL-5, IL-6, IL-7, IL-8, IL-9, IL-10, IL-11, LIF, B-cell growth factor, B-cell differentiation factor and eosinoohil differentiation factor, stem cell factor (SCF I also known as steel factor or c-kit ligand, or combinations thereof. Progress of the treated patient can be monitored by periodic assessment of the hematological profile, e.g., differential cell count and the like.

Additional details may be found in co-pending International (published as WO 94/12639) application Ser. No. PCT/US93/11198 (published as WO 94/12639), now allowed as U.S, application Ser. No. 08/411,796; which is hereby incorporated by reference in its entirety as if written herein.

Additional details on how to make the compositions of the present invention can be found in WO 91/07988.

Additional details about the CSFs and the variants thereof can be found in U.S. Pat. No. 810,643, 5,218,092 and E.P. Application 02174004.

All references, patents or applications cited herein are incorporated by reference in their entirety as if written herein.

Various examples will be apparent to the person skilled in the art after reading the present disclosure without departing from the spirit and scope of the invention. It is intended that all such examples be included within the scope of the appended claims.

References

Adams, S. P., Kavka, K. S., Wykes, E. J., Holder, S. B. and Galluppi, G. R. Hindered Dialkyamino Nucleoside Phosphate reagents in the synthesis of two DNA 51-mers. *J. Am. Chem. Soc,* 105, 661–66 3 (1983).

Atkinson, T. and Smith, M, in Gait, M. J., *Oligonucleotide Sythesis* (1984) (IRL Press, Oxford England).

Bachmann, B., Pedigrees of some mutant strains of *Escherichia coli* K-1I, *Bacteriological Reviews,* 36:525- 557 (1972 ).

Bayne, M. L., Expression of a synthetic gene encodin human irsulin-like growth factor I in cultured mouse fibroblasts. *Proc. Nat . Acad. Sci. USA* 84, 2638–2642 (1987).

Ben-Bassat, A., K. Bauer, S-Y. Chang, K. Myambo, A. Boosman and S. Ching. Processing of the initiating melhionine from proteins: properties So the Escherichia coli methionine aminopeptidase and its gene structure. *J. Bacteriol,* 169: 751–757 (1987)

Biesma, B. et al, Effects of interleukin-3 after chemotherapy for advanced ovarian cancer. *Blood,* 80:1141–1148 (1992).

Birnboim, H. C. and J. Doly. A rapid alkaline extraction method for screening recombinant plasmid DNA. *Nucleic Acids Research,* 7(6): 1513–1523 (1979).

Bradford, M. M., A rapid and sensitive method for the quantitation of microgram quantities of protein utilizing the principle of protein-dye binding, *Analytical Biochemistry,* 72: 248–254 (1976).

Bradley, T. R. and Metcalf, D. The growth of mouse bone marrow cells in vitro. *Aust. Exp. Biol. Med. Sci.* 44:2 87–300, (1966).

Briddell, R. A., Hoffman, R., Cytokine regulation of the human burst-forming unit megakaryocyte, *Blood* 76:516, (1990).

Broxmeyer, H. E. et al, Growth characteristics and expansion of human umbilical cord blood and estimation of its potential for transplantation in adults, *Proc. Natl. Acad. Sci. USA*, vol.89, 4109–4113, 1992.

Bruno, E., Miller, M. E., Hoffman, R., Interacting cytokines regulate in vitro human megakaryocytopoiesis, *Blood* 76:671,(1990).

Bruno, E., Copper, R. J., Briddell, R. A., Hoffman, R., Further examinatior of the effects of recombinant cytokines or the proliferation of human megakaryocyte, progenitor cells, Blood 77:2339, (1991).

Clark-Lewis, I., L. E. Hood and S. B. H. Kent. Role of disulfide bridges in determining the biological activit y of interleukin 3, *Proc. Natl. Acad. Sci.* 85: 7897–7901 (1988).

Clement, J. M. and Hofnung, M. Gene sequence of the receptor, an outer membrane protein of *E. coli* K12. *Cell,* 27: 507–514 (1981).

Covarrubias, L., L. Cervantes, A. Covarrubias, X. Soberon, I. Vichido, A. Blanco, Y. M. Kupersztoch-Portnoy and F. Bolivar. Construction and characterization of new cloning vehicles. V. Mobilization and coding properties of pBR322 and several deletion derivates including pBR327 and pBR328.Gene 13: 25–35 (1981). D'Andrea, A. D., Lodish, H. G., Wong, G. G.:Expression cloning of the murineServthropoielin receptor. *Cell* 57:277, 1989

Deng, W. P. & Nickoloff, J. A. Site-directed mutagenesis of virtually any plasmid by eliminating a unique site *Anal. Biochem.* 200:81 (1992).

Dente, L., G. Cesareni and R. Cortese, pEMBL: a new family of single stranded plasmids, *Nucleic Acids Research,* 11: 1645–1655 (1983).

Donahue, R. E., Seehra, J., Metzger, M., Lefebvre, D., Rock, B., Corbone, S., Nathan, D. G., Garnick, M., Seghal, P. K., Laston, D., La Valle, E., McCoy, J., Schendel, P. F., Norton, C., Turner, K., Yang, Y. C., and Clark, S. C., Human IL-3 and GM-CSF act synergistically in stimulating hematopoiesis in primates. *Science.* 241: 1820, (1988 ).

Dunrn, J. J. and Studier, F. W., Complete nucleotide sequence of bacteriopnhage T7 DNA and-lthe locations of T7 genetic elements. *J. Mol. Blol.* 166:477–535 (1983).

Emerson, S. G., Yang, Y. C., Clark, S. C., and Long, M. W., Humaan recombinant human GM-CSF and IL-s have overlapping bur distinct hematopoietic activities, *J. Clin. Invest.* 82:1282, (1988).

Falk, S., G. Seipelt, A. Ganser, O. G. Ottmann, D. Hoelzer, H. J. Stutte and K. Hubner. *Hematopathology* 95: 355 (1991).

Fling, M. E, et al. Nucleotide sequence of the transposon Tn7 gene encoding an aminoglycoside-modifying enzyme, 3" (9)-O-nucleotidyltransferase. *Nucl. Acids Res.* 13:7095–7106 (1985).

Ganser, A, A. Lindemann, G. Seipelt, O. G. Ottmann, F. Herrmann, M. Eder, J. Frisch, G. Schulz, R. Mertelsmann and D. Hoelzer. Effects of Recombinant Human Interleukin-3 in Patients With Normal Hematopoiesis and in Patients with Bone Marrow Failure, *Blood* 76: 666 (1990).

Ganser, A., Lindemann, A., Ottmann, O. G., Seipelt, G., Hess, U., Geissler, G., Kanz, L., Frisch, J., Schultz, G., Mertelsmann, R., and Hoelzer, D., Sequential in vivo treatment with two recombinant human hematopoietic growth factors (IL-3 and GM-CSF) as a new therapeutic modalitv to stimulate hematopoiesis: Results of a Phase I study, Blood 79: 2583, (1992).

Gearing, D. P., King, J. A., Gough, N. M., Nicola, N. A.: Expression cloning of a receptor for human granulocyte-macrophage colony-stimulating factor. EMBO J 8:366 7, 1989

Gearing, D. P, Thut, C. J, VandenBos, T., Gimpel, S. D., Delanev, P. B, King, J. A., Price V, Cosman, D., Beckman MP: Leukemia inni bitory factor receptor is structurally related to the IL-6 signal transducer, gp130. *EMBO J* 10:2839, 1991

Gething and Sambroo s, Cell-surface expression or influenza haemagglutinin from a cloned DNA copy of the RNA gene, Nature, 293: 620–625 (1981).

Gillio, A. P, C. Gasparetro, J. Laver, M. Abboud, M. A. Bonilla, M. B. Garnick and R. J. O'Reilly. J. Clin. Invest. 85: 1560 (1990).

Gouy, M. and G. Gautier, Codon usage in bacteria: Correlation with gene expressivity, *Nucleic Acids Research,* 10: 7055–7074 (1982).

Greenfield, L, T. Boone, and G. Wilcox. DNA sequence of the araBAD promoter in Escherichia coli B/r. *Proc. Natl. Acad. Sci. USA,* 75: 4724–4728 (1978).

Harada, N, Castle, B.E, Gorman, D. M, Itoh, N., Schreurs, J, Barrett R. L, Howard, M, Miyajima, A.: Expression cloning of a cDNA encoding the murine interleukin 4 receptor based on ligand binding. *Proc Natl Acad Sci USA* 87:857, 1990

Higuchl, R, (1989) in PCR Technolo c v, H. A. Erlich ed., Stockton Press, N.Y. chapter 2–6.

Hunkapiller, M. W, R. W. Hewick, R. J. Dreyer and L. E. Hood. High sensitivity sequencing with a gas-phase sequenator. *Methods in Enzymology* 153: 399–413 (1983).

Kaufman, et al, Coamplification and Coexpression of Human Tissue-Type Plasminogen Activator and Murine Dihydrofolate Reductase Sequences in Chinese Hamster Ovar y Cells, *Mol. Cell. Biol,* 5(7): 1750–1759 (1985).

Kaufman, R. J. High level production of proteins in mammalian cells, in *Geneti c En gineerin g, Principles and Methods*, Vol. 9, J. K. Set -lo, editor, Plenum Press, New York (1987

Kelso, A. Gough, N. M.: Coexpession c f granulocyte-macrophage colony-stimulating factor. g-interferon and interleukins-, and 4 is random in murine alloreactive T lymphocyte hoonese. *Proc Natl Acad Sci USA* 85:9189, 1988

Kitamura, T . Tange, T, Terasawa, T, Chiba, S, Kuwaki, T, Miyagawa, K, Piao, Y, Miyazono, K, Urabe, A, and Takaku, F, Establishment and Characterization of a Unique Human Cell Line That Proliferates Dependently on GM-CSF or Erythropoietin, *Journal of Cellular Physiolooy,* 140: 323–334 (1989.

Kitamura, T., Sato, N, Arai, K, M iyajima, A.: Expression cloning of the human IL-3 receptor CDNA reveals a shared beta subunit for the human IL-3 and GM-CSF receptors. *Cell* 66:1165, 1991

Kondo, M, Takeshita, T, Ishii, N, Nakamura, M., Watanabe, S, Arai, K-I, Sugamura, K.: Sharing of the Interleukin-2 (IL-2) Receptor g Chain Between Receptors for IL-2 and Il-4. *Science* 262:1874, 17 Dec. 1993.

Krumwieh, D, Weinmann, E, Seiler, F. R, Different effects of interleukin-3 (IL-3) on the hematopoiesis of subhuman primates due to various combinations with GM-CSF and G-CSF, *Int. J. Cell Cloning* 8: 229, (1990).

Kunkel, T. A. Rapid and efficient site-specific mutagenesis without phenotyoic selection. *Proc. Natl. Acad. Sci. USA* 82: 488–492 (1985).

Laemmli, U. K, Cleavage of structural proteins during assemblv of the head of bacteriophage T4, *Nature,* 227:68–68 5 (1970).

Lange, B., M. Valtieri, D. Santoli, D. Caracciolo, F. Mavilio, . Gemperiern, C. Griffin, B. Emanuel, J. Finan, P. Nowell, and G. Rovera. Growth factor requirements of childhood acute leukemia: establishment of CM-CSF-defendern. cell line s. *Blood* 70:192 (1987).

Maekawa, T, Metcalf, D, Gearing, D. P.: Enhanced suppression of human myeloid leukemic cell Lines b a a combination of IL-6, LIF, GM-CSF and G-CSF, Int J Cancer 45:35 3, 1989

Mahler, H. R. and E. H. Cordes, in *Biological Chemistry, p.* 128, New York, Harper and Row (1966).

Maniatis, T, E. F. Fritsch and J. Sambrook, *Molecular Cloning, A Laboratory Manual. Cold Spring Harbor Laboratory* (1982).

Marinus, M. G. Location of DNA methylation genes on the Escherichia coli K-12 genetic map. *Molec. Gen. Genet.* 127: 47–55 (1973).

Mayani, H. et al, Cytokine-induced selective expansion and maturation ofSerythroid versus myeloid progenitors from purified cord blood precursor cells, *Blood*, vol. 81, 3252–3258,1993.

Mazur, E et al, *Blood* 57:277–286, (1981).

McBride, L. J. and Caruthers, M. H. An investigation of several deoxynucleoside phosphorarmidites. *Tetrahedron Lett,* 24, 245–248 (1983).

Messing, J, A multipurpose cloning systerr based on the single-stranded DNA bacteriophage M13. *Recombinant DNA Technical Bulletin*, NIH Publ -cation No. 79–99, Vol. 2, No. 2, pp. 43–48 (1979).

Metcalf, D, Begley, C. G, Williamson, D, Nice, E. C., DeLamarter, J., Mermod J-J, Thatcher D, Scnmidt, A.: Hemopoietic responses in mice in jected w i b-h purified recombinant murine CM-CSF. *Exp Hematol* 15:1, 1987

Met calf, D.: The molecular control of cell division, differentiation - commitment and maturartion in haemopoietic cells. *Nature* 339:27, 1989

Metcalf, A, Nicola, N.A.: Direc - proliferative ac ion - . of stem cell factor on murine bone marrow cells in vitro. Effects of combinatin with colonv-stimula cing factors. *Proc Natl Acad Sci USA* 88:6239, 1991

Metcalf, D, Nicola, N. A, The clonal proliferation of narmal mouse hematopoietic cells: Enhancement and suppression by colony stimulating factor combinations, *Blood* 79: 2861, (1992)

Metcalf, D, Hematopoletic Regulators: Redundancy or Subtlety. *Blood,* 182: 3515–3523 (1993).

Neu, H. C. and L. A. Heppel. The release of enzymes from Escherichia coli by osmotic shock and during the formation of spheroplasts. *J. Biol. Chem,* 240: 3685–3692 (1965).

Noguchi, M, Nakamura, Y, Russell, S.M, Ziegler, S. F., Tsang, M, Xiqing, C, Leonard, W. J.: Interleukin-2 Receptor g Chain: A Functional Component of the Interleukin-7 Receptor. *Science* 262:1877, 17 Dec 1993.

Nordon, P, and Potter, M, A Macrophage-Derived Factor Required by plasmacytomas for Survival and Proliferation in Vitro, *Science* 233:566, (1986).

Obukowic7, M.G, Staten, N.R. and Krivi, G.C, Enhanced Heterologous Gene Expression in Novel rpoH Mutants of Escherichia coli. Al ilied and Environmental *Microbiology* 58, No. 5, p. 1511–1523 (1992).

Olins, P. O, C. S. Devine, S. H. Rangwala and K. S. Kavka, The T7 phage gene 10 leader RNA, a ribosome-binding site tha dramatically enhances the expression of foreign genes in Escherichia coli, *Gene,* 73:22–23.

Olins, P. O. and S. H. Rangwala, Vector for enhanced translation of foreign genes in *Escherichia col i, Methods in Enzymolo my,* 185 . 11 5–19 (1990).

Ploemacher, P. E, van Soest, P. L, Voorwinden, H, and Boudewijn, A, Interleukin-12 Svner cizes with Interleukin-3 and Steel Factor to Enhance Recovery of Murine Hemopoietic Stem Cells in Liquid Culture, *Leukimia,* 7: no 6, 1381–1388, (1993). Pluznik, D. H and Sachs, L. Cloning of normal "mast" cells in tissue culture. *J Cell Comp Physiol* 66:319–324 (1965).

Postmus, et al, Effects of recombinant human interleukin-3 in patients with relapsed small-cell lung cancer treated with chemotherapy: a dose-finding study. *J. Clin. Oncol,* 10:1131–1140 (1992).

Prober, J. M, G. L. Trainor, R. J. Dam, F. W. Hobbs, C. W. Robertson, R. J. ZagursKy, .A. J. Cocuzza, M. A. Jensen and K. Baumeisrer. A system for rapid DNA sequencing with fluorescent chain-terminating dideoxynucleotides. *Science* 238: 336–341 (1987).

Renart J, J. Reiser and G. R. Stark, Transfer of proteins from gels to diazobenzvloxymethyl-paper and detection with anti-sera: a method for studying antibody specificity and antigen structure, *Proc. Natl. Acad. Sci. USA,* 76:3116–3120 (1979).

Robinscn, B. E, McGrath, H, Quesenberry, P. J, Recombinant murine GM-CSF has megakarocvte stimulating action and augments megakarvocvte c cionv St lmulating by IL-3 . *J. Clin,. Invest.* 79: 1548, (1987).

Russell, S. M., Keegan, A. D., Harada, N, NaKamura, Y., Noguchi, M., Leland, P., Friedmann, M.C., Miyajima, A., Puri, R. R, Paul, W. E, Leonard, .J.: Interieukirn-2 Receptor g Chain: . A Functional Component of the Interleukin-4 Receptor. *Science* 262:1880, 17 Dec 1993.

Saiki, R. K, Schorf, S, Faloona, F, Mullis, K. B., Horn, G. T, Erlich, H. A. and Arnheim, N, Enzymatic Amplification of β-Globin Genomic Sequences and Restriction Site Analysis for Diagnosis of Sickle Cell Anemia, *Science,* 230: 1350–1354 (1985).

Sambrook, J, et al, *Molecular Cloning, A Laboratory Manual,* 2nd edition, Cold Spring Harbor Laboratory (1989).

Sancar, A., C. Stachelek, W. Konigsberg and W. D. Rupp, Sequences of the recA gene and protein, *Proc. Natl. Acad. Sci,* 77: 2611–2615 (1980).

Sanger, F, S. Nicklen and A. R. Coulson. DNA 20 sequencing with chain-terminating inhibitors. *Proc. Natl. Acad. Sci. USA* 74: 5463–5467 (1977).

Santoli, D., Y. Yang, S. C. Clark, B. L. Kreider, D. Caracciolo, and G. Rovera. Synergistic and antagonistic effects of recombinant human interleukin (IL-3), IL-1, granulocyte and macrophage colonystimulating factors (G-CSF and M-CSF) on the growth of GM-CSF-dependent leukemic cell lines. *J. Immunol.* 139:348 (1987).

Sherr, C.J.: Colony-stimulating factor-1 receptor. *Blood* 75:1, 1990

Smith, M. In vitro mutagenesis. *Ann. Rev. Genet.,* 19:423–462 (1985).

Soberon, X., L. Covarruoras and F. Bolivar, Construction and characterizaticrt of new cloning vehicles. IV. Deletion derivatives of pBR322 and pBR325, Gene, 9: 211–223 (1980)

Sonoda, Y, Yang, Y aC, Wong, GG, Clark, SC, Ogawa, M, Analysis in serum-free culture of the tar aets of recombinant human hemopoietic growth factors: IL-3 and GM-CSF are specific for early developement stages , *Proc Natl Acad Sci USA,* 85: 4360, (1988).

Stader, J. A. and T. J. Si ihavy. Engineering Escherichia coll to secrete heterologous gene produo cs, *Methods in Enzymolocr y,* 185: 166–87 (1990).

Stahl, C. P, Winton, E. F, Monroe, M. C, Haff, E, Holman, R. C, Meyers, L. A, Liehl, E, and Evatt, B, Differential effects of sequential, simultaneous and single agent IL-3 and and GM-CSF on megakaryocyte maturation and platelet response in primates, *Blood,* 80: 2479, (1992).

Summers, M. D. and G. E. Smith. A manual of methods for Baculovirus vectors and insect cell culture procedures. *Texas Aoricultural Experiment Station Bulletin No.* 1555 (1987).

Takaki, S., Tominage, A., Hitoshi, Y., Mita S., Sonada, E., Yamaguchi, N., Takatsu, K.: Molecular cloning and expression of the murine interleukin-5 receptor. *EMBO. J* 9:4367, 1990

Taylor, J. W., Ott, J. and Eckstein, F. The rapid generation of oligonucleotide-directed mutants at high frequency using phosphorothioate modified DNA. *Nucl. Acids Res,* 13:8764–8785 (1985).

Treco, D.A, (1989) in Current Drotocols in Molecular Biology, Seidman et al., eds. J. Wiley N.Y., unit 2.1.

Valtieri, M., D. Santoli, D. Caracciolo, B. L. Kreider, S. W. Altmann, D. J. Tweardy, I. Gemperlein, F. Mavilio, B. J. Lange and G. Rovera. Establishment and characterization of an undifferentiated human T leukemia stimulating factor for growth. *J. Immunol.* 138:4042 (1987).

Voe , D, W. B. Gatzer, R. A. Cox, P. Doty. Absorption spectra of the common bases. *Biopolymers* 1: 193 (1963).

Weinberg, R. A., De Ciechi, P. A., Obukowicz, M.: A chromosomal expression vector for *Escherichia coli* based on the bacteriophage Mu. *Gene* 126 (1993) 25–33.

Wells, J. A., Vasser, M, and Powers, D. B. Cassette mutagenesis: an effective method for generation of multiple mutants at defined sites. *Gene,* 34:315–323 (1985).

Wong, Y. Y., R. Seetharam, C. Kotts, R. A. Heeren, B. K. Klein, S. B. Braford, K. J. Mathis, B. F. Bishop, N. R. Siegel, C. E. Smith and W. C. Tacon. Expression of secreted IGF-1 in *Escherichia coli. Gene,* 68: 193–203 (1988).

Yanisch-Perron, C, J. Viera and J. Messing. Improved M13 phage cloning vectors and host strains: nucleotide sequences of the M13mp18 and pUC19 vectors. Gene 33: 103–119 (1985).

Yamasaki, K., Taga, T., Hirata, Y., Yawata, H., Kawanishi, Y., Seed, B., Taniguchi, T., Hirano, T., Kishimoto, T.: Cloning and expression of the human interleukin-6 (BSF-2?IFN beta 2) receptor. *Science* 241:82 5, 1988

Yarden Y., Kuang, W-J., Yang-Feng, T., Coussens, L., Munemitsu, S., Dull, T. J., Chen, E., Schlesinger, J., Francke, U., Ullrich, A., Human proto-oncogene c-kit: A new cell surface receptor tyrosine kinase for an unidentified ligand. *EMBO J* 6:3341, 1987

Zoller, M. J. and Smith, M. Oligonucleotide-directed mutagenesis using M13-derived vectors: an efficient and general procedure for the production of point mutations in any lfragrnt of DNA. Nucleic Acid Research, 10: 6487–6500 (1982).

Zoller, M. J. and Smith, M. Oligonucleotide-directed mutagenesis of DNA fragments cloned ino M13 vectors. *Methods in Enzylmology,* 100:468–500 (1983).

Zoller, M. J. and Smith, M. Oligonucleotide-directed Mutagenesis: A simple method using two oligonucleotide primers and a single-stranded *DNA,* 3: 479 (1984).

---

What is claimed is:

1. A composition comprising; a mutant human interleukin-3 polypeptide comprising;
a modified interleukin-3 amino acid sequence selected from the group consisting of:
(a) an amino acid sequence of SEQ ID NO:1
(b) an N-terminal Met residue, or Met-Ala dipeptide joined to an amino acid sequence according to (a),
wherein
Xaa at position 17 is Ser, Lys, Gly, Asp. Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, G it, Arg, Pro, or Ala;
Xaa at position 21 is Asp. Phe, Lys, Arg, Ala, Gly, Glu, Gln, Asn, Thr, Ser or Val;
Xaa at position 22 is Gl u, Trp, Pro, Ser, Ala, His, Asp. Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;

Xaa at position 3 0 is Pro, His, Thr, Gly, Asp. Gln, Ser, , Leu, or Lys;

Xaa at position 31 is Pro, Asp. Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, Gly, Asn, Pro, Gln, or Valt

Xaa at position 36 is Asp. Len, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp. Ser, Cys, Asn, Lys, Thr, Leu, Val, Glu, Phe, Tyr, Ile, Met or Ala;

Xaa at position 43 is Glu, Asn, Tyr, LeU, Phe, Asp. Ala, Cys, Gln, Arg, Thr, Gly or Ser;

Xaa at position 44 is Asp. Ser, Leu, Arg, Lys, Thr, Met, Ttp, Glu, Asn, Gln, Ala or Pro;

Xaa at position 45 is Gln, Pro, Phe, VAt, Met, Leu, Thr, Lys, Trp, Asp. Asn, Arg, Ser, Ala, Ile, Glu or His;

Xaa at position 46 is Asp. Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Al a, Met, Val or Asn;

Xaa at position 49 is Met, Arg, Ala, Gly, Pro, Asn, His, or Asp;

Xaa at position 50 is Glu, Leu, Thr, Asp. Tyr, Lys, Asn, Ser, Ala, Ile, Val, His, Phe, Met or Gln;

Xaa at position 51 is Asn, Arg, Met, Pro, Ser, Thr, or His;

Xaa at position 52 is Asn, His, Arg, Le a. Gly, Ser, or Thr;

Xaa at position 53 is Leu, Thr, Ala, Gly, Gl, Pro, Lys, Ser, or Met;

Xaa at position 54 is Arg, Asp. Ile, Ser, Val, Thr, Gln, Asn, Lys, His, Ala or Leu;

Xaa at position 55 is Arg, Thr, Val, Ser, Leu, or Gly,

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp. Arg, Gln, Val, or Cys;

Xaa at position 59 is Glu, Tyr, His, Len, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, ASp, or Ile;

Xaa at position 63 is Arg, Tyr, Trp, Lys, Ser, His, Pro, or Vat;

Xaa at position 64 is Ala, Asn, Pro, Ser, or Lys;

Xaa at position 65 is Valt, Thr, Pro, His, Leu, Phe, or Ser;

Xaa at position 66 is Lys, Ile, Arg, Val, Asn, Glu, or Ser;

Xaa at position 67 is Ser, Ala, Phe, Val, Gly, Asn, Ile, Pro, or His;

Xaa at position 68 is Leu, Val, Trp, Ser, Ile, Phe. TPhr, or His;

Xaa at position 69 is Gln, Ala, Pro, Thr, Glu, Arg, Trp, Gly, or Len;

Xaa at position 70 is Asn, Leu, Vat, Trp, Pro, or Ala;

Xaa at position 71 is Ala, Met, Leu, Pro, Arg, Gln, Thrr Gln, Trp. or Asn F

Xaa at position 72 is Ser, Gli, Met, Ala, His, Asn, Arg, or Asp;

Xaa at position 73 is Ala, Glu, Asp. Leu, Ser, Gly, Thr, or Arg;

Xaa at position 74 is Ile, Met, Thr, Pro, Axg, Gly, Ala;

Xaa at position 75 is Glu, Lys, Gly, Asp. Pro, Trp, Arg, Ser, Gl in, or Leu;

Xaa at position 76 is Ser, Val, Ala, Asn, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp. Glu, Asn, His, Thr, Ser, Ala, Tyr, Phe, Ile, Met or V z jl;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys. Arg, Val, or Trp;

Xaa at position 89 is Thr, Asp. Cys, Leu, Val, Glu, His, Asn, or Ser;

Xaa at position 90 is Ala, Pro, Ser, Thr, Gly, Asp. Ile, or Met;

Xaa at position 91 is Ala, Pro, Ser, Thr, Phe, Leu, Asp. or His:

Xaa at position 92 is Pro, Phe, Arg, Ser, Lys, His, Ala, Cly, Ile or Leu;

Xaa at position 93 is Thr, Asp. Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, aly, Thr, Asn, Lys, Ser, Ala, Trp, Phe, Ile, or Tyr;

Xaa at position 96 is Pro, Lys, Tyr, Gly, Ile, or Tht; r

Xaa at position 97 is Ile, Val, Lys, Ala, or Asn;

Xaa at position 98 is His, Ile, Asn, Len, Asp. Ala, Thr, Glu, Gl a, Ser, Phe, Met, Val, Lys, Arg, Tyr or Pro;

Xaa at position 99 is Ile, Leu, Arg, Asp. Val, Pro, Gln, Gly, Ser, Phe, or His;

Xaa at position 100 is Lys, Tyr, Leu, His, Arg, Ile, Ser, Gln, or Pro;

Xaa at position 101 is Asp;

Xaa at position 102 is Gly, Leu, Gli, Lys, Ser, Tyr, or Pro;

Xaa at position 103 is Asp. or Ser;

Xaa at position 104 is Trp, Val, cys, Tyr, Thr, Met, Pror Leu, Gln, Lys, Ala, Phe, or Gly;

Xaa at position 105 is Asn, Pro, Ala, Phe, Ser, Trp, Gln, Tyr, Leu, Lys, Ile, Asp. or HisF Xaa at position 106 is Glu, Ser, Ala, Lys, Thr, Ile, Gly, or Pro;

Xaa at position 108 is Arg, Lys, Asp. Leu, Thr, Ile, Gln, His, Ser. Ala or Pro;

Xaa at position 109 is Arg, Thr, Pro, Gln, Tyr, Leu, Ser, or Cly;

Xaa at position 110 is Lys, Ala, Asn, Thr, Leu, Arg, Gln, His, Glu, Ser, Ala, or Trp;

Xaa at position 111 is Leu, Ile, Arg, Asp. or Met;

Xaa at position 112 is Thr, Val, Gln, Tyr, Glu, His, Ser, or Phe;

Xaa at position 113 is Phe, Ser, Cys, His, Gly, Trp, Tyr, Asp. Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is L au, Ser, Pro, Ala, Glu, Cys, Asp. or Tyr,

Xaa at position 119 is Glu, Ser. Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp. or Gly;

Xaa at position 122 is Gln, Ser, Met, Trp, Arg, Phe, Pro, His, Ile, Tyr, or Cys;

Xaa at poSition 123 is Ala, Met, Glu, His, Ser, Pro, Tyr, or Leu;

wherein from 1 to 3 of the amino acids designated by Xaa are different from the corresponding amino acids of native (1–133) human interleukin-3; wherein from 1 to 14 amino acids can optionally be deleted from the N-terminus and/or from 1 to 15 amino acids can optionally be deleted from the C-terminus of said modified interleukin-3 amino acid sequence; said human interleukin-3 mutant polypeptide having at least three times greater cell proliferative activity than native human interleukin-3, in at least one assay selected from the group consisting of AML cell proliferation, TF-1 cell proliferation and Methylcellulose assay; and a factor which is a colony stimulating factor, acytokine, alymphokine, an interleukin, or a hematopoietic factor.

2. A composition comprising a mutant human interleukin-3 polypeptide comprising;

a modified interleukin-3 amino acid sequence selected from the group consisting of:

(a) an amino acid sequence of SEQ ID NO:1

(b) an N-terminal Met residue, Ala residue, or Met-Ala dipeptide joined to an amino acid sequence accordind to (a), wherein Xaa at position 17 is Ser, Lys, Gly, Asp. Met, Gln, or Arg;

Xaa at position 18 is Asn, His, Leu, Ile, Phe, Arg, or Gln;

Xaa at position 19 is Met, Phe, Ile, Arg, Gly, Ala, or Cys;

Xaa at position 20 is Ile, Cys, Gln, Glu, Arg, Pro, or Ala;

Xaa at position 21 is Asp. Phe, Lys, Arg, Ala, Gly, Gl, Gln, A sn, Thr, Ser or Val;

Xaa at position 22 is Glu, Trp, Pro, 5r, Ala, His, Asp. Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Leu;

Xaa at position 25 is Thr, His, Gly. Gln, Arg, Pro, or Ala;

Xaa at position 26 is His, Thr, Phe, Gly, Arg, Ala, or Trp;

Xaa at position 27 is Leu, Gly, Arg, Thr, Ser, or Ala;

Xaa at position 28 is Lys, Arg, Leu, Gln, Gly, Pro, Val or Trp;

Xna at position 29 is Gln, Asn, Leu, Pro, Arg, or Val;

Xaa at position 30 is Pro, His, Thr, Gly, Asp. Gln, Ser, Leu, or Lys;

Xaa at position 31 is Pro, Asp. Gly, Ala, Arg, Leu, or Gln;

Xaa at position 32 is Leu, Val, Arg, Gln, Asn, Gly, Ala, or Glu;

Xaa at position 33 is Pro, Leu, Gln, Ala, Thr, or Glu;

Xaa at position 34 is Leu, Val, Gly, Ser, Lys, Glu, Gln, Thr, Arg, Ala, Phe, Ile or Met;

Xaa at position 35 is Leu, Ala, aly, Asn, Pro, Gln, or Val;

Xaa at position 36 is Asp. Leu, or Val;

Xaa at position 37 is Phe, Ser, Pro, Trp, or Ile;

Xaa at position 38 is Asn, or Ala;

Xaa at position 40 is Leu, Trp, or Arg;

Xaa at position 41 is Asn, Cys, Arg, Leu, His, Met, or Pro;

Xaa at position 42 is Gly, Asp. Ser, Cys, Asni, Lys, Thr, Leu, Val, Gl, Phe, Tyr, Ile, Met or Ala;

Xaa at position 43 is GlU, Asn, Tyr, Leu, Phe, Asp. Ala, Cys, G il, Arg, Thr, Gly or Ser;

Xaa at position 44 is Asp. Ser, Leu, Arg, Lys, Thr, Met, Trp, Glu, Asn, Gln, Ala or Pro;

Xaa at position 45 is Gln, Pro, Phe, Val, Met, Leu, Thr, Lys, Trp, Asp. Asn, Arg, Ser, Ala, Ile, Glu or His;

Xaa at position 46 is Asp. Phe, Ser, Thr, Cys, Glu, Asn, Gln, Lys, His, Ala, Tyr, Ile, Val or Gly;

Xaa at position 47 is Ile, Gly, Val, Ser, Arg, Pro, or His;

Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;

Xaa at position 50 is Glu, Leu, Thr, Asp. Tyr, Lys, Asn, Ser, Ala, Ile. Val, His, Phe, Met or Gln;

Xaa at position 51 is Asn, Arg, Met, Pro, Ser, Thr, or His;

Xaa at position 52 is Ash, His, Arg, Leu, Gly, Ser, or Thr;

Xaa at position 53 is Len, Thr, Ala, Gly, Glu, Pro, Lys, Ser, or Met;

Xaa at position 54 is Arg, Asp. Ile, Ser, Val, Thr, Gln, Asn, Lys, His, Ala or Leu;

Xaa at position 55 is Arg, Thr, Val, Ser, Leu, or Gly,

Xaa at position 56 is Pro, Gly, Cys, Ser, Gln, Glu, Arg, His, Thr, Ala, Tyr, Phe, Leu, Val or Lys;

Xaa at position 57 is Asn or Gly;

Xaa at position 58 is Leu, Ser, Asp. Arg, Gln, Val, or Cys;

Xaa at position 59 is Glu, Tyr, His, Leu, Pro, or Arg;

Xaa at position 60 is Ala, Ser, Pro, Tyr, Asn, or Thr;

Xaa at position 61 is Phe, Asn, Glu, Pro, Lys, Arg, or Ser;

Xaa at position 62 is Asn, His, Val, Arg, Pro, Thr, Asp. or Ile;

Xaa at position 63 is Arg, Tyr, Trp, Lys, Ser, His, Pro, or Val;

Xaa at position 64 is Ala, Asn, Pro, Ser, or Lys,

Xaa at position 65 is Val, Thr, Pro, His, Leu, Phe, or Ser;

Xaa at position 66 is Lys, Ile, Arg, Val, Asrn, Glu, or Ser;

Xaa at position 67 is Ser, Ala, Phe, Val, Gly, Asn, Ile, Pro, or His;

Xaa at position 68 is Len, Val, Trp, Ser, Ile, Phe, Thr, or His;

Xaa at position 69 is Gln, Ala, Pro, Thr, Glu, Arg, Irrp, Gly, or Len;

Xaa at position 70 is Asn, Leu, Val, Trp, Pror or Al;

Xaa at position 71 is Ala, Met, Leu, Pro, Arg, Glu, Thr, Gln, Trp, or Asn:

Xaa at position 72 is Ser, Glu, Met, Ala, His, Asn, Arg, or Asp;

Xaa at position 73 is Ala, Glu, Asp. Leu, Ser, Gly, Thr, or Arg;

Xaa at position 74 is Ile, Met, Thr, Pro, Arg, Cly, Ala;

Xaa at position 75 is Glu, Lys, Gly, Asp. Pro, Trp, Arg, Ser, Gln, or Leu;

Xaa at position 76 is Ser, Val, Ala, Asa, Trp, Glu, Pro, Gly, or Asp;

Xaa at position 77 is Ile, Ser, Arg, Thr, or Leu;

Xaa at position 78 is Leu, Ala, Ser, Glu, Phe, Gly, or Arg;

Xaa at position 79 is Lys, Thr, Asn, Met, Arg, Ile, Gly, or Asp;

Xaa at position 80 is Asn, Trp, Val, Gly, Thr, Leu, Glu, or Arg;

Xaa at position 81 is Leu, Gln, Gly, Ala, Trp, Arg, Val, or Lys;

Xaa at position 82 is Leu, Gln, Lys, Trp, Arg, Asp. Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Giu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, Asp. Cys, Leu, Val, Glu, His, Asn, or Ser;

Xaa at position 90 is Ala, Pro, Ser, Thr, Gly, Asp. Ile, or Met;

Xaa at position 91 is Ala, Pro, Ser, Thr, Phe, Leu, Asp. or His,

Xaa at position 92 is Pro, Phe, Arg, Ser, Lys, His, Ala, Gly, Ile or Leu;

Xaa at position 93 is Thr, Asp. Ser, Asn, Pro, Ala, Leu, or Arg;

Xaa at position 94 is Arg, le, Ser, Glu, Leu, Val, Gln, Lys, His, Ala, or Pro;

Xaa at position 95 is His, Gln, Pro, Arg, Val, Leu, Gly, Thr, Asn. Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp. Ala, Thr, Glu, Gln, ser, Phet Met, Val, Lys, Arg, Tyr or Pro;

Xaa at position 99 is Ile, Leu, Arg, Asp. Val, Pro, Gln, Gly, Ser, Phe, or His;

Xaa at position 100 is Lys, Tyr, Le m, His, Arg, Ile, Ser, Gln, or Pro;

Xaa at position 101 is Asp;

Xaa at position 102 is Gly, Leu, Glu, Lys, Ser, Tyr, or Pro;

Xaa at position 103 is Asp. or Ser,

Xaa at position 104 is Trp, Val, Cys, Tyr, Thr, Met, Pro, Leu, Gln, Lys, Ala, Phe, or Gly, Xaa at position 105 is Asn, Pro, Ala, Phe, Ser, Trp, Gln, Tyr, Le m, Lys, Ile, Asp. or His;

Xaa at position 106 is Glt, Ser, Ala, Lys, Thr, Ile, Gly. or Pro;

Xaa at position 108 is Arg, Lys, Asp. Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Set, Ala, or Trp;

Xaa at position 111 is Leu, Ile, Arg, Asp. or Met;

Xaa at position 112 is Thr, Val, Gln, Tyr, Glu, His, Ser, or Phe;

Xaa at position 113 is Phe, Ser, Cys, His, Gly, Trp, Tyr, Asp. Lys, Leu, Ile, Val or Asn;

Xaa at position 114 is Tyr, Cys, His, Set, Trp, Arg, or Leu;

Xaa at position 115 is Leu, Asn, Val, Pro, Arg, Ala, His, Thr, Trp, or Met;

Xaa at position 116 is Lys;

Xaa at position 117 is Thr, Ser, Asn, Ile, Trp, Lys, or Pro;

Xaa at position 118 is Leu, Set, Pro, Ala, Gln, Cys, Asp. or Tyr;

Xaa at position 119 is Glu, Ser, Lys, Pro, Leu, Thr, Tyr, or Arg;

Xaa at position 120 is Asn, Ala, Pro, Lel a, His, Val, or Gln;

Xaa at position 121 is Ala, Ser, Ile, Asn, Pro, Lys, Asp. or Gly;

Xaa at position 122 is Gln, Ser. Met, Trp, Arg, Phe, Pro, His, Ile, Tyr, or Cys;

Xaa at position 123 is Ala, Met, Glu, His, Ser, Pro, Tyr, or Le u A;

wherein from 1 to 3 of the amino acids designated by Xaa are different from the corresponding amino acids of native (1–133) human interleukin-3; wherein from 1 to 14 amino acids can optionally be deleted from the N-terminus and/or from 1 to 15 amino acids can optionally be deleted from the C-terminus of said modified interleukin-3 amino acid sequence; and said human interleukin-3 mutant polypeptide having at least three times greater cell proliferative activity than native human interleukin-3, in at least one assay selected from the group consisting of: AML cell proliferation, TF-1 cell proliferation and Methylcellulose assay; and a factor selected from the group consisting of; GM-CSF, CSF-1, G-CSF, G-CSF ($Serl^7$), X-CSF, erythropoietin ( SPO), IL-1, IL-4, IL-2, IL-5, IL-6, IL-7, IL-8, IL-9, IL-10, IL-11, IL-12, IL-13, LIF, flt3/flk2 ligand, human growth hormone, B-cell growth factor, B-cell differentiation factor, eosinophil differentiation factor and stem cell factor (SCF).

3. The composition according to claim 2, wherein said modified interleukin-3 amino acid sequence is selected from the group consisting of:

(a) an amino acid sequence of SEQ ID NO:2

(b) an N-terminal Met residue, Ala residue, or Met-Ala-dipeptide joined to an amino acid sequence accordind to (a), where in Xaa at position 17 is Ser Gly, Asp. Met, or Gln;

Xaa at position 18 is Asn, His, or Ile;

Xaa at position 19 is met or Ile;

Xaa at position 21 is Asp or Glu;

Xaa at position 23 is Ile, Ala, Leu, or Gly;

Xaa at position 24 is Ile, Val, or Leu;

Xaa at position 25 is Thr, His, Gln, or Ala;

Xaa at position 26 is His or Ala;

Xaa at position 29 is Glnr, Asn, or Val;

Xaa at position 30 is Pro, Gly, or Gln:

Xaa at position 31 is Pro, Asp. Gly, or Gln;

Xaa at position 32 is Leu, Arg, Gln, Asn, Gl Iy, Ala, or Glu;

Xaa at position 33 is Pro or Glu;

Xaa at position 34 is Leu, Val, Gly, Ser, Lys, Ala, Arg, Gln, Glu, Ile, Phe, Thr or Met;

Xaa at position 35 is Leu, Ala, Asn, Pro, Gln, or Val;

Xaa at position 37 is Phe, Ser, Pro, or Trp;

Xaa at position 38 is Asn or Ala;

Xaa at position 42 is Gly, Asp. Ser, Cys, Ala, Asn, Ile, Leu, Met, Tyr or Arg;

Xaa at position 44 is Asp or Glu;

Xaa at positi,on 45 is Gln, Val, Met, Leu, Thr, Ala, Asn, Glu, Ser or Lys;

Xaa at position 46 is Asp. Phe, Ser, Thr, Ala, Asn, Gln, Glu, His, Ile, Lys, Tyr, Val or Cys;

Xaa at position 50 is Glu, Ala, Asn, Ser or Asp;

Xaa at position 51 is Asn, Arg, Met, Pro, Ser, Thr, or His;

Xaa at position 54 is Arg or Ala;

Xaa at position 55 is Arg, Thr, Val, Leu, or Gly;

Xaa at position 56 is Pro, Gly, Ser, Gln, Ala, Arg, Asn, Glu, Leu, Thr, Val or Lys;

Xaa at position 60 is Ala or Ser;

Xaa at position 62 is Asn, Pro, Thr, or Ile;

Xaa at position 63 is Arg or Lys;

Xaa at position 64 is Ala or Asn;

Xaa at position 65 is Val or Thr;

Xaa at position 66 is Lys or Arg;

Xaa at position 67 is Ser. Ph e, or His;

Xaa at position 68 is Leu, Ile, Phe, or His;

Xaa at position 69 is Gln, Ala, Pro, Thr, Glu, Arg, or Gly;

Xaa at position 71 is Ala, Pro, or Arg;

Xaa at position 72 is Ser, Glu, Arg, or Asp;

Xaa at position 73 is Ala or Leu;

Xaa at position 76 is Ser, Val, Ala, Asn, Glu, Pro, or Gly;

Xaa at position 77 is Ile or Le u a;

Xaa at position 79 is Lys, Thr, Gly, Asn, Met, Arg, Ile, Gly, or Asp;

Xaa at position 80 is Asn, Gly, Glu, or Arg;

Xaa at position 82 is Len, Gln, Trp, Arg, Asp. Ala, Asn, Glu, His, Ile, Met, Phe, Ser, Thr, Tyr or Val;

Xaa at position 83 is Pro or Thr;

Xaa at position 85 is Leu or sal;

Xaa at position 87 is Le u or Ser;

Xaa at position 88 is Ala or Trrp;

Xaa at position 91 is Ala or Pro;

Xaa at position 93 is Thr, Asp. Ser, Pro, Ala, Le u, or Arg;

Xaa at position 95 is His, Pro, Arg, Val, Leu, Gly, Asn, Phe, Ser or Thr;

Xaa at position 96 is Pro or Tyr;

Xaa at position 97 is ILe or Val;

Xaa at position 98 is His, Ile, Asn, Leu, Ala, Thr,, Arg, Gln, Lys, Met, Ser, Tyr, Val or Pro;

Xaa at position 99 is Ile, Leu, or Val;

Xaa at position 100 is Lys, Arg, Ile, Gln, Pro, or Ser;

Xaa at position 101 is Asp;

Xaa at position 104 is Trp or Leu;

Xaa at position 105 is Asn, Pro, Ala, Ser, Trp, Gln, Tyr, Leu, Lys, Ile, Asp. or His;

Xaa at position 106 is Glu or Gly;

Xaa at position 108 is Arg, Ala, or Ser;

Xaa at position 109 is Arg, Thr, Clu, Leu, or Ser;

Xaa at position 112 is Thr, Val, or Gln;

Xaa at position 114 is Tyr, or Trp;

Xaa at position 115 is Leu or Ala;

Xaa at position 116 is Lys;

Xaa at position 117 is Thr or Ser;

Xaa at position 120 is Asn, Pro, Leu, His, Val, or Gln;

Xaa at position 121 is Ala, Ser, Ile, Asn, Pro, Asp. or Gly;

Xaa at position 122 is Gln, Ser, Met, Trp, Arg, Phe, Pro, His, Ile, Tyr. or cys;

Xaa at position 123 is Ala, Met, Glu, His, Ser. Pro, Tyr, or Letn;

wherein from 1 to 3 of the amino acids designated by Xaa are different from the corresponding amino acids of native (1–133) human interleukin-3; wherein from 1 to 14 amino acids can optionally be deleted from the N-terminus and/or from 1 to 15 amino acids can optionally be deleted from the C-terminus of said modified interleukin-3 amino acid sequence.

4. The composition according to claim 2, wherein said modified interleukin-3 amino acid sequence is selected from the group consisting of:

(a) an amino acid sequence of SEQ ID NO :3

(b) an N-terminal Met residue, Ala residue, or Met-Ala dipeptide joined to an amino acid sequence according to (a), wherein Xaa at position 17 is Ser, Gly, Asp. or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn. or Ala;

Xaa at position 34 is Leu, Val. Ser. Ala, Arg, Gln, Glu, Ile, Phe, Thr, or Met;

Xaa at position 3S is Leu, Ala, Asn, or Pro;

Xaa at position 38 is Asn or Ala;

Xaa at position 42 is Gly, Asp. Ser, Ala, Asn, Ile, Leu, Met, Tyr, or Arg;

Xaa at position 45 is Gln, Val, Met, Leu, Ala, Asn, Glu, or Lys;

Xaa at position 46 is Asp. Phe, Ser, Gln, Glu, His, Val or Thri

Xaa at position 50 is Glu, Asn, Ser or Asp;

Xaa at position 51 is Asn, Arg;, Pro, Thr, or His;

Xaa at position 55 is Arg, Leu, or Gl.y;

Xaa at position 56 is Pro, Gly, Ser, Ala, Asn, Val, Leu or Gln;

Xaa at position 62 is Asn, Pro, or Thr;

Xaa at position 64 is Ala or Asn;

Xaa at position 65 is Val or Thr;

Xaa at position 67 is Ser or Phe;

Xaa at position 68 is Lieu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Leu, Gln, Trp, Arg, Asp. Asn, Glu, His, Met, Phe, Ser, Thr, Tyr or Val;

Xaa at position 87 is Leu or Ser;

Xaa at position 88 is Ala or Trp;

Xaa at position 91 is Ala or Pro;

Xaa at position 93 is Thr, Asp. or Ala;

Xaa at position 95 is His, Pro, Arg, Val, Gly, Asn, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Gl Q, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, Glu, Ser, or Leu;

wherein from 1 to 3 of the amino acids designated by Xaa are different from the corresponding amino acids of native (1–133) human interleukin-3; wherein from 1 to 14 amino acids can optionally be deleted from the N-terminus and/or from 1 to 15 amino acids can optionally be deleted from the C-terminus of said modified interleukin-3 amino acid sequence.

5. A composition of claim 4 wherein, in said modified interleukin-3 amino acid sequence(a):

Xaa at position 42 is Gly, Asp. Ser, Ile, Leu, Met, Tyr, or Ala;

Xaa at position 45 is Gln, Val, Met or Asn;

Xaa at position 46 is Asp. Ser, Gln, His or Val;

Xaa at position 50 is Glu or Asp;

Xaa at position 51 is Asn, Pro or Tlhr;

Xaa at position 62 is Asn or Pro;

Xaa at position 76 is Ser, or Proi

Xaa at position 82 is Leu, Trp, Asp. A sn Clu, His, Phe, Ser or Tyr;

Xaa at position 95 is His, Arg, Thr, Asri or Ser;

Xaa at position 98 is His, Ile, Leu, Ala, Gln, Lys. Met, ser, Tyr or Val;

Xaa At position 100 is Ly s or Arg;

Xaa at position 105 is Asn, or Pro;

Xaa at position 108 is Arg, Ala, or Ser,

Xaa at position 121 is Ala, or Ile;

Xaa at position 122 is Gln, or Ile; and

Xaa at position 123 is Ala, Met or Glu.

6. A composition comprising a mutant human interleukin-3 polypeptide comprising a modified interleukin-3 amino acid sequence selected from the group consisting of:

(a) an amino acid sequence of SEQ ID NO:4; and (b) an N-terminal Met residue, Ala residue, or Met-Ala dipeptide joined to an amino acid sequence according to (a), wherein Xaa at position 3 is Ser, Lys, Gly, Asp. Met, Gln, or Arg;

Xaa at position 4 is Asn, His, Leu, Ile, Phe, Arg, or Gln;

Xaa at position 5 is Met, Phe, Ile, Arg, Gly, Ala, or Cys,

Xaa at position 6 is Ile, cys, Gln, Gli, Arg, Pro, or Ala;

Xaa at position 7 is Asp. Phe, Lys, Arg, Ala, Oly, Glu, Gln, Asn, Thr, Ser or Val;

Xaa at position 8 is Glu, Trp, Pro, Ser, Ala, His, Asp. Asn, Gln, Leu, Val, or Gly;

Xaa at position 9 is Ile, Val, Ala, Leu, Gly, Trp, Lys, Phe, Ser, or Arg;

Xaa at position 10 is Ile, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, Gly, Pro, Val or Trp;

Xaa at position 15 is Gln, Asn, Leu, Pr o, Arg, or Val;

Xaa at position 16 is Pro, His, Thr, Gly, Asp. Gln, Ser, Leu, or Lys;

Xaa at position 17 is Pro, Asp. Gly, Ala, Arg, Leu, or Gln;

Xaa at position 18 is Leu, Val, Arg, Gln, Asn, Gly, Ala, or Glu;

Xaa at position 19 is Pro, Leu, Gln, A Ma, Thr, or Glu;

Xaa at position 20 i z Leu, Val, Gly, Ser, Lys, Clu, Gln, Thr, Arg, Ala, Phe, Ile or Met;

Xaa at position 21 is Leu, Ala, Gly, Asn, Pro, Gln, or Val;

Xaa at position 22 is Asp. Leu, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, cys, Arg, Leu, His, Met, Pro;

Xaa at position 28 is Gly, Asp. Ser, Cys, Ala, Lys, Asn, Thr, Leu, Val, Glu, Phe, Tyr, Ile or Met;

Xaa at position 29 is Glu, Asn, Tyr, Leu, Phe, Asp. Ala, Cys, Gli, Arg, Thr, Gly or Ser;

Xaa at position 30 is Asp. Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp. As h, Arg, Ser, Ala, Ile, Glu, His or Trp;

Xaa at position 32 is Asp. Phe, Ser, Thr, Cyzs, Olu, Asn, Gln, Lys, His, Ala, Tyr, Ile, Val or Gly, Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp. Tyr, Lys, Asa, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp. Ile, Ser, Val, Thr, Gln, Asn, Lys, His, Ala or Leu;

Xaa at position 41 is Arg, Thr, Val, Ser, Leu, or Gly;

Xaa at position 42 is Pro, Gly, Cys, Ser, Gln, Glu, Arg, His, Thr, Ala, Tyr, Phe, Len, Val or Lys;

Xaa at position 43 is Asn or Gly;

Xaa at position 44 is Leu, Ser, Asp. Arg, Gln, Val or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is A gn, His, Val, Arg, Pro, rhr, Asp. or Ile;
Xaa at position 49 is Arg, Tyr, Trp, Lys, Ser, His, Pro, or Val;
Xaa at position 50 is Ala, A sn, Pro, Ser, or Lys,
Xaa at position 51 is Val, Thr, Pro, His, Lieu, Phe, or Ser;
Xaa at position 52 is Lys, Ile, Arg, Val, Asn, Glu, or Ser;
Xaa at position 53 is Ser, Ala, Phe, Val, aly, Asn, Ile, Pro, or His;
Xaa at position 54 is Leu, Val, Trp, Ser, Ile, Phe, Thr, or His;
Xaa at position 55 is Gln, Ala, Pro, Tir, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp. Leu, Ser, Gly, Thr, or Arg;
Xaa at position 60 is Ile, Met, Thr, Pro, Arg, Gly, Ala;
Xaa at position 61 is Glu, Lys, Gly, Asp. Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Clu, Phe, Gly, or Arg;
Xaa at position 65 is Lys, Thr, Cly, Asn, Met, Arg, Ile, or Asp;
Xaa at position 66 is Asa, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp. Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, A zn, Val, or Gln;
Xaa at position 72 is Pro, Cys, Atg, Ala, or Lys;
Xaa at position 73 is Leu, Sert Trp, or Gly;
Xaa at position 74 is Ala, Lys, Arg, Val, or Trp;
Xaa at position 75 is Thr, Asp. Cys, Leu, Val, Glu, His, Asn, or Ser;
Xaa at position 76 is Ala , Pro, Ser, Thr, Gly, Asp. Ile, or Met;
Xaa at position 77 is Ala, Pro, Ser, Thr, Phe, Leu, Asp. or His;
Xaa at position 78 is Pro, Phe, Arg, Ser, Lys, His, Ala, Gly, Ile or Leu;
Xaa at position 79 is Thr, Asp. Ser, Asn, Pro, Ala, Leu, or Arg;

Xaa at position 80 is Arg, Ile,Ser, GLu, Lieu, Val, Gln, Lys, His, Ala or Pro;

Xaa at position 81 is His, Gla, Pro, Arg, Val, Leu, Gly, Thr, Asn, Lys. Ser, Ala, Trp, Phe, Ile or Tyr;
Xaa at position 82 is Pro, Lys, Tyr, Gly, Ile, or Th;

Xaa at position 83 is Ile, Val, Lys, Ala, or Asn;

Xaa at position 84 is His, Ile, Asn. Leut, Asp. Ala, Thr, Glu, GIn, Ser, Phe, Met, Val, Lys, Arg, Tyr or Pro;

Xaa at position 85 is Ile, Leu, Arg, Asp. Val, Pro, GIl, Gly, Ser, Phe, or His;

Xaa at position 8 9 is Lys. Tyr, Leu, His, Arg, Ile, Ser, Gln, Pro;
Xaa at position 87 is Asp;
Xaa at position 88 is Gly, Leu, Glu, Lys, Ser, Tyr, or Pro;
Xaa at position 89 is Asp. or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe. Ser, Trp, Gln, Tyr, Leu, Lys, Ile, Asp. or His;
Xaa at position 92 is Glu, Ser, Ala, Lys, Thr, Ile, Gly, or Pro;
Xaa at position 94 is Arg, Lys, Asp. Leu, Thr, Ile, Gln, His, ser, Ala, or Pro;
Xaa at position 95 is Arg, Thr, Pro, Glu, tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp. or Met;
Xaa at position 98 is Thr, Val. Gln, Tyr, Glu, His, ser, or Phe;
Xaa at position 99 is Phe, Ser, Cys, His, Gly, Trp, Tyr, Asp. Lys, Leu, Ile, Val or Asn;
Xaa at position 100 is Tyr, Cys, His, Ser, Trp, Arg, . or Leu;
Xaa at position 101 is Le u, Asn, Val, Pro, Arg, Ala, His, Thr, Trp, or Met;
Xaa at position 102 is Lys;
Xaa at position 103 is Thr, Ser, Asn, Il e, Trp, Lys, or Pro;
Xaa at position 104 is Leu, Ser, Pro, Ala, Glu, Cys, Asp. or Tyr;
Xaa at position 105 is Glu, Ser, Lys, Pro, Le u, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp. or Gly;
Xaa at position 108 is Gln. Ser. Met, Trp, Arg, Phe, Pro, His, Ile, Tyr, or Cys;
Xaa at position 109 is Ala, Met, Glu, His, Ser, Pro, Tyr, or Leu;

wherein from 1 to 3 of the amino acids designated by Xaa are different from the corresponding native amino acids of (1–133) human interleukin-3; said human interleukin-3 mutant polypeptide having at least three times greater cell proliferative activity than native human interleukin-3, in at least one assay selected from the group consisting of: AML cell proliferation, TF-1 cell proliferation and Methylcellulose assay; and a factor which is a colony stimulating factor, a cytokine, a lymphokine, an interleukin, or a hematopoietic growth factor.

7. A composition comprising a mutant human interleukin-3 polypeptide comprising a modified interleukin-3 amino acid sequence selected from the group consisting of:

(a) an amino acid sequence of SEQ ID NO:4; and (b) an N-terminal Met residue, Ala residue, or Met-Ala dipeptide joined to an amino acid sequence according to (a), wherein Xaa at position 3 is Ser, Lys, Gly, Asp. Met, Olr, or Arg;

Xaa at position 4 is Ann, His, Leu, II G, Phe, Arg, or Gln;

Xaa at position 5 is Met, Phe, Ile, Arg, Gly . Ala, or Cys;

Xaa at position 6 is Ile, Cys, Oln, Clu, Arg, Pro, or Ala;

Xaa at position 7 is Asp. Phe, Lys, Arg, Ala, Gly, Glu, Gln, Asn, Thr, Ser or Val;

Xaa at position 8 is Glu, Trp, Pro, Ser, Ala, His, Asp. Asn, C iln, Leu, Val, or Gly;

Xaa at position 9 is Ile, Val, Ala, Le e, Gly, Trp, Lys, Phe, Ser. or Arg;

Xaa at position 10 is lle, Gly, Val, Arg, Ser, Phe, or Leu;

Xaa at position 11 is Thr, His, Gly, Gln, Arg, Pro, or Ala;

Xaa at position 12 is His, Thr, Phe, Gly, Arg, Ala, or Trp;

Xaa at position 13 is Leu, Gly, Arg, Thr, ser, or Ala i

Xaa at position 14 is Lys, Arg, Leu, Gln, GlYr Pro, Val or Trp;

Xaa at position 15 is Gln, Asn, Leu, Pro, Arg, or Val;

Xaa at position 16 is Pro, His, Thr, Gly, Asp. Cln, Ser, Leu, or Lys;

Xaa at position 17 is Pro, Asp. Gly, Ala, Arg, Leu, or Gln;

Xaa at position 18 is Leu, Val, Arg, Gln, Asn, Gly, Ala, or Giu;

Xaa at position 19 is Pro, Leu, Gln, Ala, Thrr or Glu;

Xaa at position 20 is Leu, Val, Gly, Ser, Lys, Glu, Gln, Thr, Arg, Ala, Phe, Ile or Met;

Xaa at position 21 is Leu, Ala, Gly, Asn, Pro, Gln, or Val;

Xaa at position 22 is Asp. Leu, or Val;

Xaa at position 23 is Phe, ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp. Ser, Cys, Ala, Lys, Asn, Thr, LeU, Val, Glu, Phe, Tyr, Ile or Met;

Xaa at position 29 is Glu, Asn, Tyr, Leu, Phe, Asp. Ala, Cys, Gln, Arg, Thr, Gly or Ser;

Xaa at position 30 is Asp. Ser, Leu, Arg, Lys, Thr, Met, Trp, Glu, Asn, Gln, Ala or Pro;

Xaa at position 31 is Gln, Pro, Phe, Val, Met, Leu, Thr, Lys, Asp. Asn, Arg, Ser, Ala, Ile, Glu, His or Trp;

Xaa at position 32 is Asp. Phe, Ser, Thr, Cys, Glu, Asn, Gln, Lys, His, Ala, Tyr, Ile, Val or sly:

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 3S is Met, Arg, Ala, Gly, Pro, Asn, His, or Asp;

Xaa at position 36 is Glu, Leu, Thr, Asp. Tyr, Lys, Asn, Ser, Ala, Ile, Val, His, Phe, Met or G in:

Xaa at position 37 is Asn, Arg, Met, Pro, Ser, Th v, or His;

Xaa at position 38 is Ash, His, Arg, Leu, Gly, Ser, or Thr;

Xaa at position 39 is Leu, Thr, Ala, Gly, Glu, Pro, Lys, Ser, or Met;

Xaa at position 40 is Arg, Asp. Ile, Ser, Val, Thr, Gln, Asn, Lys, His, Ala or Leu:

Xaa at position 41 is Arg, Thr, Val, Ser, Le u, or Gly;

Xaa at position 42 is Pro, Gly, Cys, Ser, Gln, Glu, Arg, His, Thr, Ala, Tyr, Phe, Leu, Val or Lys;

Xaa at position 43 is Asn or Gly;

Xaa at position 44 is Leu, Ser, Asp. Arg, Gln, Val, or Cys;

Xaa at position 45 is Glu, Tyr, His, Leu, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa At position 48 is Asn, His, Val, Arg, Pro, Thr, Asp. or Ile;

Xaa at position 49 is Arg, Tyr, rrp, Lys, Ser, iris, Pro, or Val;

Xaa at position 50 is Ala, Asn, Pro, Ser or Lys;

Xaa at position 51 is Val, Thr, Pro, His, Leu, Phe, or Ser;

Xaa at position 52 is Lys, Ile, Arg, Val, Asn, Glu, or Ser;

Xaa at position 53 is Ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Thr, Glu, Arg, Trp, Gly, or Leu;

Xaa at position 56 is Asn, Leu, Val, Trp, Pro, or Ala;

Xaa at position 57 is Ala, Met, Leu, Pro, Arg, lu, Thr, Gln, Trp, or Asn;

Xaa at position 58 is Ser, Glu, Met, Ala, His, Asn, Arg, or Asp;

Xaa at position 59 is Ala, Gln, Asp. Leu, Set, Gly, Thr, or Arg;

Xaa at position 60 is Ile, Met, Thr, Pro, Arg, Gly, Ala;

Xaa at position 61 is Glu, Lys, Gly, Asp. Pro, Trp, Arg, Ser, Gln, or Leu;

Xaa at position 62 is Ser, Val, Ala, Asn, Trp, Glu, Pro, Gly, or Asp;

Xaa at position 63 is Ile, Ser, Arg, T h ir. or Leun

Xaa at position 64 is Leu, Ala, Ser, Glu, Phe, sly, or Arg,

Xaa at position 65 is Lys, Thr, G sly, Asn, Met, Arg, Ile, or Asp;

Xaa at position 66 is Asn, Trp, $V_4 1$, Gly, Thr, Leu, Glu, or Arg;

Xaa at position 67 is Leu, Gln, Gly, Ala, Trp, Arg, Val, or Lys;

Xaa at position 68 is Leu, Gln, Lys, llrp, Arg, Asp. Glu, Asn, His, Thr, Ser, Ala, Tyr, Phe, Ile, Met or Val;

Xaa at position 69 is Pro, Ala, Thr, Trp, Arg, or Met;

Xaa at position 70 is Cys, Glu, Gly, Arg, Met, or Val;

Xaa at position 71 is Leu, Asn, Val, or Gln:

Xaa at position 72 is Pro, Cys, Arg, Ala, or Lys;

Xaa at position 73 is Leu, Ser, Trp. or Gly;

Xaa at position 74 is Ala, Lys, Arg, Val, or Trp;

Xaa at position 75 is Thr, Asp. Cys, Leu, Val, Gl m, His, Asn, or Ser,

Xaa at position i6 is Ala, Pro, Ser, Thr, Gly, Asp. Ile, or Met;

Xaa at position 77 is Ala, Pro, Ser, Thr, Phe, Leu, Asp. or His;

Xaa at position 78 is Pro, Phe, Arg, Ser, Lys, His, Ala, Gly, Ile or Leu;

Xaa at position 79 is Thr, Asp. Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Tyr;

Xaa at position 82 is Pro, Lys. Tyr, Gly, Ile, or Thr;

Xaa at position 83 is Ile, Val, Lys, Ala, or Asti;

Xaa at position 84 is His, Ile, Asn, Leu, Asp. Ala, Thr, Glu, Gl in Ser, Phe, Met, Val, Lys. Arg, Tyr or Pro;

Xaa at position 85 is Ile, Leu, Arg, Asp. Val, Pro, Gln, Gly, Ser, Phe, or His;

Xaa at position 86 is Lys, Tyr, Leu, His, Arg, Ile, Ser, Gln, Pro;

Xaa at position 87 is Asp;

Xaa at position 88 is Gly, Leu, G iu, Lys, Ser, Tyr, or Pro;

Xaa at position 89 is Asp. or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp. or His;

Xaa at position 92 is Glu, Ser, Ala, Lys, Thr, Ile, Gly, or Pro;

Xaa at position 94 is Arg, Lys, Asp. Leu, Thr, Ile, Gln, His, Ser, Ala, or Pro;

Xaa at position 95 i B Arg, Thr, Pro, Glu, Tyr, L au, Ser, or Gly;

Xaa at position 96 is Lys, Asn, Thr, Leu, Gln, Arg, His, Glu, Ser. Ala or Trp;

Xaa at position 97 is Leu, Ile, Arg, Asp. or Met;

Xaa at position 98 is Thr, Val, Gln, Tyr, Clu, His, Ser. or Phe;

Xaa at position 99 is Phe, Ser, Cys, His, Gly, Trp, Tyr, Asp. Lys, Leu, Ile, Val or Asn;

Xaa at position 100 is Tyr, Cys, His, Ser, Trp. Arg, or Leu;

Xaa at position 101 is Leu, Asn, Val, Pro, Arg, Ala, His, Thr, Trp, or Met;

Xaa at position 102 is Lys,

Xaa at position 103 is Thr, Ser, Asn. Ile, Trp, Lye, or Pro;

Xaa at position 104 is Leu, Ser, Pro, Ala, Glu, Cys, Asp. or Tyr;

Xaa at position 105 is GlU, Ser, Lys, Pro, Leu, Thr, Tyr, or Arg;

Xaa at position 106 is Asn, Ala, Pro, Leu, His . Val, or Oln:

Xaa at position 107 is Ala, Ser, Ile, Asn, Pro, Lys, Asp. or Gly;

Xaa at position 108 is Gln, Ser, Met, Trp, Arg, Phe, Pro, His, Ile, Tyr, or Cys;

Xaa at position 109 is Ala, Met, Glu, His, Ser. Pro, Tyr, or Leu;

wherein from 1 to 3 of the amino acids designated by Xaa are different from the corresponding native amino acids of (1–133) human interleukin-3; said human interleukin-3 mutant polypeptide having at least three times greater cell proliferative activity than native human interleukin-3, in at least one assay selected from the group consisting of: AML cell proliferation, TF-l cell proliferation and Methylcellulose assay; and a factor selected from the group consisting of: GM-CSF, CSF -1, G-CSF, G-CSF ($Ser^{17}$), M-CSF, erythropoietin (EPO), IL-1, IL-4, IL-2, IL-5, IL-6, IL-7, IL-8, IL-9, IL-10, IL-11, IL-12, IL-13, LIF, flt3/flk2 ligand, human growth hormone, B-cell growth factor, B-cell differentiation factor, eosinophil differentiation factor and stem cell factor (SCF).

8. The composition according to claim 7, wherein said modified interleukin-3 amino acid sequence is selected from the group consisting of:

(a) an amino acid sequence of SEQ ID NO;5

(b) an N-terminal Met residue, Ala residue, or Met-Ala dipeptide joined to an amino acid sequence according to (a), wherein Xaa at position 3 is Ser, Gly, Asp. Met, or Gln;

Xaa at position 4 is Asn, His, or Ile;

Xaa at position 5 is Met or Ile;

Xaa at position 7 is Asp or Glu;

Xaa at position 9 is Ile, Ala, Leu, or Gly;

Xaa at position 10 is Ile, Val, or Leu ;

Xaa at position 11 is Thr, His, Gln, or Ala;

Xaa at position 12 is His or Ala;

Xaa at position 15 is Gln, Asn, or Val;

Xaa at position 16 is Pro, Gly, or Glu;

Xaa at position 17 is Pro, Asp. Gly, or Gln;

Xaa at position 18 is Leu, Arg, Gin. Asn, Gly, Ala, or Clu;

Xaa at position 19 is Pro or Glu;

Xaa at position 20 is Let, Val, Gly, Ser, Lys, Ala, Arg, Gln, Glu, Ile, Phe, Thr or Met;

Xaa at position 21 is Leu, Ala, Asn, Pro, Glt, or Val;

Xaa at position 23 is Phe, Ser, Pro, or Trp;

Xaa at position 24 is Asn or Ala;

Xaa at position 28 is Gly, Asp. Ser, Cys, Ala, Asn, Ile, Leu, Met Tyr or Arg;

Xaa at position 30 is Asp or Glu;

Xaa at position 31 is Gln, Val, Met, Leu, Thr, Ala, Aso, Glu, Ser or Lys;

Xaa at position 32 is Asp. Phe, Ser, Thr, Ala, As h, Gln, Glu, His, Ile, Lys. Tyr, Val or Cys;

Xaa at position 36 is Glu, Ala, Asn, Ser or Asp;

Xaa at position 37 is Asn, Arg, Met, Pro, Ser, Thr, or His;

Xaa at position 40 is Arg or Ala;

Xaa at position 41 is Arg, Thr, Val, Leu, or Gly;

Xaa at position 42 is Pro, Gly, Ser, Gln, Ala, Arg, Asn, Glu, Leu, Thr, Val or Lys;

Xaa at position 46 is Ala or Ser;

Xaa at position 48 is Asn, Pro, Thr, or Ile;

Xaa at position 49 is Arg or Lys;

Xaa at position 50 is Ala or Asn;

Xaa at position 51 is Val or Thr;

Xaa at position 52 is Lys or Arg;

Xaa at position 53 is Ser, Phe, or His;

Xaa at position 54 is Leu, Ile, Phe, or His;

Xaa at position 55 is Gln. Ala, Pror Thr, Clu, Arg, or Gly;

Xaa at position 57 is Ala, Pro, or Arg;

Xaa at position 58 is Ser. Glu, Arg, or Asp;

Xaa at position 59 is Ala or Leu;

Xaa at position 62 is Ser, Val, Ala, Asn, Glu, Pro, or Gly;

Xaa at position 63 is Ile or Leu;

Xaa at position 65 is Lys, Thrt Gly, Asn, Met, Arg, Ile, or Asp;

Xaa at position 66 is Asn, Gly, Glu, or Arg,; Zaa at position 68 is Leu, Gln, Trp, Arg, Asp. Ala, Asn, Glu, His;

Ile, Met. Phe, Ser, Thr, Tyr or Val,

Xaa at position 59 is Pro or Thr;

Xaa at position 71 is Leu or Val;

Xaa at position 73 is Leu or Ser;
Xaa at position 74 is Ala or Trp;
Xaa at position 77 is Ala or Pro;
Xaa at position 79 is Thr, Asp. Ser, Pro, Ala, Leu, or Arg;
Xaa at position 81 is His, Pro, Arg, Val, Leu, Cly, Asn, Phe, Ser or Thr;
Xaa at position 82 is Pro or Tyr:
Xaa at position 83 is Ile or Val;
Xaa at position 84 is His, Ile, Asn, Leu, Ala, Thr, Arg, Gln, Lys, Met, Ser, Tyr, Val or Pro,
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Len;
Xaa at position 91 is Asn, Pro, Ala, Ser, Trp, Gln, Tyr, Leu, Lys, Ile, Asp. or His;
Xaa at position 92 is Glu, or Gly;
Xaa at position 94 is Arg, Ala, or Ser;
Xaa at position 95 is Arg, Thr Glu, Le, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Setr;
Xaa at position 106 is Asn, Pro,l Leu, Hills, Val, or Gly;
Xaa at position 107 is Ala, Ser. Ile, Asn, Pro, Asp. or Gly;
Xaa at position 108 is Gln, Ser, Met, Trp, Arg, Phe, Pro, His, Ile, Tyr, or Cys;
Xaa at position 109 is Ala, Met, iGlu, His, Ser, Pro, T hyr, or Lue, u;
wherein from 1 to 3 of the amino acid designated by Xaa are different from the corresponding L mino acids of native human interleukin-3.

9. The composition according to claim 7, wherein said modified interleukin-3, amino iacid sequence is selected from the group consisting of;
   (a) an amino acid sequence of SEQ ID NO:6; and
   (b) an N-terminal Met residue, Ala residue, or Met-Ala dipeptide joined to an amino acid sequence according to (a),
wherein
   Xaa at position 3 is Ser, Gly, As p, or Gln;
   Xaa at position 4 is Asn, His, or Ile;
   Xaa at position 9 is Ile, Ala, Leu, or Gly;
   Xaa at position 11 is Thr, His, or Glnr;
   Xaa at position 12 is His or Ala;
   Xaa at position 15 is Gln or Asn;
   Xaa at position 16 is Pro or Gly;
   Xaa at position 18 is Leu, Arg, Asn, or Ala;
   Xaa at position 20 is Leu, Val, Ser, Ala, Arg, Gln, Glu, Ile, Phe, Thr or Met;
   Xaa at position 21 is Leu, Ala, Asn, or Pro;
   Xaa at position 24 is Asn or Ala;
   Xaa at position 28 is Gly, Asp. Ser, Ala, Asn, Ile, Leu, Met, Tyr or Arg;
   Xaa at position 31 is Gln, Val, Met, Leu, Ala, Asn, Glu or Lys;
   Xaa at position 32 is Asp. Phe, Ser, Ala, Gln, Glu, His, Val or Thr;
   Xaa at position 36 is Glu, Asn, Ser or Asp;
   Xaa at position 37 is Asn, Arg, Pro, Thr, or His;
   Xaa at position 41 is Arg, Leu, or Gly;
   Xaa at position 42 is Pro, Gly, Ser, Ala, Asn, Val, Leu or Gln;
   Xaa at position 48 is Asn, Pro, or Thr;
   Xaa at position 50 is Ala or Asn;
   Xaa at position 51 is Val or Thr;
   Xaa at position 53 is Ser or Phe;
   Xaa at position 54 is Leu or Phe;
   Xaa at position 55 is Gln, Ala, Glu, or Arg;
   Xaa at position 62 is Ser, Val, Asn, Pro, or Gly;
   Xaa at position 63 is Ile or Leu;
   Xaa at position 65 is Lys, Asn, Met, Arg, Ile, or Gly;
   Xaa at position 66 is Asn, Gly, Glu, or Arg;
   Xaa at position 68 is Leu, Gln, Trp, Arg, Asp. Asn, Glu, His, Met, Phe, Ser, Thr, Tyr or Val;
   Xaa at position 73 is Leu or Ser;
   Xaa at position 74 is Ala or Trp;
   Xaa at position 77 is Ala or Pro;
   Xaa at position 79 is Thr, Asp. or Ala;
   Xaa at position 81 is His, Pro, Arg, Val, Gly, Asn, Ser or Thr;
   Xaa at position 84 is His, Ile, Asn, Ala, Thr, Arg, Gln, Glu, Lys, Met, Ser, Tyr, Val or Leu;
   Xaa at position 85 is Ile ox Leu;
   Xaa at position 86 is Lys or Arg;
   Xaa at position 87 is Asp;
   Xaa at position 91 is Asn, Pro, Ser, Ile or Asp;
   Xaa at position 94 is Arg, Ala, or Ser;
   Xaa at position 95 is Arg, Thr, Glu, Leu, or Ser;
   Xaa at position 98 is Thr or Gln;
   Xaa at position 102 is Lys;
   Xaa at position 103 is Thr, Ala, His, Phe, Tyr or Ser;
   Xaa at position 106 is Asn, Pro, Leu, His, Val, or Gln;
   Xaa at position 107 is Ala, Ser, Ile, Pro, or Asp;
   Xaa at position 108 is Gln, Met, Trp, Phe, Pro, His, Ile, or Tyr;
   Xaa at position 109 is Ala, Met, Glu, Ser, or Leu;
wherein from 1 to 3 of the amino acids designated by Xaa are different from the corresponding amino acids of native (1–133) human interleukin-3.

10. The composition according to claim 7, wherein said modified interleukin-3 amino acid se qluence is selected from the group consisting of:
   (a) an amino acid sequence of SEQ ID NO:8; and
   (b) an N-terminal Met residue, Ala residue, or Met-Ala dipeptide joined to an amino acid sequence according to (a),
wherein;
   Xaa at position 4 is Asn or Ile;
   Xaa at position 5 is Met, Ala or Ile;
   Xaa at position 6 is lie, Pro or Leu;
   Xaa at position 9 is Ile. Ala or Leu;
   Xaa at position 11 is Thr or His;
   Xaa at position 15 is Gln, Arg, Val or Leu;
   Xaa at position 18 is Leu, Ala, A zn or Argr;
   Xaa at position 20 is Leu or ser;
   Xaa at position 23 is Phe, Pro, or Ser;

Xaa at position 24 is Asn or Ala;
Xaa at position 28 is Gly, Ala, Ser, Asp or Asn;
Xaa at position 31 is Gln, Val, or Met;
Xaa at position 32 is Asp or Ser;
Xaa at position 35 is Met, Ile or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn. Val or Pro;
Xaa at position 49 is Arg or His;
Xaa at position 51 is Val or Ser;
Xaa at position 53 is Ser, Asn, His or Cly;
Xaa at position SS is Gln or Glu;
Xaa at position 59 is Ala or Gly;
Xaa at position 62 is Ser, Ala or Pro,
Xaa at position 65 is Lys, Arg or Ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro,
Xaa at position 79 is Pro or Ser;
Xaa at position 81 is His or Thr;
Xaa at position 84 is His, Ile, or Thr;
Xaa at position 86 is Lys or Arg:
Xaa at position 87 is Asp. Ala or Met:
Xaa at position 91 is Asn or Gln;
Xaa at position 95 is Arg, Glu, Leu;
Xaa at position 98 is Thr or Gln;
Xaa at position 102 is Lys, Val, Trp or Ser;
Xaa at position 103 is Thr or Ser;
Xaa at position 106 is Asn, Gln, or His;
Xaa at position 109 is Ala or Glu;
wherein from one to three of the amino acids designated by Xaa are different from the corresponding amino acids of native (1–133) human interleukin-3.

11. A composition consisting of; a mutant human interleukin-3 (hIL-3) polypeptide having a modified hIL-3 amino acid sequence selected from the group consisting of:

(a) an amino acid sequence of SEQ ID NO:1
(b) an N-terminal Met residue, Ala residue, or Met-Ala dipeptide joined to an amino acid sequence according to (a), wherein
Xaa at position 17 is Ser, Lys, Gly, Asp. Met, Gln, or Arg;
Xaa at position 18 is Asn, His. Leu, Ile, Phe, Arg, or Gln;
Xaa at position 19 is Met, Phe, Ile, Arg, Gly, Ala, or Cys;
Xaa at position 20 is Ile, Cys, Gln, Clu, Arg, Pro, or Ala;
Xaa at position 21 is Asp. Phe, Lys, Arg, Ala, Gly, Giu, Gln, Asn, Thr, Ser or Val;
Xaa at position 22 is G iu, Trp, Pro, Ser, Ala, His, Asp. As h, Gln, Leu, Val or Gly;
Xaa at position 23 is Ile, Val, Ala, Leu, Cly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His. Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val,
Xaa at position 30 is Pro, His, Thr, Gly, Asp. Gln, Ser, Leu, or Lys;
Xaa at position 31 is Pro, Asp. Gly, Ala, Arg, Leu, or Gln;
Xaa at position 32 is Leu, Val, Arg, Gln, Asn, G . y, Ala, or Glu;
Xaa at position 33 is Pro, Leu, Gln, Ala, Thr, or Glu;
Xaa at position 34 is Leu, Val, Gly, Ser, Ly y, G iu, Gln, Thr, Arg, Ala, Phe, Ile or Met;
Xaa at position 35 is Leu, Ala, Gly, Asn, Pro, GirL. or Val;
Xaa at position 36 is Asp. Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp. Ser, Cys, Asn, Lys, Try, Leu, Val, Gilu, Phe, Tyr, Ile, Met or Ala;
Xaa at position 43 is Glu, Asn, Tyr, Len, Phe, Asp. Ala, Cys, Gln, Arg, Thr, Gly or Ser;
Xaa at position 44 is Asp. Ser, Le u, Arg, Lys, Thr, Met, Trp, Glu, Asn, Gln, Ala or Pro;
Xaa at position 45 is Gli, Pro, Phe, Val, Met. Leu, Thr, Lys, Trp, Asp. Asn, Arg, Ser, Ala, Ile, Glu or His;
Xaa at position 46 is Asp. Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Len, Ser, Cys, Ar-g, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Le u, Thr, Asp. Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp. Ile, Ser, Val, Thr, Gln, Asn, Lys, His, Ala or Le u;
Xaa at position 55 is Arg, Thr, Val, Ser, Leu, or Gly;
Xaa at position 56 is Pro, Gly, Cys, Ser, Gln, Glu, Arg, , His, Thr, Ala, Tyr, Phe, Leu, Val or Lys;
Xaa at position 57 is Asn or Gly;
Xaa at position 58 is Leu, Ser, Asp. Arg, Gln, Val, or Cys;
Xaa at position 59 is Gl, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp. or Ile;
Xaa at position 63 is Arg, Tyr, Trp, Lys, Ser, Ilis, Pro, or Val;
Xaa at position 64 is Ala, Asn, Pro, Ser, or Lys;
Xaa at position 65 is Val, Thr, Pro, Ris . Leu, Phe, or Ser;
Xaa at position 66 is Lys, Ile, Arg, Val, Asn, Glu, or S cr;

Xaa at position 67 is Ser, Ala, Phe, Val, Gly. Asri, Ile, Pro, or His:

Xaa at position 68 is Leu, Val, Trp, Ser, Ile, Phe, Thr, or His;

Xaa at position 69 is Gln, Ala, Pro, Thr, Glu, Arg, Trp, Gly, or Leu;

Xaa at position 70 is Asn, Len, Val, Trp, Pro, or Ala;

Xaa at position 71 is Ala, Met, Leu, Pro, Arg, Glu, Thr, Gln, Trp , or Asn;

Xaa at position 72 is Ser, Glu, Met, Ala, His, Asn, Arg, or Asp;

Xaa at position 73 is Ala, Glun Asp. Leu, Ser, Gly, Thr, or Arg;

Xaa at position 74 is Ile, Met, Thr, Pro, Arg, Gly, Ala;

Xaa at position 75 is Glu, Lys, Gly . Asp. Pro, Trp, Arg, Ser, Gln, or Leu;

Xaa at position 76 is Ser, Val, Ala, Asn, Trp, Glu, Pro, Gly, or Asp;

Xaa at position 71 is Ile, Ser, Arg, Thr, or Leu;

Xaa at position 78 is Leu, Ala, Ser, Glu, Phe, Gly, or Arg;

Xaa at position 79 is Lys, Thr, Asn, Met. Arg, Ile, Gly, or Asp;

Xaa at position 80 is Asn, Trp, Val, Gly, Thr, Leu, Glu, or Arg;

Xaa at position 81 is Len, Gln, dly, Ala, Trp, Arg, Val, or Lys;

Xaa at position 82 is Leu, Gln, Lys, Trp, Arg, Asp. Glu, Asn, His, Thr, Ser, Ala, Tyr, Phe, Ile, Met or Val;

Xaa at position 83 is Pro, Ala, Thr, Trp, Arg, or Met;

Xaa at position 84 is Cys, Glu, Gly, Arg, Met, or Val;

Xaa at position 85 is Leu, Asn, Val, or Gln;

Xaa at position 86 is Pro, Cys, Arg, Ala, or Lys;

Xaa at position 87 is Leu, Ser, Trp, or Gly;

Xaa at position 88 is Ala, Lys, Arg, Val, or Trp;

Xaa at position 89 is Thr, ASp, Cys, Leu, Val, Glu, His, Asn, or Ser;

Xaa at position 90 is Ala, Pro, Ser, Thr, Gly, Asp. Ile, or Met;

Xaa at position 91 is Ala, Pro, Ser, Thr, Phe, Leu, Asp. or His;

Xaa at position 92 is Pro, Phe, Arg, Ser, Lys, His, Ala, Gly, Ile or Len;

Xaa at position 93 is rrhr, Asp. Ser, Asn, Pro, Ala, Leu, or Arg;

Xaa at position 94 is Arg, Ile, Ser, Gnu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or yr;

Xaa at position 96 is Pro, Ly z, Tyr, Gly, Ile, or Thr;

Xaa at position 97 is Ile, Val, Lys, Ala, or Asn;

Xaa at position 98 is His, Ile, Asn, Leu, Asp. Ala, Thr, Glu, Gln, Ser, Phe, Met, Val, Lys, Arg, Tyr or Pro;

Xaa at position 99 is Ile, Leu, Arg, Asp. Val, Pro, Gln, Gly, Ser, Phe, or His;

Xaa at position 10D is Lys, Tyr, Leu, His, Arg, Ile, Ser, Gln, or Pro;

Xaa at position 101 is Asp;

Xaa at position 102 is Gly, Le u, Glu, Lys, Ser, Tyr, or Pro;

Xaa at position 103 is Asp. or Ser;

Xaa at position 104 is Trp, Val, Cys, Tyr, Thr, Met, Pro, Leu, Gln, Lys, Ala, Phe, or Gly;

Xaa at position 105 is As s, Pro, Ala, Phe, Ser, Trp, Gln, Tlr, Leu, Lys, Ile, Asp. or His;

Xaa at position 106 is Glu, Ser, Al a, Ly z, Thr, Ile, Gly, or Pro;

Xaa at position 108 is Arg, Lys, Asp. Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp. or Met;

Xaa at position 112 is Thr, Val, rln, Tyr, lu, His, Ser, or Phe;

Xaa at position 113 is Phe, Ser, Cys, His, Gly, Trp, Tyr, Asp. Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met:

Xaa at position 116 is Lys;

Xaa at position 117 is Thr, Ser, Asn, Ile, Trp, Lys, or Pro;

Xaa at position 118 is LeU, Ser f Pro, Ala, Glu, Cys, Asp. or Tyr;

Xaa at position 119 is Glu, Ser, Lys, Pro, Leu, Thr, Tyr, or Arg;

Xaa at position 120 is Asn, Ala, Pro, Leu, His, Val, or rln;

Xaa at position 121 is Ala, Ser, Ile, Ann, Pro, Lys, Asp. or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 1 to 3 of the amino acids designated by Xaa are different from the corresponding amino acids of native (1–133) human interleukin-3; wherein from 1 to 14 amino acids can optionally be deleted from the N-terminus and/or from 1 to 15 amino acids can optionally be deleted from the C-terminus of said modified hIL-3 amino acid sequence; said human interleukin-3 mutant polypeptide having at least three times greater cell proliferative activity than native human interleukin-3, in at least one assay selected from the group consisting of: AML cell proliferation, TF-1 cell proliferation and Methyicellulose assay; and a factor which is a colony stimulating factor, a cytokine, a lymphokine, an interleukin, or a hematopoietic growth factor.

12. A composition consisting of a mutant humnan interleukin-3 (hIL-3) polypeptide having a modified hIL-3 am ino acid sequence selected from the group consisting of:

(a) a n amino acid sequence of SEQ ID NO:1

(b) an N-terminal Met residue, Ala residue, or Met-Ala dipeptide joined to an amino acid sequence according to (a), wherein Xaa at position 17 is Ser, Lys, Ply, Asp , Met, Gln, or Arg;

Xaa at position 18 is Asn, His, Leu, Ile, Phe, Ar p, or Gln;

Xaa at position 19 is Met, Phe, Il e, Arg, Sry, Ala, or Cys;

Xaa at position 20 is Ile, Cys, Gln, Gl, Arg, Pro, or Ala;

Xaa at position 21 is Asp. Phe, Lys, Arg, Ala, Aly, Glo, Gln, Asn, Thr, Ser or Val;

Xaa at position 22 is GL i, Trp, Pro, Se G, Ala, His, Asp. Asn, Gln, Leu, Val or Gly;

Xaa at position 23 is Ile, Val, Ala, Leu, Gly, Trp, Lys, Phe, Ser, or Arg;

Xaa at position 24 is Ile, Gly, Val, Arg, Ser, Phe, or Len;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Vly, Arg, Thr, Set, or A la;
Xaa at position 28 is Lys . rg, Le a, Gln, Gly, Pro, Val or Trp;
Xaa at position 29 is Gln, Asn, Leu, Pro, Arg, or Val;
Xaa at position 30 is Pro, His, Thr, Gly, Asp. Gln, ser, Len, or Lys;
Xaa at position 31 is Pro, Asp. Gly, Ala, Arg, Le a, or Gln;
Xaa at position 32 is Leu, Val, Arg, Gln, Asn, Gy, Ala, or Glu;
Xaa at position 33 is Pro, Leti, Gln, Ala, Thr, or Gln;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp. Leu, or Val;
Xaa at position 37 is Phe, Ser, Pro, Trp, or Ile;
Xaa at position 38 is As g, or Ala;
Xaa at position 40 is Len, Trp, or Arg;
Xaa at position 41 is Asn, Cys, Arg, Len, His, Met, or Pro;
Xaa at position 42 is Gly, Asp. Ser, Cys, Asn, Lys, Thr, Leu, Val, Glu, Phe, Tyr. Ile, Met or Ala;
Xaa at position 43 is Glu, Asn, Tyr, Leu, Phe. Asp. Ala, Cys, Gln, Arg, Thr, Gly or Ser;
Xaa at position 44 is Asp. Ser, Leu, Arg, Lys, Thr, Met, Trp, Glu, Asn, Gln, Ala or Pro;
Xaa at position 45 is Gln. Pro, Phe, Val, Met, Leu, Thr, Lys, Trp, Asp. Asn, Arg, Ser, Ala, lie, Glu or His;
Xaa at position 46 is Asp. Phe, Ser, Tht, Cys, Glu, Asn, Gln, Lys, His, Ala, Tyr, Ile, Val or Gly;
Xaa at position 47 is Ile, Gly, Val, Ser, Arg, Pro , or His;
Xaa at position 48 is Leu, Ser, Cys, Arg, Ile, His, Phe, Glu, Lys, Thr, Ala, Met. Val or Asn;
Xaa at position 49 is Met, Arg, Ala, Gly, Pro, Asn, His, or Asp;
Xaa at position 50 is Glu, Leu, Thr, Asp. Tyr, Lys. Asn, Ser, Ala, Ile, Val, His, Phe, Met or Gln,
Xaa at position 51 is Asn, Arg, Met, Pro, Ser, Thr, or His;
Xaa at position 52 is Asri, His, Arg, Leu, C Gly, Ser. or Thr;
Xaa at position 53 is Leu, Thr, Ala, Gly, Glu, Pro, Lys, Ser, or Met;
Xaa at position 54 is Arg, Asp. Ile, Ser, Val, Thr, Gln, Asn, Lys, His p Ala or Leu;
Xaa at position 55 is Arg, Thr, Val, Ser, Leu, or Gly; X Za at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp. Arg, Gln. Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glur Pro, Lys, Arg, or Ser;
Xaa at position 62 is Asn. His, Val, Arg, Pro, Thr, Asp. or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu. or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, G iu, Thr, Gln, Trp, or Asn;
Xaa at position 72 is Ser, Glu, Met, Ala, His, Asn, Arg, . or Asp;
Xaa at position 73 is Ala, Glu, Asp. Leu, Ser, Gly, Thr, or Arg;
Xaa at position 74 is Ile, Met, Thr, Pro, Arg, Gly, Ala;
Xaa at position 75 is Glu, Lys, Gly, Asp. Pro, Trp, Arg, Ser. Gln, or Leu;
Xaa at position 76 is Ser, Val, Ala, Asn, Trp, Glu, Pro, Gly, or Asp;
Xaa at position 77 is Ile, Ser, Arg, Thr, or Len;
Xaa at position 78 is Leu, Ala, Ser, Glu, Phe, Gly, or Arg;
Xaa at position 79 is Lys, Thr, Asn. Met, Arg, Ile. Gly, or Asp;
Xaa at position 80 is Asn, Trp, Val, Gly, Tht, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp , Glu, Asn, His, Thr, Ser, Ala, Tyr. Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp. Cys, Leu, Vral. G il His, Asn, or Ser;
Xaa at position 90 is Ala, Pro, Ser, Thr, Gly, Asp. Ile, or Met;
Xaa at position 91 is Ala, Pro, Ser, Thr, Phe, Leu, Asp. or His;
Xaa at position 92 is Pro, Phe, Arg, Ser, Lys, His, Ala, Gly, Ile or Leu;
Xaa at position 93 is Thr, Asp. Ser, Asn, Pro, Ala, Leu, or Arg,
Xaa at position 94 is Arg, Ile, Ser, GlU, Leu, Val, Gln, Lys, His, Ala, or Pro;
Xaa at position 95 is His, Gln, Pro, Arg, Val, Leu, Gly, Thr, Asn, Lys, Ser, Ala, Trp, Pher Ile, orlTyr;
Xaa at position 96 is Pro, Lys, Tyr, rly, Ile, or Thr;
Xaa at position 97 is Ile, Val, Lys, Ala, or Asn;
Xaa at position 98 is His, Ile, Asn, Leu, Asp. Ala, Thr, Glu, Gln, Ser, Phe, Met, Val, Lys, Arg, Tyr or Pro;
Xaa at position 99 is Ile, Leu, Arg, Asp. val, Pro, Gln, Gly, Ser, Phe, or His;
Xaa at position 100 is Lys. Tyr, Leu, His, Arg, Ile, Ser, Gln, or Proi
Xaa at position 101 is Asp;
Xaa at position 102 is Gly, Leu, Glu, Lys, Ser, Tyr, or Pro;
Xaa at position 103 is Asp. or Ser; I
Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Le u, Lys, Ile, Asp. or His:

Xaa at position 106 is Glu, Ser, Ala, Lys, Thr, Ile, Gly, or Pro;

Xaa at position 108 is Arg, Lys, Asp. Leu, Thr, Ile, Gln, His, Ser, Ala or Pro;

Xaa at position 109 is Arg, Thr, Pro, Glu, Tyr, Leu, Ser, or Gly;

Xaa at position 110 is Lys. Ala, Asn, Thr, Leu, Arg, Gln, His, Glu, Ser, Ala, or Trp;

Xaa at position 111 is Leu, Ile, Arg, Asp. or Met;

Xaa at position 112 is Thr, Val, Gln, Tyr, Gln, His, Ser, or Phe;

Xaa at position 113 is Phe, Ser, Cys, His, Gly, Trp, Tyr, Asp. Lys, Leu, Ile, Val or Asn; :

Xaa at position 114 is Tyr, Cys, His, Ser, Trp, Arg, or Leu:

Xaa at position 115 is Leu, Asn, Val, Pro, Arg, Ala, His, Thr, Trp, or Met;

Xaa at position 111 is Lys;

Xaa at position 117 is Thr, Ser, A sn, Ile, Trp, Lys, or Pro;

Xaa at position 118 is Leu, Ser, Pro, Ala, Glu, Cys, Asp. or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp. or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

wherein from 1 to 3 of the amino acids designated by Xaa are different from the corresponding amino acids of native (1–133) human interleukin-3; wherein from 1 to 14 amino acids can optionally be deleted from the N-terminus and/or from 1 to 15 amino acids can optionally be deleted from the C-terminus of said modified hIL-3 amino acid sequence; said human interleukin-3 mutant polypeptide having at least three times greater cell proliferative activity than native human,interleukin-3, in at least one assay selected from the group consisting of: AML cell proliferation, TF-1 cell proliferation and methylcellulose assay; and a factor selected from the group consisting of; GM-CSF, C SF-1, G-CSF, G-CSF ($Ser^{17}$), M-CSF, erythropoietin (EPO), IL-1, IL-4, IL-2, IL-5, IL-6, EL-7, IL-8, IL-9, IL-lo, IL-11, IL-12, IL-13, LIF, flt3/flk2 ligand, human growth hormone, B-cell growth factor, B-cell differentiation factor, eosinophil differentiation factor and stem cell factor (SCF).

13. The composition according to claim 12, wherein said modified interleukin-3 amino acid sequence is selected from the group consisting of:

(a) an amino acid sequence of SEQ ID NO:2

(b) an N-terminal Met residue, Ala residue, or Met-Ala dipeptide joined to an amino acid sequence according to (a), wherein Xaa at position 17 is Ser, Gly, Asp. Met, or Gln;l Xaa at position 18 is Asn, His, or Ile;

Xaa at position 19 is Met or Ile;

Xaa at position 21 is Asp or GIU;

Xaa at position 23 is Ile, Ala, Leu, or Gly;

Xaa at position 24 is Ile, Val, or Leu;

Xaa at position 25 is Thr, His, Gln, or Ala;

Xaa at position 26 is His or Ala;

Xaa at position 29 is Gln, A sn, or Val;

Xaa at position 30 is Pro, Gly, or Gln;

Xaa at position 31 is Pro, Asp. Gly, or Gln,

Xaa at position 32 is Leu, Arg, Gln, A sn, Gly, Ala, or Glu;

Xaa at position 33 is Pro or Glu;

Xaa at position 34 is Leu, Val, Gly, Ser, Lys, Ala, Arg, Gln, Glu, Ile. Phe, Thr or Met;

Xaa at position 35 is Leu, Ala, Asn, Pro, Gln, or Val;

Xaa at position 37 is Phe, Ser, Pro, or Trp;

Xaa at position 38 is Asn or Ala;

Xaa at position 42 is Gly, Asp. Ser, Cys, Ala, Asn, Ile, Leu, Met, Tyr or Arg:

Xaa at position 44 is Asp or Glu;

Xaa at position 45 is Gln, Val, Met, Leu, Thr, Ala, Asn, Glu, Ser or Lys;

Xaa at position 46 is Asp. Phe, Ser, Thr, Ala, Asn, Gln, Glu, His, Ile, Lys, Tyr, Val or Cys;

Xaa at position 50 is Gl ui, Ala, Asn, Ser or Asp;

Xaa at position 51 is Asn, Arg y, Met, Pro, Ser, T hlr, or His;

Xaa at position 54 is Arg or Ala;

Xaa at position 55 is Arg, Thr, Val, Leu, or Gly;

Xaa at position 56 is Pro, Gly, Ser, Gln, Ala, Arg, Asn, Glu, Leu, Thr, Val or Lys;

Xaa at position 60 is Ala or Ser;

Xaa at position 62 is Asn. Pro, Thr, or Ile;

Xaa at position 63 is Arg or Lys;

Xaa at position 64 is Ala or Ash;

Xaa at position 65 is Val or Thr;

Xaa at position 66 is Lys or Arg;

Xaa at position 67 is Ser, Phe, or His; i

Xaa at position 68 is Le a, Ile, Phe, or His;

Xaa at position 69 is Gln, Ala, Pro, Thr, Glu, A4g, or Gly;

Xaa at position 71 is Ala, Pro, or Arg;

Xaa at position 72 is Ser, Glu, Arg, or Asp;

Xaa at position 73 is Ala or Len;

Xaa at position 76 is Ser, Val, Ala, Asn, Glu, Pro, or Gly;

Xaa at position 77 is Ile or Leu;

Xaa at position 79 is Lys, Thr, Gly, Asn, Met, Arg, Ile, Gly, or Asp;,

Xaa at position 80 is Asn, Gly, Glu, or Arg;

Xaa at position 82 is Leu, Gln, Trp, Arg, Asp. A1ia, Asn, Glu, His, Ile, Met, Phe, Ser, Thr, Tyr or Val;

Xaa at position 83 is Pro or Thr;

Xaa at position 85 is Leu or Val;

Xaa at position 87 is Leu or Ser;

Xaa at position 88 is Ala or Trp;

Xaa at position 91 is Ala or Pro;

Xaa at position 93 is Thr, Asp. Ser. Pro, Ala, Leu, or Arg,

Xaa at position 95 is His, Pro, Arg, Val, Leu, G iy, Asn, Phe, Ser or Thr;

Xaa at position 96 is Pro or Tyr;

Xaa at position 97 is Ile or Val;

Xaa at position 98 is His, Ile, Asn, Leu, Ala, Thr, Arg, Gln, Lys, Met, Ser, Tyr, Val or Pro;

Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr. Leu, Lys, Ile, Asp. or His;
Xaa at position 106 is Gin or Gly;
Xaa at position 108 is Ar y, Ala, or Ser;
Xaa at position 109 is Arg, Thr, Glu, Leu, or ser,;
Xaa at position 112 is Thr, Val, or Oln;
Xaa at position 114 is Tyr or Trp;
Xaa at position 115 is Leu or Ala;
Xaa at position 116 is Lys;
Xaa at position 117 is Thr or Ser,
Xaa at position 120 is Asn, Pro, Leu, His, Val, or Gln;
Xaa at position 121 is Ala, Ser, Ile, Asn, Pro, Asp. or Gly;
Xaa at position 122 is Gln, Ser, Met, Trp, Arg, Phe, Pro, His, Ile, Tyr. or Cys;
Xaa at position 123 is Ala, Met, Glu, His, Ser, Pro, Tyr, or Leu;
wherein from 1 to 3 of the amino acids designated by Xaa are different from the corresponding amino acids of native (1–133) human interleukin-3; wherein from 1 to 14 amino acids can optionally be deleted from the N-termrinus and/or from 1 to 15 amino acids can optionally be deleted from the C-terminus of said modified hIL-3 amino acid sequence.

14. The composition according to claim 12, wherein said modified interleukin-3 amino acid sequence is selected from the group consisting of:
    (a) an amino acid sequence of SEQ ID NO:3
    (b) an N-terminal Met residue, Ala residue, or Met-Ala dipeptide joined to an amino acid sequence according to (a), wherein Xaa at position 17 is Ser, Gly, Asp. or Gln;

Xaa at position 18 is Asn, His, or Ile;

Xaa at position 23 is Ile, Ala, Leu, or Gly;

Xaa at position 25 is Thr, His, or Gln;

Xaa at position 26 is His or Ala;

Xaa at position 29 is Gln or Asn;

Xaa at position 30 is Pro or Gly;

Xaa at position 32 is Leu, Arg, Asn, or Ala;

Xaa at position 34 is Leu, Val, Ser, Ala, Arg, Gln, Glu, Ile, Phe, Thr, or Met;

Xaa at position 35 is LenA, Ala, Asn, or Pro;

Xaa at position 38 is Asn or Ala;

Xaa at position 42 is Gly, Asp. Ser, Ala, Asn, Ile, Leu, Met, Tyr or Arg;

Xaa at position 45 is Gln, Val, Met, Len, Ala, Asn, Glu, or Lys;

Xaa at position 46 is Asp. Phe, Ser, Gln, Glu, His. Val or Thr;

Xaa at position 50 is Glu, Asn, Ser or Asp;

Xaa at position 51 is Asn, Arg, Pro, Thr, or His;

Xaa at position 55 is Arg, Leu, or Gly;

Xaa at position 56 is Pro, Cly, Ser, Ala, Asn, Val, Leu or Gln;

Xaa at position 62 is Asn, Vro, or Thr;

Xaa at position 64 is Ala or Asn;

Xaa at position 65 is Val or Thr;

Xaa at position 67 is Ser or Phe;

Xaa at position 68 is Leu or Phe;

Xaa at position 69 is Gln, Ala, Glu, or Arg;

Xaa at position 76 is Ser, Val, Asn, Pro, or Gly;

Xaa at position 77 is Ile or Leu;

Xaa at position 79 is Lys, Asn, Met, Arg, Ile, or Gly;

Xaa at position 80 is Asn, Gly, Glu, or Arg;

Xaa at position 82 is Le m, Gln, Trp, Arg, Asp. Asn, Glu, His, Met, Phe, Ser, Thr, Tyr or Val;

Xaa at position 87 is LeU or Ser;

Xaa at position 8S is Ala or Trp;

Xaa at position 91 is Ala or Pro;

Xaa at position 93 is Thr, Asp. or Ala;

Xaa at position 95 is His, Pro, Arg, Val, Gly, ASr i, Ser or Thr;

Xaa at position 98 is His, Ile, Asn, Ala, Thr, Gln, Glu, Lys, Met, Ser, Tyr, Val or Leu;

Xaa at position 99 is Ile or Leu;

Xaa at position 100 is Lys or Arg;

Xaa at position 101 is Asp;

Xaa at position 105 is Asn, Pro, Ser, Ile or Asp;

Xaa at position 108 is Arg, Ala, or Ser;

Xaa at position 109 is Arg, Thr, Glu, Leu, or Ser;

Xaa at position 112 is Thr or Gln;

Xaa at position 116 is Lys;

Xaa at position 120 is Asn, Pro, Leu, His, Val, or Gln;

Xaa at position 121 is Ala, Ser, Ile, Pro, or Asp;

Xaa at position 122 is Gln, Met, Trp, Phe, Pro, His, Ile, or Tyr;

Xaa at position 123 is Ala, Met, GlU, Ser, or Leu;

wherein from 1 to 3 of the amino acids designated by Xaa are different from the corresponding amino acids of native (1–133) human interleukin-3; wherein from 1 to 14 amino acids can optionally be deleted from the N-terminus and/or from 1 to 15 amino acids can optionally be deleted from the C-terminus of said modified hIL-3 amino acid sequence.

15. A composition of claim 14, wherein, in said modified interleukin-3 amino acid sequence (a):

Xaa at position 42 is Gly, Asp. Ser, Ile, Leu, Met, Tyr, or Ala;

Xaa at position 45 is Gln, Val, Met or Asn;

Xaa at position 46 is Asp. Ser, Gln, His or Val;

Xaa at position 50 is Glu or Asp;

Xaa at position 51 is Asn, Pro or Thr;

Xaa at position 62 is Asn or Pro;

Xaa at position 76 is Ser, or Pro;

Xaa at position 82 is Leu, Trp, Asp. Asn Glu, His, Phe, Ser or Tr

Xaa at position 95 is His, Arg, Thr, ksn or Ser;

Xaa at position 98 is His, Ile, Leu, Ala, Gln, Lys, Met, Ser, Tyr or Val;

Xaa at position 100 is Lys or Arg;

Xaa at position 108 is Arg, Ala, or Ser,

Xaa at position 121 is Ala, or Ile;

Xaa at position 122 is Gln, or Ile; and

Xaa at position 123 is Ala, Met or Glu.

16. A composition consisting of a mutant human interleukin-3 polypeptide having a modified interleukin-3 amino acid sequence selected from the group consisting of:

(a) an amino acid sequence of SEQ ID NO:4

(b) an N-terminal Met residue, Ala residue, or Met-Ala dipeptide joined to an amino acid sequence according to (a), wherein Xaa at position 3 is Ser, Lys, Gly, Asp. Met, Gln, or Arg;

Xaa at position 4 is Asn, His, Leu, lle, Phe, Arg, or Gln;

Xaa at position 5 is Met. Phe, Ile. Arg, Gly, Ala, or Cys;

Xaa at position 6 is Ile, Cys, Gln, Glu, Arg, Pro, or Ala;

Xaa at position 7 is Asp. Phe. Lys, Arg,l Ala, Gly, Glu, Gln, Asn, Thr, Ser or Val;

Xaa at position 8 is GlU, Trp, Pro, Ser,l Ala, His, Asp. Asn, Cln, Leu, Val, or Gly;

Xaa at position 9 is Ile, Val, Ala, Leu,l Gly, Trp, Lys, Phe, Ser, or Arg;

Xaa at position 10 is Ile, Gly, Val, Arg, Ser, Phe, or Leu;

Xaa at position 11 is Thr, His. Gly, Gln, A ig, Pro, or Ala;

Xaa at position 12 is His, Thr, Phe, Gly, Arg, Ala, or Trp;

Xaa at position 13 is Leu, Gly, Arg, Thr, Ser, or Ala;

Xaa at position 14 is Lys, Arg, Leu, Gln, ly, Pro, Val or Trp;

Xaa at position 15 is Gln, Asn, Len, Pro, Arg, or Val;

Xaa at position 16 is Pro, His, Thr, Gly, Asp. Gln, Ser, Leu, or Lys;

Xaa at position 17 is Pro, Asp. Gly, Ala, Arg, Leu, or Gln;

Xaa at position 18 is Leu, Val, Arg, Gln, Asn, Gly, Ala, or Glu;

Xaa at position 19 is Pro, Leu, Gln, Ala, Thr, or Glu;

Xaa at position 20 is Leu, Val, Gly, ser, Lys, Glu, Gln, Thir, Arg, Ala, Phe, Ile or Met;

Xaa at position 21 is Leu, Ala, Gly, Asn, Pro, Gln, or Val;

Xaa at position 22 is Asp. LeU, or Val;

Xaa at position 23 is Phe, Ser, Pro, Trp, or Ile;

Xaa at position 24 is Asn, or Ala;

Xaa at position 26 is Leu, Trp, or Arg;

Xaa at position 27 is Asn, Cys, Arg, Leu, His, Met, Pro;

Xaa at position 28 is Gly, Asp. Ser, Cys, Ala, Lys, Asn, Thr, Leu, Val. GlU, Phe, Tyr, Ile or Met;

Xaa at position 29 is Glu, Asn, Tyr, Leu, Phe, Asp. Ala, Cys, Gln, Arg, Thr, Gly or Ser;

Xaa at position 30 is Asp. Ser, Leu, Arg, Lys, T hr, Met, Trp, GiU, Asn, Gln, Ala or Pro;

Xaa at position 31 is Gln, Pro, Phe, Val, Met, Leu, Thr, Lys, Asp. Ash, Arg, Ser, Ala, Ile, Glu, His or Trp;

Xaa at position 32 is Asp. Phe, Ser. Thr, Cys, Glu, Asn, Gln, Lys, His, Ala, Tyr, Ile, Val or Gly;

Xaa at position 33 is Ile, Gly, Val, Ser, Arg, Pro, or His;

Xaa at position 34 is Leu, Ser, Cys, Arg, Ile, His, Phe, Glu, Lys, Thr, Ala, Met, Val or Asn;

Xaa at position 35 is Met, Arg, Ala, Gly, Pro, Asn, His, or Asp;

Xaa at position 36 is Glu, Leu, Thr, Asp. Tyr, Lys, Asn, Ser, Ala, Ile, Val, His, Phe, Met or Gln;

Xaa at position 37 is Asn, Arg, Met, Pro, Ser, Thr, or His;

Xaa at position 38 is Asn, His, Arg, Leu, Gly, Ser, or Thr;

Xaa at position 39 is Leu, Thr, Ala, Gly, Glu, Pro, Lys, Ser, or Met;

Xaa at position 40 is Arg, Asp. Ile, Ser, Val, Thr, Gln, Asn, Lys, His, Ala or Leu;

Xaa at position 41 is Arg, Thr, Val, Ser. Leu, or Gly;

Xaa at position 42 is Pro, Gly, Cys, Ser, Gln, Giu, Arg, His, Thr, Ala, Tyr, Phe, Leu, Val or Lys;

Xaa at position 43 is Asn or Gly;

Xaa at position 44 is Len, Ser, Asp. Arg; Gln, Val, or Cys;

Xaa at position 45 is Glu, Tyr, His, Led, Pro, or Arg;

Xaa at position 46 is Ala, Ser, Pro, Tyr, Asn, or Thr;

Xaa at position 47 is Phe, Asn, Glu, Pro, Lys, Arg, or Ser;

Xaa at position 48 is As g, His, Val, Arg, Pro, Thr, Asp. or Ile;

Xaa at position 49 is Arg, Tyr, Trp, Lys, Ser, His, Pro, or Val;

Xaa at position 50 is Ala, Asn, Pro, Ser, or Lys,

Xaa at position 51 is Val, Thr, Pro, His, Leu, Phe, or Ser;

Xaa at position 52 is Lys, Ile, Arg, Val, Asn, Glu, or Ser;

Xaa at position 53 is ser, Ala, Phe, Val, Gly, Asn, Ile, Pro, or His;

Xaa at position 54 is Leu, Val, Trp, Ser, Ile, Phe, Thr, or His;

Xaa at position 55 is Gln, Ala, Pro, Trp, Gln, Arg, Trp, Gly, or Leu;

Xaa at position 56 is Asn, Leu, Val, Trp, Pro, or Ala;

Xaa at position 57 is Ala, Met, Leu, Pro, Arg, Glu, Thr, Gln, Trp, or Asn;

Xaa at position 58 is Ser, Glu, Met, Ala, His, Asn, Arg, or Asp;

Xaa at position 59 is Ala, Glu, Asp Leu, Ser, Gly, Thr, or Arg;

Xaa at position 60 is Ile, Met, Thr, Pro, I Arg, Gly, Ala;

Xaa at position 61 is Glu, Lys, Gly, Asp. Pro, Trp, Arg, Ser, Gln, or Leu;

Xaa at position 62 is Ser, Val, Ala, Asn, Trp, Glu, Pro, Gly, or Asp.

Xaa at position 63 is Ile, Ser, Arg, Thr, or Leu;

Xaa at position 64 is Leu, Ala, Ser, Gly, Phe, Gly, or Arg;

Xaa at position 65 is Lys, Thr, Gly, AsLri; Met, Arg, Ile, or Asp;

Xaa at position 66 is Asn, Trp, Val, Gly, Thr, Leu, Glu, or Arg;

Xaa at position 67 is Leu, Gln, Gly, Ala, Trp, Arg, Val, or Lys;

Xaa at position 68 is Leu, Gln, Lys, Trp, Arg, Asp. Glu, Asn, His, Thr, Ser, Ala, Tyr, Phe, i Ile, Met or Val;

Xaa at position 69 is Pro, Ala, Thr, Trp, Arg, or Met;

Xaa at position 70 is Cys, Glu, Gly. Arg;, Met, or Val;

Xaa at position 71 is Leu, Asn, Val, or Gln;

Xaa at position 72 is Pro, Cys, Arg, Ala, or Lys,

Xaa at position 73 is Leu, Ser, Trp, or Gly;

Xaa at position 74 is Ala, Lys, Arg, Val, or Trp;

Xaa at position 75 is Thr, Asp. Cys, Leu, Val, Glu, His, Asn, or Ser;

Xaa at position 76 is Ala, Pro, Ser, Thr, Gly, Asp. Ile, or Met;

Xaa at position 77 is Ala, Pro, Ser, Thr, Phe, Leu, Asp. or His;

Xaa at position 78 is Pro, Phe,,Arg, Ser, Lys, His, Ala, Gly, Ile or Leu;

Xaa at position 79 is Thr, Asp. Ser, Asn, Pro, Ala, Leu, or Arg;

Xaa at position 80 is Arg, Ile, Ser, Glu, Leu, Val, Gln, Lys, His, Ala or Pro;

Xaa at position 81 is His, Gln, Pro, Arg, Val, Leu, Gly, Thr, Asn, Lys, Ser, Ala, Trp, Phe, Ile or Try;

Xaa at position 82 is Pro, Lys, Tyr, Gly, Ile, or Thr;

Xaa at position 83 is Ile, Val, Lys, Ala, or Asn;

Xaa at position 84 is His, Ile, Asn, Leu, Asp. Ala, Thr, Glu, Gln, Ser, Phe, Met, Val, Lys, Arg, Tyr or Pro;

Xaa at position 85 is Ile, Leu, ,Arg, Asp. Val, Pro, Gln, Gly, Ser, Phe, or His;

Xaa at position 86 is Lys, Tyr,,Leu, His, Arg, Ile,Ser, Gln, Pro;

Xaa at position 87 is Asp;

Xaa at position 88 is Gly, Leu,,Glu. Lys, ser, Tyr, or Pro;

Xaa at position 89 is Asp. or Ser;

Xaa at position 90 is Trp, Val, Cys, Tyr, Thr, Met, Pro, Leu, Gln, Lys, Ala, Phe, or Gly;

Xaa at position 91 is Asn, Pro, Ala, Phe, Ser, Trp, Gln, Tyr, Leu, Lys, Ile, Asp. or His;

Xaa at position 92 is Glu, Ser, Ala, Lys, Thr, Ile, Gly, or Pro;

Xaa at position 94 is Arg, Lys, Asp. Lue, u, Thr, Ile, Gln, His, Ser, Ala, or Pro;

Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;

Xaa at position 97 is Leu, Ile, Arg, Asp. or Met;

Xaa at position 98 is Thr, Val, Gln, Tyr, GlU, His, Ser. or Phe;

Xaa at position 99 is Phe, Ser, Cys, His, Gly, Trp, Tyr, Asp. Lys, Leu, Ile. Val or Asr;

Xaa at position 100 is Tyr, Cys N His, Ser, Trp, Arg, or Leu;

Xaa at position 101 is Leu, Asn, Val, Pro, Arg, Ala, His, Thr, Trp, or Met;

Xaa at position 102 is Lys;

Xaa at position 103 is Thr, Ser, Asn, Ile, Trp, Lys, or Pro;

Xaa at position 104 is Leu, Se c, Pro, Ala, Glu, Cys, Asp. or Tyr;

Xaa at position 105 is Glu, Ser, Lys, Pro, Leu, Thr, Tyr, or Arg;

Xaa at position 106 is Asn, Aja, Pro, Let, His, Val, or Gln;

Xaa at position 107 is Ala, Ser, i ie, Asn, Pro, Lys, Asp. or Gly;

Xaa at position 108 is Gln, Ser, Met, Trp, Arg, Phe, Pro, His, Ile, Tlyr, or Cys;

Xaa at position 109 is Ala, Met, Glu, His, Ser, Pro, Tyr, or Leu;

wherein from 1 to 3 of the amino iacids designated by Xaa are different from the corresponding native amino acids of (1–133) human interleukin-3; said human interleukin-3 mutant polypeptide having at least three times greater cell proliferative activity than nati e human interleukin-3, in at least one assay selected from ithe group consisting of: AML cell proliferation, TF-1 cell I proliferation and Methylcellulose assay; and a factor selected from the group consisting of: GM-CSF, CSF-1, G-CSF, G-CSF (Ser$^{17}$), M-CSF, erythropoietin (EPO), IL-1, IL-4 1, IL-2, IL-5, IL-6, IL-7, IL -8, IL-9, IL-10, IL-11, IL-12, IL-13, LIF, flt3/flk2 ligand, human growth hormone, B-cell growth factor, B-cell differentiation factor, eosinophil differentiation factor and stem cell factor (SCF).

17. The composition according to claim 16, wherein said modified interleukin-3 amino acid sequence is selected from the group consisting of:

(a) an amino acid sequence of SEQ ID NO:5

(b) an N-terminal Met residue, Ala residue, or Met-Ala dipeptide joined to an amino acid sequence according to (a), wherein Xaa at position 3 is Ser, Gly, Asp. Met, or Gln;

Xaa at position 4 is Asn, His, or Ile;

Xaa at position 5 is Met or Ile;

Xaa at position 7 is Asp or GlU;

Xaa at position 9 is Ile, Ala, Leu, origly;

Xaa at position 10 is Ile, Val, or Leu;

Xaa at position 11 is Thr, Hisr Gln, or Ala;

Xaa at position 12 is His or Ala;

Xaa at position 15 is Gln, Asn, or Val;

Xaa at position 16 is Pro, Gly, or Gln;

Xaa at position 17 is Pro, Asp. Gly, or Gln,

Xaa at position 18 is Len, Arg, Gli, Asn, Gly, Ala, or Glu;

Xaa at position 19 is Pro or Glu;

Xaa at position 20 is Leu, Val, Gly, Ser, Lys, Ala, Arg, Gln, Glu, Ile, Phe, Thr or Met;

Xaa at position 21 is Leu, Ala, Asn, Pro, Gln, or Val;

Xaa at position 23 is Phe, Ser, Pro, or Trp;

Xaa At position 24 is A sn or Ala;

Xaa at position 28 is Gly, Asp. Ser, Cys, Ala, Asn, Ile, Leu, Met Try, or Arg;

Xaa at position 30 is Asp or Glu;

Xaa at position 31 is Gln, Val, Met, Leu, rhr, Ala, Asn, Glu, Ser or Lys;

Xaa at position 32 is Asp. Phe, Ser, Thr, Ala, Asn, Gln, Glu, His, Ile, Lys, Tyr, Val or Cys:

Xaa at position 36 is Glu, Ala, Asn, Ser or Asp;

Xaa at position 37 is Asn, Arg, Met, Pro, ser, Thr, or His;

Xaa at position 40 is Arg or Ala;

Xaa at position 41 is Arg, Thr, Val, Leu, or dly;

Xaa at position 42 is Pro, Gly, Ser, Gln, Ala, Arg, Asn, Glu, Leu, Thr, Val or Lys;

Xaa at position 46 is Ala or Ser;

Xaa at position 48 is Asn, Pro, Thr, or Ile;

Xaa at position 49 is Arg or Lys;

Xaa at position 50 is Ala or Asn;

Xaa at position 51 is Val or Thr;

Xaa at position 52 is Lys or Arg;

Xaa at position 53 is Ser, Phe, or His;

Xaa at position 54 is Leta, lie, Phe, or His;

Xaa at position 55 is Glu, Ala, Pro, Thr, Glu, Arg, or Gly;

Xaa at position 57 is Ala, Pro, or Arg;

Xaa at position 58 is Ser, Glu, Arg, or Asp;

Xaa at position 59 is Ala or Leu;

Xaa at position 62 is Ser, Val, Ala, Asn, Glu, Pro, or Gly;

Xaa at position 63 is Ile or Leu;

Xaa at position 65 is Lys, Thr, Gly, Asn, Met, Arlg, Ile, or Asp;

Xaa at position 66 is Asn, Gly, Glu, or Arg;

Xaa at position 68 is Leu, Gln, Trp, Arg, Asp. Alt a, Asn, Glu, His, Ile, Met, Phe, Ser, Thr, Tyr or Val;

Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro,
Xaa at position 75 is Thr, Asp. Ser, Pro, Ala, Letu, or Arg,
Xaa at position 81 is His, Pro, Arg, Val, Leu, Gly, Asn, Phe, Ser or
Xaa at position 82 is Pro or Tyr;
Xaa at position 83 is Ile or Val;
Xaa at position 84 is His, le, Asn, Leu, Ala, Thr, Arg, Gln, Lys, Met, Ser, Tyr, Val or Pro;
Xaa at position 85 is lie, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp. or His;
Xaa at position 92 is Glu, or Gly;
Xaa at position 94 is Art. Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp. or Gly;
Xaa at position 108 is Gln, Ser, Met, Trp, Arg, Phe, Pro, His, Ile, Try, or Cys;
Xaa at position 109 is Ala, Met, Glu, His, Ser, Pro, Tyr, or Leu;
wherein from 1 to 3 of the amino acids designated by Xaa are different from the corresponding amino acids of native human interleukin-3.

18. The composition according to cltaim 16, wherein said modified interleukin-3 amino acid sequence is selected from the group consisting of:
 (a) an amino acid sequence of SEQ ID NO:7
 (b) an N-terminal Met residue, Ala residue, or Met-Ala dipeptide joined to an amino acid sequence according to (a),
wherein;
Xaa at position 3 is Ser, Gly, Asp. or Gln;
Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leun Ala, Asn, or Pro;
Xaa at position 24 is Asn or Ala;
Xaa at position 28 is Gly, Asp. Ser, Ala,l Asn, Ile, Leu, Met, Tyr or Arg;
Xaa at position 31 is Gln, Val, Met, Leu, : Ala, Asn, Glu or Lys;

Xaa at position 32 is Asp. Phe, Ser, Ala, Gln, Glu, His, Val or Thr;
Xaa at position 36 is Glu, Asn, Ser or Asn;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Len or Phe;
Xaa at position 55 is Gln, Ala, Glu, or Arg;
Xaa at position 62 is Ser, Val, Asn, Pro, or Gly;
Xaa at position 63 is Ile or Leu,
Xaa at position 65 is Lys, Asn, Met, Arg, Ile, or Gly;
Xaa at position 66 is Asn, Gly, Gln, or Arg;
Xaa at position 68 is Len, Gln, Try, Arg, Asp. Asn, Glu, His, Met, Phe, Ser, Thr, Tyrlor Val;
Xaa at position 73 is Leu or Ser;
Xaa at position 74 is Ala or Trp;
Xaa at position 77 is Ala or Pro;
Xaa at position 79 is Thr, Asp. or Ala;
Xaa at posi.tion 81 is His, Pro, Arg, Val, Gly, Asn, Ser or Thr;
Xaa at position 84 is His, Ile, Asn, Ala, I:Thr, Arg, Gln, Glu, Lys, Met, Ser, Tyr, Val $_1$or Leu;
Xaa at position 85 is lie or Leu;
Xaa at position 86 is Lys or Arg;
Xaa at position 87 is Asp;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln,
Xaa at position 102 is Lys;
Xaa at position 103 is Thr, Ala, His, Phe,, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met,:Trp, Phe, Pro, His, Ile, or Tyr;
Xaa at position 109 is Ala, Met,llu, Serl, or Leu;
wherein from 1 to 3 of the aminol,acids designated by Xaa are different from the corresponding amino acids of native (1–133) human interleukin-3.

19. The composition according to claim 16, wherein said modified interleukin-3 aminoacid sequence is selected from the group consisting of:
 (a) an amino acid sequence :of SEQ ID, . NO:8
 (b) an N-terminal Met residue, Ala residue, or Met-Ala dipeptide joined to an amino acid sequence according to (a),
wherein;
Xaa at position 4 is Asn or lie;
Xaa at position 5 is Met, Ala or Ile;
Xaa at position 6 is Iler Pro or Leu;
Xaa at position 9 is Tle, Ala or Leu;
Xaa at position 11 is Thr or His;
Xaa at position 5 is Gln, Arg, Val or Leu;
Xaa at position 18 is Leu, Ala, Asn or Arg;

Xaa at position 20 is Leu or Ser;
Xaa at position 23 is Phe, Pro, or Ser;
Xaa at position 24 is Asn or Ala;
Xaa at position 28 is Gly, Ala, Ser, Asp or Asn;
Xaa at position 31 is Gln, Val. or Met;
Xaa at position 32 is Asp or Ser;
Xaa at position 35 is Met, Ile or Asp;
Xaa at position 36 is Glu or Asp;
Xaa at position 37 is Asn, Arg or Ser;
Xaa at position 41 is Arg, Leu, or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gly;
Xaa at position 55 is Gin or Glu;
Xaa at position 59 is Ala or Gly;
Xaa at position 62 is Ser, Ala or Pro;
Xaa at position 65 is Lys, Arg or ser;
Xaa at position 67 is Leu, Glu, or Val;
Xaa at position 68 is Leu, Glu, Val or Trp;
Xaa at position 71 is Leu or Val;
Xaa at position 73 is Leu, Ser or Trp;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile, or Thr;
Xaa at position 86 is Lys or Arg;
Xaa at position 91 is Asn or Gln;
Xaa at position 95 is Arg, Glu, Leu;

Xaa at position 98 is Thr or dln;
Xaa at position 103 is Thr or Ser;
Xaa at position 106 is Asn, Gln, or His;
Xaa at position 109 is Ala or Glu;
wherein from one to three of the amino acids designated by Xaa are different from the corresponding amino acids of native (1–133) human interleukin-3.

20. The composition of claim 1, 2, 3, 4, 5, 6, 7, 8, 9, 10, 11, 12, 13, 14, 15, 16, 17, 18 or 19 wherein said factor is selected from the group consisting of: G-CSF, G-CSF (Ser$^{17}$) and GM-CSF.

21. A composition comprising; a mutant human interleukin-3 (hIL-3) polypeptide wherein the amino acid corresponding to residue 50 of native interleukin-3: is aspartic acid i and a human G-CSF (Ser$^{17}$) polypeptide.

22. A composition according to claim 21, wherein the mutant human interleukin-3 polypeptide corresponds to [50 D]-hIL-3 and has an amino acid sequence selected from the group consisting of:

(a) a sequence which is identical to residues 2–134 of SEQ ID NO: 9 except for the replacement of the Glu residue at position 51 by Asp; and (b) an N-terminal Met residue, Ala residue. or Met-Ala-dipeptide joined to an amino acid sequence according to (a).

23. A composition according to claim 21, wherein the mutant human interleukin-3 polypeptide corresponds to [50D]-(15–125) hIL-3 and has an amino acid sequence selected from the group consisting of:

(a) a sequence which is identical to residues 16–126 of SEQ ID NO: 9 except for the replacement of the Glu residue at position 51 by Asp; and (b) an N-terminal Met residue, Ala residue, or Met-Ala-dipeptide joined to an amino acid sequence according to (a).

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Met- may or may not precede the amino acid in position 1"

( i x ) FEATURE:
        ( A ) NAME/KEY: Modified-site
        ( B ) LOCATION: 17
        ( D ) OTHER INFORMATION: /note= "Xaa at position 17 is Ser, Lys, Gly, Asp, Met, Gln, or Arg"

( i x ) FEATURE:
        ( A ) NAME/KEY: Modified-site
        ( B ) LOCATION: 18
        ( D ) OTHER INFORMATION: /note= "Xaa at position 18 is Asn, His, Leu, Ile, Phe, Arg, or Gln"

( i x ) FEATURE:
        ( A ) NAME/KEY: Modified-site
        ( B ) LOCATION: 19
        ( D ) OTHER INFORMATION: /note= "Xaa at positiion 19 is Met, Phe, Ile, Arg, Gly, Ala, or Cys"

( i x ) FEATURE:
    ( A ) NAME/KEY: Modified-site
    ( B ) LOCATION: 20
    ( D ) OTHER INFORMATION: /note= "Xaa at position 20 is Ile,
        Cys, Gln, Glu, Arg, Pro, or Ala"

( i x ) FEATURE:
    ( A ) NAME/KEY: Modified-site
    ( B ) LOCATION: 21
    ( D ) OTHER INFORMATION: /note= "Xaa at position 21 is Asp,
        Phe, Lys, Arg, Ala, Gly, Glu, Gln, Asn, Thr, Ser,
        or Val"

( i x ) FEATURE:
    ( A ) NAME/KEY: Modified-site
    ( B ) LOCATION: 22
    ( D ) OTHER INFORMATION: /note= "Xaa at position 22 is Glu,
        Trp, Pro, Ser, Ala, His, Asp, Asn, Gln, Leu, Val,
        or Gly"

( i x ) FEATURE:
    ( A ) NAME/KEY: Modified-site
    ( B ) LOCATION: 23
    ( D ) OTHER INFORMATION: /note= "Xaa at position 23 is Ile,
        Val, Ala, Leu, Gly, Trp, Lys, Phe, Ser, or
        Arg"

( i x ) FEATURE:
    ( A ) NAME/KEY: Modified-site
    ( B ) LOCATION: 24
    ( D ) OTHER INFORMATION: /note= "Xaa at position 24 is Ile,
        Gly, Val, Arg, Ser, Phe, or Leu"

( i x ) FEATURE:
    ( A ) NAME/KEY: Modified-site
    ( B ) LOCATION: 25
    ( D ) OTHER INFORMATION: /note= "Xaa at position 25 is Thr,
        His, Gly, Gln, Arg, Pro, or Ala"

( i x ) FEATURE:
    ( A ) NAME/KEY: Modified-site
    ( B ) LOCATION: 26
    ( D ) OTHER INFORMATION: /note= "Xaa at position 26 is His,
        Thr, Phe, Gly, Arg, Ala, or Trp"

( i x ) FEATURE:
    ( A ) NAME/KEY: Modified-site
    ( B ) LOCATION: 27
    ( D ) OTHER INFORMATION: /note= "Xaa at position 27 is Leu,
        Gly, Arg, Thr, Ser, or Ala"

( i x ) FEATURE:
    ( A ) NAME/KEY: Modified-site
    ( B ) LOCATION: 28
    ( D ) OTHER INFORMATION: /note= "Xaa at position 28 is Lys,
        Arg, Leu, Gln, Gly, Pro, Val, or Trp"

( i x ) FEATURE:
    ( A ) NAME/KEY: Modified-site
    ( B ) LOCATION: 29
    ( D ) OTHER INFORMATION: /note= "Xaa at position 29 is Gln,
        Asn, Leu, Pro, Arg, or Val"

( i x ) FEATURE:
    ( A ) NAME/KEY: Modified-site
    ( B ) LOCATION: 30
    ( D ) OTHER INFORMATION: /note= "Xaa at position 30 is Pro,
        His, Thr, Gly, Asp, Gln, Ser, Leu, or Lys"

( i x ) FEATURE:
    ( A ) NAME/KEY: Modified-site
    ( B ) LOCATION: 31
    ( D ) OTHER INFORMATION: /note= "Xaa at position 31 is Pro,
        Asp, Gly, Ala, Arg, Leu, or Gln"

( i x ) FEATURE:
    ( A ) NAME/KEY: Modified-site
    ( B ) LOCATION: 32

(D) OTHER INFORMATION: /note= "Xaa at position 32 is Leu,
Val, Arg, Gln, Asn, Gly, Ala, or Glu"

(ix) FEATURE:
    (A) NAME/KEY: Modified-site
    (B) LOCATION: 33
    (D) OTHER INFORMATION: /note= "Xaa at position 33 is Pro,
        Leu, Gln, Ala, Thr, or Glu"

(ix) FEATURE:
    (A) NAME/KEY: Modified-site
    (B) LOCATION: 34
    (D) OTHER INFORMATION: /note= "Xaa at position 34 is Leu,
        Val, Gly, Ser, Lys, Glu, Gln, Thr, Arg, Ala, Phe,
        Ile, or Met"

(ix) FEATURE:
    (A) NAME/KEY: Modified-site
    (B) LOCATION: 35
    (D) OTHER INFORMATION: /note= "Xaa at position 35 is Leu,
        Ala, Gly, Asn, Pro, Gln, or Val"

(ix) FEATURE:
    (A) NAME/KEY: Modified-site
    (B) LOCATION: 36
    (D) OTHER INFORMATION: /note= "Xaa at position 36 is Asp,
        Leu, or Val"

(ix) FEATURE:
    (A) NAME/KEY: Modified-site
    (B) LOCATION: 37
    (D) OTHER INFORMATION: /note= "Xaa at position 37 is Phe,
        Ser, Pro, Trp, or Ile"

(ix) FEATURE:
    (A) NAME/KEY: Modified-site
    (B) LOCATION: 38
    (D) OTHER INFORMATION: /note= "Xaa at position 38 is Asn,
        or Ala"

(ix) FEATURE:
    (A) NAME/KEY: Modified-site
    (B) LOCATION: 40
    (D) OTHER INFORMATION: /note= "Xaa at position 40 is Leu,
        Trp, or Arg"

(ix) FEATURE:
    (A) NAME/KEY: Modified-site
    (B) LOCATION: 41
    (D) OTHER INFORMATION: /note= "Xaa at position 41 is Asn,
        Cys, Arg, Leu, His, Met, or Pro"

(ix) FEATURE:
    (A) NAME/KEY: Modified-site
    (B) LOCATION: 42
    (D) OTHER INFORMATION: /note= "Xaa at position 42 is Gly,
        Asp, Ser, Cys, Asn, Lys, Thr, Leu, Val, Glu, Phe, Tyr,
        Ile, Met, or Ala"

(ix) FEATURE:
    (A) NAME/KEY: Modified-site
    (B) LOCATION: 43
    (D) OTHER INFORMATION: /note= "Xaa at position 43 is Glu,
        Asn, Tyr, Leu, Phe, Asp, Ala, Cys, Gln, Arg, Thr, Gly,
        or Ser"

(ix) FEATURE:
    (A) NAME/KEY: Modified-site
    (B) LOCATION: 44
    (D) OTHER INFORMATION: /note= "Xaa at position 44 is Asp,
        Ser, Leu, Arg, Lys, Thr, Met, Trp, Glu, Asn, Gln, Ala,
        or Pro"

(ix) FEATURE:
    (A) NAME/KEY: Modified-site
    (B) LOCATION: 45
    (D) OTHER INFORMATION: /note= "Xaa at position 45 is Gln,
        Pro, Phe, Val, Met, Leu, Thr, Lys, Trp, Asp, Asn, Arg,
        Ser, Ala, Ile, Glu, or His"

( i x ) FEATURE:
    ( A ) NAME/KEY: Modified-site
    ( B ) LOCATION: 46
    ( D ) OTHER INFORMATION: /note= "Xaa at position 46 is Asp,
        Phe, Ser, Thr, Cys, Glu, Asn, Gln, Lys, His, Ala, Tyr,
        Ile, Val, or Gly"

( i x ) FEATURE:
    ( A ) NAME/KEY: Modified-site
    ( B ) LOCATION: 47
    ( D ) OTHER INFORMATION: /note= "Xaa at position 47 is Ile,
        Gly, Val, Ser, Arg, Pro, or His"

( i x ) FEATURE:
    ( A ) NAME/KEY: Modified-site
    ( B ) LOCATION: 48
    ( D ) OTHER INFORMATION: /note= "Xaa at position 48 is Leu,
        Ser, Cys, Arg, Ile, His, Phe, Glu, Lys, Thr, Ala, Met,
        Val, or Asn"

( i x ) FEATURE:
    ( A ) NAME/KEY: Modified-site
    ( B ) LOCATION: 49
    ( D ) OTHER INFORMATION: /note= "Xaa at position 49 is Met,
        Arg, Ala, Gly, Pro, Asn, His, or Asp"

( i x ) FEATURE:
    ( A ) NAME/KEY: Modified-site
    ( B ) LOCATION: 50
    ( D ) OTHER INFORMATION: /note= "Xaa at position 50 is Glu,
        Leu, Thr, Asp, Tyr, Lys, Asn, Ser, Ala, Ile, Val, His,
        Phe, Met, or Gln"

( i x ) FEATURE:
    ( A ) NAME/KEY: Modified-site
    ( B ) LOCATION: 51
    ( D ) OTHER INFORMATION: /note= "Xaa at position 51 is Asn,
        Arg, Met, Pro, Ser, Thr, or His"

( i x ) FEATURE:
    ( A ) NAME/KEY: Modified-site
    ( B ) LOCATION: 52
    ( D ) OTHER INFORMATION: /note= "Xaa at position 52 is Asn,
        His, Arg, Leu, Gly, Ser, or Thr"

( i x ) FEATURE:
    ( A ) NAME/KEY: Modified-site
    ( B ) LOCATION: 53
    ( D ) OTHER INFORMATION: /note= "Xaa at position 53 is
        Leu, Thr, Ala, Gly, Glu, Pro, Lys, Ser, or Met"

( i x ) FEATURE:
    ( A ) NAME/KEY: Modified-site
    ( B ) LOCATION: 54
    ( D ) OTHER INFORMATION: /note= "Xaa at position 54 is Arg,
        Asp, Ile, Ser, Val, Thr, Gln, Asn, Lys, His, Ala,
        or Leu"

( i x ) FEATURE:
    ( A ) NAME/KEY: Modified-site
    ( B ) LOCATION: 55
    ( D ) OTHER INFORMATION: /note= "Xaa at position 55 is Arg,
        Thr, Val, Ser, Leu, or Gly"

( i x ) FEATURE:
    ( A ) NAME/KEY: Modified-site
    ( B ) LOCATION: 56
    ( D ) OTHER INFORMATION: /note= "Xaa at position 56 is Pro,
        Gly, Cys, Ser, Gln, Glu, Arg, His, Thr, Ala, Tyr,
        Phe, Leu, Val, or Lys"

( i x ) FEATURE:
    ( A ) NAME/KEY: Modified-site
    ( B ) LOCATION: 57
    ( D ) OTHER INFORMATION: /note= "Xaa at position 57 is Asn
        or Gly"

( i x ) FEATURE:
    ( A ) NAME/KEY: Modified-site
    ( B ) LOCATION: 58

(D) OTHER INFORMATION: /note= "Xaa at position 58 is Leu,
Ser, Asp, Arg, Gln, Val, or Cys"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, Pro, or Arg"

(ix) FEATURE:
    (A) NAME/KEY: Modified-site
    (B) LOCATION: 60
    (D) OTHER INFORMATION: /note= "Xaa at position 60 is Ala,
        Ser, Pro, Tyr, Asn, or Thr"

(ix) FEATURE:
    (A) NAME/KEY: Modified-site
    (B) LOCATION: 61
    (D) OTHER INFORMATION: /note= "Xaa at position 61 is Phe,
        Asn, Glu, Pro, Lys, Arg, or Ser"

(ix) FEATURE:
    (A) NAME/KEY: Modified-site
    (B) LOCATION: 62
    (D) OTHER INFORMATION: /note= "Xaa at position 62 is Asn,
        His, Val, Arg, Pro, Thr, Asp, or Ile"

(ix) FEATURE:
    (A) NAME/KEY: Modified-site
    (B) LOCATION: 63
    (D) OTHER INFORMATION: /note= "Xaa at position 63 is Arg,
        Tyr, Trp, Lys, Ser, His, Pro, or Val"

(ix) FEATURE:
    (A) NAME/KEY: Modified-site
    (B) LOCATION: 64
    (D) OTHER INFORMATION: /note= "Xaa at position 64 is Ala,
        Asn, Pro, Ser, or Lys"

(ix) FEATURE:
    (A) NAME/KEY: Modified-site
    (B) LOCATION: 65
    (D) OTHER INFORMATION: /note= "Xaa at position 65 is Val,
        Thr, Pro, His, Leu, Phe, or Ser"

(ix) FEATURE:
    (A) NAME/KEY: Modified-site
    (B) LOCATION: 66
    (D) OTHER INFORMATION: /note= "Xaa at position 66 is Lys,
        Ile, Arg, Val, Asn, Glu, or Ser"

(ix) FEATURE:
    (A) NAME/KEY: Modified-site
    (B) LOCATION: 67
    (D) OTHER INFORMATION: /note= "Xaa at position 67 is Ser,
        Ala, Phe, Val, Gly, Asn, Ile, Pro, or His"

(ix) FEATURE:
    (A) NAME/KEY: Modified-site
    (B) LOCATION: 68
    (D) OTHER INFORMATION: /note= "Xaa at position 68 is Leu,
        Val, Trp, Ser, Ile, Phe, Thr, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, Trp, Gly, or Leu"

(ix) FEATURE:
    (A) NAME/KEY: Modified-site
    (B) LOCATION: 70
    (D) OTHER INFORMATION: /note= "Xaa at position 70 is Asn,
        Leu, Val, Trp, Pro, or Ala"

(ix) FEATURE:
    (A) NAME/KEY: Modified-site
    (B) LOCATION: 71
    (D) OTHER INFORMATION: /note= "Xaa at position 71 is
        Ala, Met, Leu, Pro, Arg, Glu, Thr, Gln, Trp, or Asn"

( i x ) FEATURE:
    ( A ) NAME/KEY: Modified-site
    ( B ) LOCATION: 72
    ( D ) OTHER INFORMATION: /note= "Xaa at position 72 is Ser,
        Glu, Met, Ala, His, Asn, Arg, or Asp"

( i x ) FEATURE:
    ( A ) NAME/KEY: Modified-site
    ( B ) LOCATION: 73
    ( D ) OTHER INFORMATION: /note= "Xaa at position 73 is Ala,
        Glu, Asp, Leu, Ser, Gly, Thr, or Arg"

( i x ) FEATURE:
    ( A ) NAME/KEY: Modified-site
    ( B ) LOCATION: 74
    ( D ) OTHER INFORMATION: /note= "Xaa at position 74 is Ile,
        Met, Thr, Pro, Arg, Gly, or Ala"

( i x ) FEATURE:
    ( A ) NAME/KEY: Modified-site
    ( B ) LOCATION: 75
    ( D ) OTHER INFORMATION: /note= "Xaa at position 75 is
        Glu, Lys, Gly, Asp, Pro, Trp, Arg, Ser, Gln,
        or Leu"

( i x ) FEATURE:
    ( A ) NAME/KEY: Modified-site
    ( B ) LOCATION: 76
    ( D ) OTHER INFORMATION: /note= "Xaa at position 76 is Ser,
        Val, Ala, Asn, Trp, Glu, Pro, Gly, or Asp"

( i x ) FEATURE:
    ( A ) NAME/KEY: Modified-site
    ( B ) LOCATION: 77
    ( D ) OTHER INFORMATION: /note= "Xaa at position 77 is Ile,
        Ser, Arg, Thr, or Leu"

( i x ) FEATURE:
    ( A ) NAME/KEY: Modified-site
    ( B ) LOCATION: 78
    ( D ) OTHER INFORMATION: /note= "Xaa at position 78 is Leu,
        Ala, Ser, Glu, Phe, Gly, or Arg"

( i x ) FEATURE:
    ( A ) NAME/KEY: Modified-site
    ( B ) LOCATION: 79
    ( D ) OTHER INFORMATION: /note= "Xaa at position 79 is Lys, Thr,
        Asn, Met, Arg, Ile, Gly, or Asp"

( i x ) FEATURE:
    ( A ) NAME/KEY: Modified-site
    ( B ) LOCATION: 80
    ( D ) OTHER INFORMATION: /note= "Xaa at position 80 is Asn,
        Trp, Val, Gly, Thr, Leu, Glu, or Arg"

( i x ) FEATURE:
    ( A ) NAME/KEY: Modified-site
    ( B ) LOCATION: 81
    ( D ) OTHER INFORMATION: /note= "Xaa at position 81 is Leu,
        Gln, Gly, Ala, Trp, Arg, Val, or Lys"

( i x ) FEATURE:
    ( A ) NAME/KEY: Modified-site
    ( B ) LOCATION: 82
    ( D ) OTHER INFORMATION: /note= "Xaa at position 82 is Leu,
        Gln, Lys, Trp, Arg, Asp, Glu, Asn, His, Thr, Ser, Ala,
        Tyr, Phe, Ile, Met, or Val"

( i x ) FEATURE:
    ( A ) NAME/KEY: Modified-site
    ( B ) LOCATION: 83
    ( D ) OTHER INFORMATION: /note= "Xaa at position 83 is Pro,
        Ala, Thr, Trp, Arg, or Met"

( i x ) FEATURE:
    ( A ) NAME/KEY: Modified-site
    ( B ) LOCATION: 84
    ( D ) OTHER INFORMATION: /note= "Xaa at position 84 is Cys, Glu, Gly, Arg, Met, or Val"

( i x ) FEATURE:
    ( A ) NAME/KEY: Modified-site
    ( B ) LOCATION: 85
    ( D ) OTHER INFORMATION: /note= "Xaa at position 85 is Leu, Asn, Val, or Gln"

( i x ) FEATURE:
    ( A ) NAME/KEY: Modified-site
    ( B ) LOCATION: 86
    ( D ) OTHER INFORMATION: /note= "Xaa at position 86 is Pro, Cys, Arg, Ala, or Lys"

( i x ) FEATURE:
    ( A ) NAME/KEY: Modified-site
    ( B ) LOCATION: 87
    ( D ) OTHER INFORMATION: /note= "Xaa at position 87 is Leu, Ser, Trp, or Gly"

( i x ) FEATURE:
    ( A ) NAME/KEY: Modified-site
    ( B ) LOCATION: 88
    ( D ) OTHER INFORMATION: /note= "Xaa at position 88 is Ala, Lys, Arg, Val, or Trp"

( i x ) FEATURE:
    ( A ) NAME/KEY: Modified-site
    ( B ) LOCATION: 89
    ( D ) OTHER INFORMATION: /note= "Xaa at position 89 is Thr, Asp, Cys, Leu, Val, Glu, His, Asn, or Ser"

( i x ) FEATURE:
    ( A ) NAME/KEY: Modified-site
    ( B ) LOCATION: 90
    ( D ) OTHER INFORMATION: /note= "Xaa at position 90 is Ala, Pro, Ser, Thr, Gly, Asp, Ile, or Met"

( i x ) FEATURE:
    ( A ) NAME/KEY: Modified-site
    ( B ) LOCATION: 91
    ( D ) OTHER INFORMATION: /note= "Xaa at position 91 is Ala, Pro, Ser, Thr, Phe, Leu, Asp, or His"

( i x ) FEATURE:
    ( A ) NAME/KEY: Modified-site
    ( B ) LOCATION: 92
    ( D ) OTHER INFORMATION: /note= "Xaa at position 92 is Pro, Phe, Arg, Ser, Lys, His, Ala, Gly, Ile, or Leu"

( i x ) FEATURE:
    ( A ) NAME/KEY: Modified-site
    ( B ) LOCATION: 93
    ( D ) OTHER INFORMATION: /note= "Xaa at position 93 is Thr, Asp, Ser, Asn, Pro, Ala, Leu, or Arg"

( i x ) FEATURE:
    ( A ) NAME/KEY: Modified-site
    ( B ) LOCATION: 94
    ( D ) OTHER INFORMATION: /note= "Xaa at position 94 is Arg, Ile, Ser, Glu, Leu, Val, Gln, Lys, His, Ala, or Pro"

( i x ) FEATURE:
    ( A ) NAME/KEY: Modified-site
    ( B ) LOCATION: 95
    ( D ) OTHER INFORMATION: /note= "Xaa at position 95 is His, Gln, Pro, Arg, Val, Leu, Gly, Thr, Asn, Lys, Ser, Ala, Trp, Phe, Ile, or Tyr"

( i x ) FEATURE:
    ( A ) NAME/KEY: Modified-site
    ( B ) LOCATION: 96
    ( D ) OTHER INFORMATION: /note= "Xaa at position 96 is Pro, Lys, Tyr, Gly, Ile, or Thr"

( i x ) FEATURE:
    ( A ) NAME/KEY: Modified-site
    ( B ) LOCATION: 97
    ( D ) OTHER INFORMATION: /note= "Xaa at position 97 is Ile, Val, Lys, Ala, or Asn"

( i x ) FEATURE:
    ( A ) NAME/KEY: Modified-site
    ( B ) LOCATION: 98
    ( D ) OTHER INFORMATION: /note= "Xaa at position 98 is His,
        Ile, Asn, Leu, Asp, Ala, Thr, Glu, Gln, Ser, Phe, Met,
        Val, Lys, Arg, Tyr, or Pro"

( i x ) FEATURE:
    ( A ) NAME/KEY: Modified-site
    ( B ) LOCATION: 99
    ( D ) OTHER INFORMATION: /note= "Xaa at position 99 is Ile,
        Leu, Arg, Asp, Val, Pro, Gln, Gly, Ser, Phe,
        or His"

( i x ) FEATURE:
    ( A ) NAME/KEY: Modified-site
    ( B ) LOCATION: 100
    ( D ) OTHER INFORMATION: /note= "Xaa at position 100 is
        Lys, Tyr, Leu, His, Arg, Ile, Ser, Gln, or Pro"

( i x ) FEATURE:
    ( A ) NAME/KEY: Modified-site
    ( B ) LOCATION: 101
    ( D ) OTHER INFORMATION: /note= "Xaa at position 101 is
        Asp, Pro, Met, Lys, His, Thr, Val, Tyr, Glu, Asn, Ser,
        Ala, Gly, Ile, Leu, or Gln"

( i x ) FEATURE:
    ( A ) NAME/KEY: Modified-site
    ( B ) LOCATION: 102
    ( D ) OTHER INFORMATION: /note= "Xaa at position 102 is Gly,
        Leu, Glu, Lys, Ser, Tyr, or Pro"

( i x ) FEATURE:
    ( A ) NAME/KEY: Modified-site
    ( B ) LOCATION: 103
    ( D ) OTHER INFORMATION: /note= "Xaa at position 103 is Asp,
        or Ser"

( i x ) FEATURE:
    ( A ) NAME/KEY: Modified-site
    ( B ) LOCATION: 104
    ( D ) OTHER INFORMATION: /note= "Xaa at position 104 is
        Trp, Val, Cys, Tyr, Thr, Met, Pro, Leu, Gln, Lys, Ala,
        Phe, or Gly"

( i x ) FEATURE:
    ( A ) NAME/KEY: Modified-site
    ( B ) LOCATION: 105
    ( D ) OTHER INFORMATION: /note= "Xaa at position 105 is
        Asn, Pro, Ala, Phe, Ser, Trp, Gln, Tyr, Leu, Lys, Ile,
        Asp, or His"

( i x ) FEATURE:
    ( A ) NAME/KEY: Modified-site
    ( B ) LOCATION: 106
    ( D ) OTHER INFORMATION: /note= "Xaa at position 106 is Glu,
        Ser, Ala, Lys, Thr, Ile, Gly, or Pro"

( i x ) FEATURE:
    ( A ) NAME/KEY: Modified-site
    ( B ) LOCATION: 108
    ( D ) OTHER INFORMATION: /note= "Xaa at position 108 is Arg,
        Lys, Asp, Leu, Thr, Ile, Gln, His, Ser, Ala, or Pro"

( i x ) FEATURE:
    ( A ) NAME/KEY: Modified-site
    ( B ) LOCATION: 109
    ( D ) OTHER INFORMATION: /note= "Xaa at position 109 is Arg,
        Thr, Pro, Glu, Tyr, Leu, Ser, or Gly"

( i x ) FEATURE:
    ( A ) NAME/KEY: Modified-site
    ( B ) LOCATION: 110
    ( D ) OTHER INFORMATION: /note= "Xaa at position 110 is Lys,
        Ala, Asn, Thr, Leu, Arg, Gln, His, Glu, Ser,
        or Trp"

( i x ) FEATURE:

(A) NAME/KEY: Modified-site
(B) LOCATION: 111
(D) OTHER INFORMATION: /note= "Xaa at position 111 is Leu,
    Ile, Arg, Asp, or Met"

(ix) FEATURE:
(A) NAME/KEY: Modified-site
(B) LOCATION: 112
(D) OTHER INFORMATION: /note= "Xaa at position 112 is Thr,
    Val, Gln, Tyr, Glu, His, Ser, or Phe"

(ix) FEATURE:
(A) NAME/KEY: Modified-site
(B) LOCATION: 113
(D) OTHER INFORMATION: /note= "Xaa at position 113 is Phe,
    Ser, Cys, His, Gly, Trp, Tyr, Asp, Lys, Leu, Ile, Val,
    or Asn"

(ix) FEATURE:
(A) NAME/KEY: Modified-site
(B) LOCATION: 114
(D) OTHER INFORMATION: /note= "Xaa at position 114 is Tyr,
    Cys, His, Ser, Trp, Arg, or Leu"

(ix) FEATURE:
(A) NAME/KEY: Modified-site
(B) LOCATION: 115
(D) OTHER INFORMATION: /note= "Xaa at position 115 is
    Leu, Asn, Val, Pro, Arg, Ala, His, Thr, Trp, or
    Met"

(ix) FEATURE:
(A) NAME/KEY: Modified-site
(B) LOCATION: 116
(D) OTHER INFORMATION: /note= "Xaa at position 116 is Lys,
    Leu, Pro, Thr, Met, Asp, Val, Glu, Arg, Trp, Ser,
    Asn, His, Ala, Tyr, Phe, Gln, or Ile"

(ix) FEATURE:
(A) NAME/KEY: Modified-site
(B) LOCATION: 117
(D) OTHER INFORMATION: /note= "Xaa at position 117 is Thr,
    Ser, Asn, Ile, Trp, Lys, or Pro"

(ix) FEATURE:
(A) NAME/KEY: Modified-site
(B) LOCATION: 118
(D) OTHER INFORMATION: /note= "Xaa at position 118 is Leu,
    Ser, Pro, Ala, Glu, Cys, Asp, or Tyr"

(ix) FEATURE:
(A) NAME/KEY: Modified-site
(B) LOCATION: 119
(D) OTHER INFORMATION: /note= "Xaa at position 119 is Glu,
    Ser, Lys, Pro, Leu, Thr, Tyr, or Arg"

(ix) FEATURE:
(A) NAME/KEY: Modified-site
(B) LOCATION: 120
(D) OTHER INFORMATION: /note= "Xaa at position 120 is Asn,
    Ala, Pro, Leu, His, Val, or Gln"

(ix) FEATURE:
(A) NAME/KEY: Modified-site
(B) LOCATION: 121
(D) OTHER INFORMATION: /note= "Xaa at position 121 is Ala,
    Ser, Ile, Asn, Pro, Lys, Asp, or Gly"

(ix) FEATURE:
(A) NAME/KEY: Modified-site
(B) LOCATION: 122
(D) OTHER INFORMATION: /note= "Xaa at position 122 is
    Gln, Ser, Met, Trp, Arg, Phe, Pro, His, Ile, Tyr,
    or Cys"

(ix) FEATURE:
(A) NAME/KEY: Modified-site
(B) LOCATION: 123
(D) OTHER INFORMATION: /note= "Xaa at position 123 is Ala,
    Met, Glu, His, Ser, Pro, Tyr, or Leu"

(xi) SEQUENCE DESCRIPTION: SEQ ID NO:1:

| Ala | Pro | Met | Thr | Gln | Thr | Thr | Ser | Leu | Lys | Thr | Ser | Trp | Val | Asn | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|
|     |     |     | 20  |     |     |     |     | 25  |     |     |     |     | 30  |     |

| Xaa | Xaa | Xaa | Xaa | Xaa | Xaa | Asn | Xaa | Xaa | Xaa | Xaa | Xaa | Xaa | Xaa | Xaa |
|-----|-----|-----|-----|-----|-----|-----|-----|-----|-----|-----|-----|-----|-----|-----|
|     |     | 35  |     |     |     |     | 40  |     |     |     |     | 45  |     |     |

| Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|
|     | 50  |     |     |     |     | 55  |     |     |     |     | 60  |     |     |     |

| Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|
| 65  |     |     |     |     | 70  |     |     |     |     | 75  |     |     |     | 80  |

| Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|
|     |     |     |     | 85  |     |     |     |     | 90  |     |     |     |     | 95  |

| Xaa | Xaa | Xaa | Xaa | Xaa | Xaa | Xaa | Xaa | Xaa | Xaa | Phe | Xaa | Xaa | Xaa | Xaa | Xaa |
|-----|-----|-----|-----|-----|-----|-----|-----|-----|-----|-----|-----|-----|-----|-----|-----|
|     |     |     | 100 |     |     |     |     | 105 |     |     |     |     |     | 110 |     |

| Xaa | Xaa | Xaa | Xaa | Xaa | Xaa | Xaa | Xaa | Xaa | Xaa | Xaa | Gln | Gln | Thr | Thr | Leu |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Ser | Leu | Ala | Ile | Phe |
|-----|-----|-----|-----|-----|
|     |     | 130 |     |     |

(2) INFORMATION FOR SEQ ID NO:2:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Met, Gly, Asp, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 19
        (D) OTHER INFORMATION: /note= "Xaa at position 19 is Met
            or Ile"

(ix) FEATURE:
        (A) NAME/KEY: Modified-site
        (B) LOCATION: 21
        (D) OTHER INFORMATION: /note="Xaa at position 21 is Asp
            or Glu"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 24
        (D) OTHER INFORMATION: /note= "Xaa at position 24 is Ile, Val, or Leu"

( i x ) FEATURE:
    ( A ) NAME/KEY: Modified-site
    ( B ) LOCATION: 25
    ( D ) OTHER INFORMATION: /note= "Xaa at position 25 is Thr,
        His, Gln, or Ala"

( i x ) FEATURE:
    ( A ) NAME/KEY: Modified-site
    ( B ) LOCATION: 26
    ( D ) OTHER INFORMATION: /note= "Xaa at position 26 is His
        or Ala"

( i x ) FEATURE:
    ( A ) NAME/KEY: Modified-site
    ( B ) LOCATION: 29
    ( D ) OTHER INFORMATION: /note= "Xaa at position 29 is Gln,
        Asn, or Val"

( i x ) FEATURE:
    ( A ) NAME/KEY: Modified-site
    ( B ) LOCATION: 30
    ( D ) OTHER INFORMATION: /note= "Xaa at position 30 is Pro,
        Gly, or Gln"

( i x ) FEATURE:
    ( A ) NAME/KEY: Modified-site
    ( B ) LOCATION: 31
    ( D ) OTHER INFORMATION: /note= "Xaa at position 31 is Pro,
        Asp, Gly, or Gln"

( i x ) FEATURE:
    ( A ) NAME/KEY: Modified-site
    ( B ) LOCATION: 32
    ( D ) OTHER INFORMATION: /note= "Xaa at position 32 is Leu,
        Arg, Gln, Asn, Gly, Ala, or Glu"

( i x ) FEATURE:
    ( A ) NAME/KEY: Modified-site
    ( B ) LOCATION: 33
    ( D ) OTHER INFORMATION: /note= "Xaa at position 33 is Pro
        or Glu"

( i x ) FEATURE:
    ( A ) NAME/KEY: Modified-site
    ( B ) LOCATION: 34
    ( D ) OTHER INFORMATION: /note= "Xaa at position 34 is Leu,
        Val, Gly, Ser, Lys, Ala, Arg, Gln, Glu, Ile, Phe,
        Thr, or Met"

( i x ) FEATURE:
    ( A ) NAME/KEY: Modified-site
    ( B ) LOCATION: 35
    ( D ) OTHER INFORMATION: /note= "Xaa at position 35 is Leu,
        Ala, Asn, Pro, Gln, or Val"

( i x ) FEATURE:
    ( A ) NAME/KEY: Modified-site
    ( B ) LOCATION: 37
    ( D ) OTHER INFORMATION: /note= "Xaa at position 37 is Phe,
        Ser, Pro, or Trp"

( i x ) FEATURE:
    ( A ) NAME/KEY: Modified-site
    ( B ) LOCATION: 38
    ( D ) OTHER INFORMATION: /note="Xaa at position 38 is Asn
        or Ala"

( i x ) FEATURE:
    ( A ) NAME/KEY: Modified-site
    ( B ) LOCATION: 42
    ( D ) OTHER INFORMATION: /note= "Xaa at position 42 is Gly,
        Asp, Ser, Cys, Ala, Asn, Ile, Leu, Met, Tyr,
        or Arg"

( i x ) FEATURE:
    ( A ) NAME/KEY: Modified-site
    ( B ) LOCATION: 44
    ( D ) OTHER INFORMATION: /note="Xaa at position 44 is Asp or Glu"

( i x ) FEATURE:
    ( A ) NAME/KEY: Modified-site
    ( B ) LOCATION: 45
    ( D ) OTHER INFORMATION: /note= "Xaa at position 45 is Gln,
        Val, Met, Leu, Thr, Ala, Asn, Glu, Ser, or Lys"

( i x ) FEATURE:
    ( A ) NAME/KEY: Modified-site
    ( B ) LOCATION: 46
    ( D ) OTHER INFORMATION: /note= "Xaa at position 46 is Asp,
        Phe, Ser, Thr, Ala, Asn, Gln, Glu, His, Ile,
        Lys, Tyr, Val, or Cys"

( i x ) FEATURE:
    ( A ) NAME/KEY: Modified-site
    ( B ) LOCATION: 50
    ( D ) OTHER INFORMATION: /note= "Xaa at position 50 is Glu,
        Ala, Asn, Ser, or Asp"

( i x ) FEATURE:
    ( A ) NAME/KEY: Modified-site
    ( B ) LOCATION: 51
    ( D ) OTHER INFORMATION: /note= "Xaa at position 51 is Asn,
        Arg, Met, Pro, Ser, Thr, or His"

( i x ) FEATURE:
    ( A ) NAME/KEY: Modified-site
    ( B ) LOCATION: 54
    ( D ) OTHER INFORMATION: /note="Xaa at position 54 is Arg
        or Ala"

( i x ) FEATURE:
    ( A ) NAME/KEY: Modified-site
    ( B ) LOCATION: 55
    ( D ) OTHER INFORMATION: /note= "Xaa at position 55 is Arg,
        Thr, Val, Leu, or Gly"

( i x ) FEATURE:
    ( A ) NAME/KEY: Modified-site
    ( B ) LOCATION: 56
    ( D ) OTHER INFORMATION: /note= "Xaa at position 56 is Pro,
        Gly, Ser, Gln, Ala, Arg, Asn, Glu, Leu, Thr, Val,
        or Lys"

( i x ) FEATURE:
    ( A ) NAME/KEY: Modified-site
    ( B ) LOCATION: 60
    ( D ) OTHER INFORMATION: /note= "Xaa at position 60 is Ala
        or Ser"

( i x ) FEATURE:
    ( A ) NAME/KEY: Modified-site
    ( B ) LOCATION: 62
    ( D ) OTHER INFORMATION: /note= "Xaa at position 62 is Asn,
        Pro, Thr, or Ile"

( i x ) FEATURE:
    ( A ) NAME/KEY: Modified-site
    ( B ) LOCATION: 63
    ( D ) OTHER INFORMATION: /note= "Xaa at position 63 is Arg
        or Lys"

( i x ) FEATURE:
    ( A ) NAME/KEY: Modified-site
    ( B ) LOCATION: 64
    ( D ) OTHER INFORMATION: /note= "Xaa at position 64 is Ala
        or Asn"

( i x ) FEATURE:
    ( A ) NAME/KEY: Modified-site
    ( B ) LOCATION: 65
    ( D ) OTHER INFORMATION: /note= "Xaa at position 65 is Val
        or Thr"

( i x ) FEATURE:
    ( A ) NAME/KEY: Modified-site
    ( B ) LOCATION: 66
    ( D ) OTHER INFORMATION: /note= "Xaa at position 66 is Lys or Arg"

( i x ) FEATURE:
    ( A ) NAME/KEY: Modified-site
    ( B ) LOCATION: 67
    ( D ) OTHER INFORMATION: /note= "Xaa at position 67 is Ser
        Phe or His"

( i x ) FEATURE:
    ( A ) NAME/KEY: Modified-site
    ( B ) LOCATION: 68
    ( D ) OTHER INFORMATION: /note= "Xaa at position 68 is Leu,
        Ile, Phe, or His"

( i x ) FEATURE:
    ( A ) NAME/KEY: Modified-site
    ( B ) LOCATION: 69
    ( D ) OTHER INFORMATION: /note= "Xaa at position 69 is Gln,
        Ala, Pro, Thr, Glu, Arg, or Gly"

( i x ) FEATURE:
    ( A ) NAME/KEY: Modified-site
    ( B ) LOCATION: 71
    ( D ) OTHER INFORMATION: /note= "Xaa at position 71 is Ala,
        Pro, or Arg"

( i x ) FEATURE:
    ( A ) NAME/KEY: Modified-site
    ( B ) LOCATION: 72
    ( D ) OTHER INFORMATION: /note= "Xaa at position 72 is Ser,
        Glu, Arg, or Asp"

( i x ) FEATURE:
    ( A ) NAME/KEY: Modified-site
    ( B ) LOCATION: 73
    ( D ) OTHER INFORMATION: /note= "Xaa at position 73 is Ala
        or Leu"

( i x ) FEATURE:
    ( A ) NAME/KEY: Modified-site
    ( B ) LOCATION: 76
    ( D ) OTHER INFORMATION: /note= "Xaa at position 76 is Ser,
        Val, Ala, Asn, Glu, Pro, or Gly"

( i x ) FEATURE:
    ( A ) NAME/KEY: Modified-site
    ( B ) LOCATION: 77
    ( D ) OTHER INFORMATION: /note= "Xaa at position 77 is Ile
        or Leu"

( i x ) FEATURE:
    ( A ) NAME/KEY: Modified-site
    ( B ) LOCATION: 79
    ( D ) OTHER INFORMATION: /note= "Xaa at position 79 is
        Lys, Thr, Gly, Asn, Met, Arg, Ile, Gly, or Asp"

( i x ) FEATURE:
    ( A ) NAME/KEY: Modified-site
    ( B ) LOCATION: 80
    ( D ) OTHER INFORMATION: /note= "Xaa at position 80 is Asn,
        Gly, Glu, or Arg"

( i x ) FEATURE:
    ( A ) NAME/KEY: Modified-site
    ( B ) LOCATION: 82
    ( D ) OTHER INFORMATION: /note= "Xaa at position 82 is Leu,
        Gln, Trp, Arg, Asp, Ala, Asn, Glu, His, Ile,
        Met, Phe, Ser, Thr, Tyr, or Val"

( i x ) FEATURE:
    ( A ) NAME/KEY: Modified-site
    ( B ) LOCATION: 83
    ( D ) OTHER INFORMATION: /note= "Xaa at position 83 is Pro
        or Thr"

( i x ) FEATURE:
    ( A ) NAME/KEY: Modified-site
    ( B ) LOCATION: 85
    ( D ) OTHER INFORMATION: /note= "Xaa at position 85 is Leu
        or Val"

( i x ) FEATURE:
    ( A ) NAME/KEY: Modified-site
    ( B ) LOCATION: 87
    ( D ) OTHER INFORMATION: /note= "Xaa at position 87 is Leu
        or Ser"

( i x ) FEATURE:
    ( A ) NAME/KEY: Modified-site
    ( B ) LOCATION: 88
    ( D ) OTHER INFORMATION: /note= "Xaa at position 88 is Ala
        or Trp"

( i x ) FEATURE:
    ( A ) NAME/KEY: Modified-site
    ( B ) LOCATION: 91
    ( D ) OTHER INFORMATION: /note= "Xaa at position 91 is Ala
        or Pro"

( i x ) FEATURE:
    ( A ) NAME/KEY: Modified-site
    ( B ) LOCATION: 93
    ( D ) OTHER INFORMATION: /note= "Xaa at position 93 is Thr,
        Asp, Ser, Pro, Ala, Leu, or Arg"

( i x ) FEATURE:
    ( A ) NAME/KEY: Modified-site
    ( B ) LOCATION: 95
    ( D ) OTHER INFORMATION: /note= "Xaa at position 95 is His,
        Pro, Arg, Val, Leu, Gly, Asn, Phe, Ser, or Thr"

( i x ) FEATURE:
    ( A ) NAME/KEY: Modified-site
    ( B ) LOCATION: 96
    ( D ) OTHER INFORMATION: /note= "Xaa at position 96 is Pro
        or Tyr"

( i x ) FEATURE:
    ( A ) NAME/KEY: Modified-site
    ( B ) LOCATION: 97
    ( D ) OTHER INFORMATION: /note= "Xaa at position 97 is Ile
        or Val"

( i x ) FEATURE:
    ( A ) NAME/KEY: Modified-site
    ( B ) LOCATION: 98
    ( D ) OTHER INFORMATION: /note= "Xaa at position 98 is His,
        Ile, Asn, Leu, Ala, Thr, Arg, Gln, Lys,
        Met, Ser, Tyr, Val, or Pro"

( i x ) FEATURE:
    ( A ) NAME/KEY: Modified-site
    ( B ) LOCATION: 99
    ( D ) OTHER INFORMATION: /note= "Xaa at position 99 is Ile,
        Leu, or Val"

( i x ) FEATURE:
    ( A ) NAME/KEY: Modified-site
    ( B ) LOCATION: 100
    ( D ) OTHER INFORMATION: /note= "Xaa at position 100 is Lys,
        Arg, Ile, Gln, Pro, or Ser"

( i x ) FEATURE:
    ( A ) NAME/KEY: Modified-site
    ( B ) LOCATION: 101
    ( D ) OTHER INFORMATION: /note= "Xaa at position 101 is Asp,
        Pro, Met, Lys, His, Thr, Pro, Asn, Ile, Leu, or Tyr"

( i x ) FEATURE:
    ( A ) NAME/KEY: Modified-site
    ( B ) LOCATION: 104
    ( D ) OTHER INFORMATION: /note= "Xaa at position 104 is Trp
        or Leu"

( i x ) FEATURE:
    ( A ) NAME/KEY: Modified-site
    ( B ) LOCATION: 105
    ( D ) OTHER INFORMATION: /note= "Xaa at position 105 is
        Asn, Pro, Ala, Ser, Trp, Gln, Tyr, Leu, Lys, Ile,
        Asp, or His"

-continued ( i x ) FEATURE:
    ( A ) NAME/KEY: Modified-site
    ( B ) LOCATION: 106
    ( D ) OTHER INFORMATION: /note= "Xaa at position 106 is Glu
        or Gly"

( i x ) FEATURE:
    ( A ) NAME/KEY: Modified-site
    ( B ) LOCATION: 108
    ( D ) OTHER INFORMATION: /note="Xaa at position 108 is Arg,
        Ala, or Ser"

( i x ) FEATURE:
    ( A ) NAME/KEY: Modified-site
    ( B ) LOCATION: 109
    ( D ) OTHER INFORMATION: /note= "Xaa at position 109 is Arg,
        Thr, Glu, Leu, or Ser"

( i x ) FEATURE:
    ( A ) NAME/KEY: Modified-site
    ( B ) LOCATION: 112
    ( D ) OTHER INFORMATION: /note= "Xaa at position 112 is Thr,
        Val, or Gln"

( i x ) FEATURE:
    ( A ) NAME/KEY: Modified-site
    ( B ) LOCATION: 114
    ( D ) OTHER INFORMATION: /note= "Xaa at position 114 is Tyr
        or Trp"

( i x ) FEATURE:
    ( A ) NAME/KEY: Modified-site
    ( B ) LOCATION: 115
    ( D ) OTHER INFORMATION: /note= "Xaa at position 115 is Leu
        or Ala"

( i x ) FEATURE:
    ( A ) NAME/KEY: Modified-site
    ( B ) LOCATION: 116
    ( D ) OTHER INFORMATION: /note= "Xaa at position 116 is Lys,
        Thr, Val, Trp, Ser, Ala, His, Met, Phe, Tyr, or Ile"

( i x ) FEATURE:
    ( A ) NAME/KEY: Modified-site
    ( B ) LOCATION: 117
    ( D ) OTHER INFORMATION: /note= "Xaa at position 117 is Thr
        or Ser"

( i x ) FEATURE:
    ( A ) NAME/KEY: Modified-site
    ( B ) LOCATION: 120
    ( D ) OTHER INFORMATION: /note= "Xaa at position 120 is Asn,
        Pro, Leu, His, Val, or Gln"

( i x ) FEATURE:
    ( A ) NAME/KEY: Modified-site
    ( B ) LOCATION: 121
    ( D ) OTHER INFORMATION: /note= "Xaa at position 121 is Ala,
        Ser, Ile, Asn, Pro, Asp, or Gly"

( i x ) FEATURE:
    ( A ) NAME/KEY: Modified-site
    ( B ) LOCATION: 122
    ( D ) OTHER INFORMATION: /note= "Xaa at position 122 is
        Gln, Ser, Met, Trp, Arg, Phe, Pro, His, Ile, Tyr,
        or Cys"

( i x ) FEATURE:
    ( A ) NAME/KEY: Modified-site
    ( B ) LOCATION: 123
    ( D ) OTHER INFORMATION: /note= "Xaa at position 123 is Ala,
        Met, Glu, His, Ser, Pro, Tyr, or Leu"

( x i ) SEQUENCE DESCRIPTION: SEQ ID NO:2:

```
Ala  Pro  Met  Thr  Gln  Thr  Thr  Ser  Leu  Lys  Thr  Ser  Trp  Val  Asn  Cys
 1                   5                        10                        15

Xaa  Xaa  Xaa  Ile  Xaa  Glu  Xaa  Xaa  Xaa  Xaa  Leu  Lys  Xaa  Xaa  Xaa  Xaa
```

```
                              20                    25                     30
        Xaa  Xaa  Xaa  Asp  Xaa  Xaa  Asn  Leu  Asn  Xaa  Glu  Xaa  Xaa  Xaa  Ile  Leu
                  35                      40                      45

Met  Xaa  Xaa  Asn  Leu  Xaa  Xaa  Xaa  Asn  Leu  Glu  Xaa  Phe  Xaa  Xaa  Xaa
             50                      55                      60

Xaa  Xaa  Xaa  Xaa  Xaa  Asn  Xaa  Xaa  Xaa  Ile  Glu  Xaa  Xaa  Leu  Xaa  Xaa
        65                      70                      75                           80

Leu  Xaa  Xaa  Cys  Xaa  Pro  Xaa  Xaa  Thr  Ala  Xaa  Pro  Xaa  Arg  Xaa  Xaa
                       85                           90                           95

Xaa  Xaa  Xaa  Xaa  Xaa  Gly  Asp  Xaa  Xaa  Xaa  Phe  Xaa  Xaa  Lys  Leu  Xaa
                  100                      105                      110

Phe  Xaa  Xaa  Xaa  Xaa  Leu  Glu  Xaa  Xaa  Xaa  Xaa  Gln  Gln  Thr  Thr  Leu
                  115                      120                      125

Ser  Leu  Ala  Ile  Phe
        130
```

( 2 ) INFORMATION FOR SEQ ID NO:3:

( i ) SEQUENCE CHARACTERISTICS:
            ( A ) LENGTH: 133 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note= "Met- may or may not precede
                  the amino acid in position 1"

( i x ) FEATURE:
            ( A ) NAME/KEY: Modified-site
            ( B ) LOCATION: 17
            ( D ) OTHER INFORMATION: /note= "Xaa at position 17 is Ser,
                  Gly, Asp, or Gln"

( i x ) FEATURE:
            ( A ) NAME/KEY: Modified-site
            ( B ) LOCATION: 18
            ( D ) OTHER INFORMATION: /note= "Xaa at position 18 is Asn,
                  His, or Ile"

( i x ) FEATURE:
            ( A ) NAME/KEY: Modified-site
            ( B ) LOCATION: 23
            ( D ) OTHER INFORMATION: /note= "Xaa at position 23 is Ile,
                  Ala, Leu, or Gly"

( i x ) FEATURE:
            ( A ) NAME/KEY: Modified-site
            ( B ) LOCATION: 25
            ( D ) OTHER INFORMATION: /note= "Xaa at position 25 is Thr,
                  His, or Gln"

( i x ) FEATURE:
            ( A ) NAME/KEY: Modified-site
            ( B ) LOCATION: 26
            ( D ) OTHER INFORMATION: /note= "Xaa at position 26 is His
                  or Ala"

( i x ) FEATURE:
            ( A ) NAME/KEY: Modified-site
            ( B ) LOCATION: 29
            ( D ) OTHER INFORMATION: /note="Xaa at position 29 is Gln
                  or Asn"

( i x ) FEATURE:
            ( A ) NAME/KEY: Modified-site
            ( B ) LOCATION: 30
            ( D ) OTHER INFORMATION: /note= "Xaa at position 30 is Pro
                  or Gly"

( i x ) FEATURE:
  ( A ) NAME/KEY: Modified-site
  ( B ) LOCATION: 32
  ( D ) OTHER INFORMATION: /note= "Xaa at position 32 is Leu,
    Arg, Asn, or Ala"

( i x ) FEATURE:
  ( A ) NAME/KEY: Modified-site
  ( B ) LOCATION: 34
  ( D ) OTHER INFORMATION: /note= "Xaa at position 34 is Leu,
    Val, Ser, Ala, Arg, Gln, Glu, Ile, Phe, Thr, or Met"

( i x ) FEATURE:
  ( A ) NAME/KEY: Modified-site
  ( B ) LOCATION: 35
  ( D ) OTHER INFORMATION: /note= "Xaa at position 35 is Leu,
    Ala, Asn, or Pro"

( i x ) FEATURE:
  ( A ) NAME/KEY: Modified-site
  ( B ) LOCATION: 38
  ( D ) OTHER INFORMATION: /note= "Xaa at position 38 is Asn
    or Ala"

( i x ) FEATURE:
  ( A ) NAME/KEY: Modified-site
  ( B ) LOCATION: 42
  ( D ) OTHER INFORMATION: /note= "Xaa at position 42 is Gly,
    Asp, Ser, Ala, Asn, Ile, Leu, Met, Tyr, or Arg"

( i x ) FEATURE:
  ( A ) NAME/KEY: Modified-site
  ( B ) LOCATION: 45
  ( D ) OTHER INFORMATION: /note= "Xaa at position 45 is Gln,
    Val, Met, Leu, Ala, Asn, Glu, or Lys"

( i x ) FEATURE:
  ( A ) NAME/KEY: Modified-site
  ( B ) LOCATION: 46
  ( D ) OTHER INFORMATION: /note= "Xaa at position 46 is Asp,
    Phe, Ser, Gln, Glu, His, Val, or Thr"

( i x ) FEATURE:
  ( A ) NAME/KEY: Modified-site
  ( B ) LOCATION: 50
  ( D ) OTHER INFORMATION: /note= "Xaa at position 50 is Glu,
    Asn, Ser, or Asp"

( i x ) FEATURE:
  ( A ) NAME/KEY: Modified-site
  ( B ) LOCATION: 51
  ( D ) OTHER INFORMATION: /note= "Xaa at position 51 is Asn,
    Arg, Pro, Thr, or His"

( i x ) FEATURE:
  ( A ) NAME/KEY: Modified-site
  ( B ) LOCATION: 55
  ( D ) OTHER INFORMATION: /note= "Xaa at position 55 is Arg,
    Leu, or Gly"

( i x ) FEATURE:
  ( A ) NAME/KEY: Modified-site
  ( B ) LOCATION: 56
  ( D ) OTHER INFORMATION: /note= "Xaa at position 56 is Pro,
    Gly, Ser, Ala, Asn, Val, Leu, or Gln"

( i x ) FEATURE:
  ( A ) NAME/KEY: Modified-site
  ( B ) LOCATION: 62
  ( D ) OTHER INFORMATION: /note= "Xaa at position 62 is Asn,
    Pro, or Thr"

( i x ) FEATURE:
  ( A ) NAME/KEY: Modified-site
  ( B ) LOCATION: 64
  ( D ) OTHER INFORMATION: /note= "Xaa at position 64 is Ala
    or Asn"

( i x ) FEATURE:

(A) NAME/KEY: Modified-site
(B) LOCATION: 65
(D) OTHER INFORMATION: /note= "Xaa at position 65 is Val
or Thr"

(ix) FEATURE:
(A) NAME/KEY: Modified-site
(B) LOCATION: 67
(D) OTHER INFORMATION: /note= "Xaa at position 67 is Ser
or Phe"

(ix) FEATURE:
(A) NAME/KEY: Modified-site
(B) LOCATION: 68
(D) OTHER INFORMATION: /note= "Xaa at position 68 is Leu
or Phe"

(ix) FEATURE:
(A) NAME/KEY: Modified-site
(B) LOCATION: 69
(D) OTHER INFORMATION: /note= "Xaa at position 69 is Gln,
Ala, Glu, or Arg"

(ix) FEATURE:
(A) NAME/KEY: Modified-site
(B) LOCATION: 76
(D) OTHER INFORMATION: /note= "Xaa at position 76 is Ser,
Val, Asn, Pro, or Gly"

(ix) FEATURE:
(A) NAME/KEY: Modified-site
(B) LOCATION: 77
(D) OTHER INFORMATION: /note= "Xaa at position 77 is Ile
or Leu"

(ix) FEATURE:
(A) NAME/KEY: Modified-site
(B) LOCATION: 79
(D) OTHER INFORMATION: /note= "Xaa at position 79 is Lys,
Asn, Met, Arg, Ile, or Gly"

(ix) FEATURE:
(A) NAME/KEY: Modified-site
(B) LOCATION: 80
(D) OTHER INFORMATION: /note= "Xaa at position 80 is Asn,
Gly, Glu, or Arg"

(ix) FEATURE:
(A) NAME/KEY: Modified-site
(B) LOCATION: 82
(D) OTHER INFORMATION: /note= "Xaa at position 82 is Leu,
Gln, Trp, Arg, Asp, Asn, Glu, His, Met, Phe, Ser,
Thr, Tyr, or Val"

(ix) FEATURE:
(A) NAME/KEY: Modified-site
(B) LOCATION: 87
(D) OTHER INFORMATION: /note= "Xaa at position 87 is Leu
or Ser"

(ix) FEATURE:
(A) NAME/KEY: Modified-site
(B) LOCATION: 88
(D) OTHER INFORMATION: /note= "Xaa at position 88 is Ala
or Trp"

(ix) FEATURE:
(A) NAME/KEY: Modified-site
(B) LOCATION: 91
(D) OTHER INFORMATION: /note= "Xaa at position 91 is Ala
or Pro"

(ix) FEATURE:
(A) NAME/KEY: Modified-site
(B) LOCATION: 93
(D) OTHER INFORMATION: /note= "Xaa at position 93 is Thr,
Asp, or Ala"

(ix) FEATURE:
(A) NAME/KEY: Modified-site ( B ) LOCATION: 95
( D ) OTHER INFORMATION: /note= "Xaa at position 95 is His,
Pro, Arg, Val, Gly, Asn, Ser, or Thr"

( i x ) FEATURE:
( A ) NAME/KEY: Modified-site
( B ) LOCATION: 98
( D ) OTHER INFORMATION: /note= "Xaa at position 98 is His,
Ile, Asn, Ala, Thr, Gln, Glu, Lys, Met, Ser, Tyr,
Val, or Leu"

( i x ) FEATURE:
( A ) NAME/KEY: Modified-site
( B ) LOCATION: 99
( D ) OTHER INFORMATION: /note= "Xaa at position 99 is Ile
or Leu"

( i x ) FEATURE:
( A ) NAME/KEY: Modified-site
( B ) LOCATION: 100
( D ) OTHER INFORMATION: /note= "Xaa at position 100 is Lys
or Arg"

( i x ) FEATURE:
( A ) NAME/KEY: Modified-site
( B ) LOCATION: 101
( D ) OTHER INFORMATION: /note= "Xaa at position 101 is Asp,
Pro, Met, Lys, Thr, His, Asn, Ile, Leu, or Tyr"

( i x ) FEATURE:
( A ) NAME/KEY: Modified-site
( B ) LOCATION: 105
( D ) OTHER INFORMATION: /note= "Xaa at position 105 is Asn,
Pro, Ser, Ile, or Asp"

( i x ) FEATURE:
( A ) NAME/KEY: Modified-site
( B ) LOCATION: 108
( D ) OTHER INFORMATION: /note="Xaa at position 108 is Arg,
Ala, or Ser"

( i x ) FEATURE:
( A ) NAME/KEY: Modified-site
( B ) LOCATION: 109
( D ) OTHER INFORMATION: /note= "Xaa at position 109 is Arg,
Thr, Glu, Leu, or Ser"

( i x ) FEATURE:
( A ) NAME/KEY: Modified-site
( B ) LOCATION: 112
( D ) OTHER INFORMATION: /note= "Xaa at position 112 is Thr
or Gln"

( i x ) FEATURE:
( A ) NAME/KEY: Modified-site
( B ) LOCATION: 116
( D ) OTHER INFORMATION: /note= "Xaa at position 116 is Lys,
Val, Trp, Ala, His, Phe, Tyr, or Ile"

( i x ) FEATURE:
( A ) NAME/KEY: Modified-site
( B ) LOCATION: 117
( D ) OTHER INFORMATION: /note= "Xaa at position 117 is Thr
or Ser"

( i x ) FEATURE:
( A ) NAME/KEY: Modified-site
( B ) LOCATION: 120
( D ) OTHER INFORMATION: /note= "Xaa at position 120 is Asn,
Pro, Leu, His, Val, or Gln"

( i x ) FEATURE:
( A ) NAME/KEY: Modified-site
( B ) LOCATION: 121
( D ) OTHER INFORMATION: /note= "Xaa at position 121 is Ala,
Ser, Ile, Pro, or Asp"

( i x ) FEATURE:
( A ) NAME/KEY: Modified-site
( B ) LOCATION: 122

(D) OTHER INFORMATION: /note= "Xaa at position 122 is Gln,
    Met, Trp, Phe, Pro, His, Ile, or Tyr"

(ix) FEATURE:
     (A) NAME/KEY: Modified-site
     (B) LOCATION: 123
     (D) OTHER INFORMATION: /note= "Xaa at position 123 is Ala,
         Met, Glu, Ser, or Leu"

(xi) SEQUENCE DESCRIPTION: SEQ ID NO:3:

| Ala | Pro | Met | Thr | Gln | Thr | Thr | Ser | Leu | Lys | Thr | Ser | Trp | Val | Asn | Cys |
|---|---|---|---|---|---|---|---|---|---|---|---|---|---|---|---|
| 1 | | | | 5 | | | | | 10 | | | | | 15 | |
| Xaa | Xaa | Met | Ile | Asp | Glu | Xaa | Ile | Xaa | Xaa | Leu | Lys | Xaa | Xaa | Pro | Xaa |
| | | | 20 | | | | 25 | | | | | | 30 | | |
| Pro | Xaa | Xaa | Asp | Phe | Xaa | Asn | Leu | Asn | Xaa | Glu | Asp | Xaa | Xaa | Ile | Leu |
| | | 35 | | | | | 40 | | | | | 45 | | | |
| Met | Xaa | Xaa | Asn | Leu | Arg | Xaa | Xaa | Asn | Leu | Glu | Ala | Phe | Xaa | Arg | Xaa |
| | 50 | | | | | 55 | | | | | 60 | | | | |
| Xaa | Lys | Xaa | Xaa | Xaa | Asn | Ala | Ser | Ala | Ile | Glu | Xaa | Xaa | Leu | Xaa | Xaa |
| 65 | | | | | 70 | | | | | 75 | | | | | 80 |
| Leu | Xaa | Pro | Cys | Leu | Pro | Xaa | Xaa | Thr | Ala | Xaa | Pro | Xaa | Arg | Xaa | Pro |
| | | | | 85 | | | | | 90 | | | | | 95 | |
| Ile | Xaa | Xaa | Xaa | Xaa | Gly | Asp | Trp | Xaa | Glu | Phe | Xaa | Xaa | Lys | Leu | Xaa |
| | | | 100 | | | | | 105 | | | | | 110 | | |
| Phe | Tyr | Leu | Xaa | Xaa | Leu | Glu | Xaa | Xaa | Xaa | Xaa | Gln | Gln | Thr | Thr | Leu |
| | | 115 | | | | | 120 | | | | | 125 | | | |
| Ser | Leu | Ala | Ile | Phe | | | | | | | | | | | |
| | 130 | | | | | | | | | | | | | | |

(2) INFORMATION FOR SEQ ID NO:4:

(i) SEQUENCE CHARACTERISTICS:
    (A) LENGTH: 111 amino acids
    (B) TYPE: amino acid
    (D) TOPOLOGY: linear (ii) MOLECULE TYPE: peptide (ix) FEATURE:
     (A) NAME/KEY: Modified-site
     (B) LOCATION: 1
     (D) OTHER INFORMATION: /note= "Met- or Met-Ala- may or may
         not precede the amino acid in position 1"

(ix) FEATURE:
     (A) NAME/KEY: Modified-site
     (B) LOCATION: 3
     (D) OTHER INFORMATION: /note= "Xaa at position 3 is Ser,
         Lys, Gly, Asp, Met, Gln, or Arg"

(ix) FEATURE:
     (A) NAME/KEY: Modified-site
     (B) LOCATION: 4
     (D) OTHER INFORMATION: /note= "Xaa at position 4 is Asn,
         His, Leu, Ile, Phe, Arg, or Gln"

(ix) FEATURE:
     (A) NAME/KEY: Modified-site
     (B) LOCATION: 5
     (D) OTHER INFORMATION: /note= "Xaa at position 5 is Met,
         Phe, Ile, Arg, Gly, Ala, or Cys"

(ix) FEATURE:
     (A) NAME/KEY: Modified-site
     (B) LOCATION: 6
     (D) OTHER INFORMATION: /note= "Xaa at position 6 is Ile,
         Cys, Gln, Glu, Arg, Pro, or Ala"

(ix) FEATURE:
     (A) NAME/KEY: Modified-site

-continued (B) LOCATION: 7
                (D) OTHER INFORMATION: /note= "Xaa at position 7 is Asp,
                    Phe, Lys, Arg, Ala, Gly, Glu, Gln, Asn, Thr, Ser,
                    or Val"

(ix) FEATURE:
                (A) NAME/KEY: Modified-site
                (B) LOCATION: 8
                (D) OTHER INFORMATION: /note= "Xaa at position 8 is Glu,
                    Trp, Pro, Ser, Ala, His, Asp, Asn, Gln, Leu, Val,
                    or Gly"

(ix) FEATURE:
                (A) NAME/KEY: Modified-site
                (B) LOCATION: 9
                (D) OTHER INFORMATION: /note= "Xaa at position 9 is
                    Ile, Val, Ala, Leu, Gly, Trp, Lys, Phe, Ser
                    or Arg"

(ix) FEATURE:
                (A) NAME/KEY: Modified-site
                (B) LOCATION: 10
                (D) OTHER INFORMATION: /note= "Xaa at position 10 is Ile,
                    Gly, Val, Arg, Ser, Phe, or Leu"

(ix) FEATURE:
                (A) NAME/KEY: Modified-site
                (B) LOCATION: 11
                (D) OTHER INFORMATION: /note= "Xaa at position 11 is Thr,
                    His, Gly, Gln, Arg, Pro, or Ala"

(ix) FEATURE:
                (A) NAME/KEY: Modified-site
                (B) LOCATION: 12
                (D) OTHER INFORMATION: /note= "Xaa at position 12 is His,
                    Thr, Phe, Gly, Arg, Ala, or Trp"

(ix) FEATURE:
                (A) NAME/KEY: Modified-site
                (B) LOCATION: 13
                (D) OTHER INFORMATION: /note= "Xaa at position 13 is Leu,
                    Gly, Arg, Thr, Ser, or Ala"

(ix) FEATURE:
                (A) NAME/KEY: Modified-site
                (B) LOCATION: 14
                (D) OTHER INFORMATION: /note= "Xaa at position 14 is Lys,
                    Arg, Leu, Gln, Gly, Pro, Val, or Trp"

(ix) FEATURE:
                (A) NAME/KEY: Modified-site
                (B) LOCATION: 15
                (D) OTHER INFORMATION: /note= "Xaa at position 15 is Gln,
                    Asn, Leu, Pro, Arg, or Val"

(ix) FEATURE:
                (A) NAME/KEY: Modified-site
                (B) LOCATION: 16
                (D) OTHER INFORMATION: /note= "Xaa at position 16 is Pro,
                    His, Thr, Gly, Asp, Gln, Ser, Leu, or Lys"

(ix) FEATURE:
                (A) NAME/KEY: Modified-site
                (B) LOCATION: 17
                (D) OTHER INFORMATION: /note= "Xaa at position 17 is Pro,
                    Asp, Gly, Ala, Arg, Leu, or Gln"

(ix) FEATURE:
                (A) NAME/KEY: Modified-site
                (B) LOCATION: 18
                (D) OTHER INFORMATION: /note= "Xaa at position 18 is Leu,
                    Val, Arg, Gln, Asn, Gly, Ala, or Glu"

(ix) FEATURE:
                (A) NAME/KEY: Modified-site
                (B) LOCATION: 19
                (D) OTHER INFORMATION: /note= "Xaa at position 19 is Pro,
                    Leu, Gln, Ala, Thr, or Glu"

(ix) FEATURE:

(A) NAME/KEY: Modified-site
                (B) LOCATION: 20
                (D) OTHER INFORMATION: /note= "Xaa at position 20 is Leu,
                    Val, Gly, Ser, Lys, Glu, Gln, Thr, Arg, Ala, Phe,
                    Ile, or Met"

( i x ) FEATURE:
                (A) NAME/KEY: Modified-site
                (B) LOCATION: 21
                (D) OTHER INFORMATION: /note= "Xaa at position 21 is Leu,
                    Ala, Gly, Asn, Pro, Gln, or Val"

( i x ) FEATURE:
                (A) NAME/KEY: Modified-site
                (B) LOCATION: 22
                (D) OTHER INFORMATION: /note= "Xaa at position 22 is Asp,
                    Leu, or Val"

( i x ) FEATURE:
                (A) NAME/KEY: Modified-site
                (B) LOCATION: 23
                (D) OTHER INFORMATION: /note= "Xaa at position 23 is Phe,
                    Ser, Pro, Trp, or Ile"

( i x ) FEATURE:
                (A) NAME/KEY: Modified-site
                (B) LOCATION: 24
                (D) OTHER INFORMATION: /note= "Xaa at position 24 is Asn
                    or Ala"

( i x ) FEATURE:
                (A) NAME/KEY: Modified-site
                (B) LOCATION: 26
                (D) OTHER INFORMATION: /note= "Xaa at position 26 is Leu,
                    Trp, or Arg"

( i x ) FEATURE:
                (A) NAME/KEY: Modified-site
                (B) LOCATION: 27
                (D) OTHER INFORMATION: /note= "Xaa at position 27 is Asn,
                    Cys, Arg, Leu, His, Met, or Pro"

( i x ) FEATURE:
                (A) NAME/KEY: Modified-site
                (B) LOCATION: 28
                (D) OTHER INFORMATION: /note= "Xaa at position 28 is Gly,
                    Asp, Ser, Cys, Ala, Lys, Asn, Thr, Leu, Val, Glu,
                    Phe, Tyr, Ile, or Met"

( i x ) FEATURE:
                (A) NAME/KEY: Modified-site
                (B) LOCATION: 29
                (D) OTHER INFORMATION: /note= "Xaa at position 29 is Glu,
                    Asn, Tyr, Leu, Phe, Asp, Ala, Cys, Gln, Arg, Thr,
                    Gly, or Ser"

( i x ) FEATURE:
                (A) NAME/KEY: Modified-site
                (B) LOCATION: 30
                (D) OTHER INFORMATION: /note= "Xaa at position 30 is Asp,
                    Ser, Leu, Arg, Lys, Thr, Met, Trp, Glu, Asn, Gln,
                    Ala, or Pro"

( i x ) FEATURE:
                (A) NAME/KEY: Modified-site
                (B) LOCATION: 31
                (D) OTHER INFORMATION: /note= "Xaa at position 31 is Gln,
                    Pro, Phe, Val, Met, Leu, Thr, Lys, Asp, Asn, Arg,
                    Ser, Ala, Ile, Glu, His, or Trp"

( i x ) FEATURE:
                (A) NAME/KEY: Modified-site
                (B) LOCATION: 32
                (D) OTHER INFORMATION: /note= "Xaa at position 32 is Asp,
                    Phe, Ser, Thr, Cys, Glu, Asn, Gln, Lys, His, Ala,
                    Tyr, Ile, Val, or Gly"

( i x ) FEATURE:
                (A) NAME/KEY: Modified-site
                (B) LOCATION: 33

(D) OTHER INFORMATION: /note= "Xaa at position 33 is Ile,
Gly, Val, Ser, Arg, Pro, or His"

(ix) FEATURE:
(A) NAME/KEY: Modified-site
(B) LOCATION: 34
(D) OTHER INFORMATION: /note= "Xaa at position 34 is Leu,
Ser, Cys, Arg, Ile, His, Phe, Glu, Lys, Thr, Ala,
Met, Val, or Asn"

(ix) FEATURE:
(A) NAME/KEY: Modified-site
(B) LOCATION: 35
(D) OTHER INFORMATION: /note= "Xaa at position 35 is Met,
Arg, Ala, Gly, Pro, Asn, His, or Asp"

(ix) FEATURE:
(A) NAME/KEY: Modified-site
(B) LOCATION: 36
(D) OTHER INFORMATION: /note= "Xaa at position 36 is Glu,
Leu, Thr, Asp, Tyr, Lys, Asn, Ser, Ala, Ile, Val,
His, Phe, Met, or Gln"

(ix) FEATURE:
(A) NAME/KEY: Modified-site
(B) LOCATION: 37
(D) OTHER INFORMATION: /note= "Xaa at position 37 is Asn,
Arg, Met, Pro, Ser, Thr, or His"

(ix) FEATURE:
(A) NAME/KEY: Modified-site
(B) LOCATION: 38
(D) OTHER INFORMATION: /note= "Xaa at position 38 is Asn,
His, Arg, Leu, Gly, Ser, or Thr"

(ix) FEATURE:
(A) NAME/KEY: Modified-site
(B) LOCATION: 39
(D) OTHER INFORMATION: /note= "Xaa at position 39 is
Leu, Thr, Ala, Gly, Glu, Pro, Lys, Ser, or Met"

(ix) FEATURE:
(A) NAME/KEY: Modified-site
(B) LOCATION: 40
(D) OTHER INFORMATION: /note= "Xaa at position 40 is Arg,
Asp, Ile, Ser, Val, Thr, Gln, Asn, Lys, His,
Ala, or Leu"

(ix) FEATURE:
(A) NAME/KEY: Modified-site
(B) LOCATION: 41
(D) OTHER INFORMATION: /note= "Xaa at position 41 is Arg,
Thr, Val, Ser, Leu, or Gly"

(ix) FEATURE:
(A) NAME/KEY: Modified-site
(B) LOCATION: 42
(D) OTHER INFORMATION: /note= "Xaa at position 42 is Pro,
Gly, Cys, Ser, Gln, Glu, Arg, His, Thr, Ala, Tyr,
Phe, Leu, Val, or Lys"

(ix) FEATURE:
(A) NAME/KEY: Modified-site
(B) LOCATION: 43
(D) OTHER INFORMATION: /note= "Xaa at position 43 is Asn
or Gly"

(ix) FEATURE:
(A) NAME/KEY: Modified-site
(B) LOCATION: 44
(D) OTHER INFORMATION: /note= "Xaa at position 44 is Leu,
Ser, Asp, Arg, Gln, Val, or Cys"

(ix) FEATURE:
(A) NAME/KEY: Modified-site
(B) LOCATION: 45
(D) OTHER INFORMATION: /note= "Xaa at position 45 is Glu,
Tyr, His, Leu, Pro, or Arg"

(ix) FEATURE:

( A ) NAME/KEY: Modified-site
( B ) LOCATION: 46
( D ) OTHER INFORMATION: /note= "Xaa at position 46 is Ala, Ser, Pro, Tyr, Asn, or Thr"

( i x ) FEATURE:
( A ) NAME/KEY: Modified-site
( B ) LOCATION: 47
( D ) OTHER INFORMATION: /note= "Xaa at position 47 is Phe, Asn, Glu, Pro, Lys, Arg, or Ser"

( i x ) FEATURE:
( A ) NAME/KEY: Modified-site
( B ) LOCATION: 48
( D ) OTHER INFORMATION: /note= "Xaa at position 48 is Asn, His, Val, Arg, Pro, Thr, Asp, or Ile"

( i x ) FEATURE:
( A ) NAME/KEY: Modified-site
( B ) LOCATION: 49
( D ) OTHER INFORMATION: /note= "Xaa at position 49 is Arg, Tyr, Trp, Lys, Ser, His, Pro, or Val"

( i x ) FEATURE:
( A ) NAME/KEY: Modified-site
( B ) LOCATION: 50
( D ) OTHER INFORMATION: /note= "Xaa at position 50 is Ala, Asn, Pro, Ser, or Lys"

( i x ) FEATURE:
( A ) NAME/KEY: Modified-site
( B ) LOCATION: 51
( D ) OTHER INFORMATION: /note= "Xaa at position 51 is Val, Thr, Pro, His, Leu, Phe, or Ser"

( i x ) FEATURE:
( A ) NAME/KEY: Modified-site
( B ) LOCATION: 52
( D ) OTHER INFORMATION: /note= "Xaa at position 52 is Lys, Ile, Arg, Val, Asn, Glu, or Ser"

( i x ) FEATURE:
( A ) NAME/KEY: Modified-site
( B ) LOCATION: 53
( D ) OTHER INFORMATION: /note= "Xaa at position 53 is Ser, Ala, Phe, Val, Gly, Asn, Ile, Pro, or His"

( i x ) FEATURE:
( A ) NAME/KEY: Modified-site
( B ) LOCATION: 54
( D ) OTHER INFORMATION: /note= "Xaa at position 54 is Leu, Val, Trp, Ser, Ile, Phe, Thr, or His"

( i x ) FEATURE:
( A ) NAME/KEY: Modified-site
( B ) LOCATION: 55
( D ) OTHER INFORMATION: /note= "Xaa at position 55 is Gln, Ala, Pro, Thr, Glu, Arg, Trp, Gly, or Leu"

( i x ) FEATURE:
( A ) NAME/KEY: Modified-site
( B ) LOCATION: 56
( D ) OTHER INFORMATION: /note= "Xaa at position 56 is Asn, Leu, Val, Trp, Pro, or Ala"

( i x ) FEATURE:
( A ) NAME/KEY: Modified-site
( B ) LOCATION: 57
( D ) OTHER INFORMATION: /note= "Xaa at position 57 is Ala, Met, Leu, Pro, Arg, Glu, Thr, Gln, Trp, or Asn"

( i x ) FEATURE:
( A ) NAME/KEY: Modified-site
( B ) LOCATION: 58
( D ) OTHER INFORMATION: /note= "Xaa at position 58 is Ser, Glu, Met, Ala, His, Asn, Arg, or Asp"

( i x ) FEATURE:
( A ) NAME/KEY: Modified-site
( B ) LOCATION: 59

( D ) OTHER INFORMATION: /note= "Xaa at position 59 is Ala,
Glu, Asp, Leu, Ser, Gly, Thr, or Arg"

( i x ) FEATURE:
    ( A ) NAME/KEY: Modified-site
    ( B ) LOCATION: 60
    ( D ) OTHER INFORMATION: /note= "Xaa at position 60 is Ile,
Met, Thr, Pro, Arg, Gly, Ala"

( i x ) FEATURE:
    ( A ) NAME/KEY: Modified-site
    ( B ) LOCATION: 61
    ( D ) OTHER INFORMATION: /note= "Xaa at position 61 is
Glu, Lys, Gly, Asp, Pro, Trp, Arg, Ser, Gln,
or Leu"

( i x ) FEATURE:
    ( A ) NAME/KEY: Modified-site
    ( B ) LOCATION: 62
    ( D ) OTHER INFORMATION: /note= "Xaa at position 62 is Ser,
Val, Ala, Asn, Trp, Glu, Pro, Gly, or Asp"

( i x ) FEATURE:
    ( A ) NAME/KEY: Modified-site
    ( B ) LOCATION: 63
    ( D ) OTHER INFORMATION: /note= "Xaa at position 63 is Ile,
Ser, Arg, Thr, or Leu"

( i x ) FEATURE:
    ( A ) NAME/KEY: Modified-site
    ( B ) LOCATION: 64
    ( D ) OTHER INFORMATION: /note= "Xaa at position 64 is Leu,
Ala, Ser, Glu, Phe, Gly, or Arg"

( i x ) FEATURE:
    ( A ) NAME/KEY: Modified-site
    ( B ) LOCATION: 65
    ( D ) OTHER INFORMATION: /note= "Xaa at position 65 is Lys,
Thr, Gly, Asn, Met, Arg, Ile, or Asp"

( i x ) FEATURE:
    ( A ) NAME/KEY: Modified-site
    ( B ) LOCATION: 66
    ( D ) OTHER INFORMATION: /note= "Xaa at position 66 is Asn,
Trp, Val, Gly, Thr, Leu, Glu, or Arg"

( i x ) FEATURE:
    ( A ) NAME/KEY: Modified-site
    ( B ) LOCATION: 67
    ( D ) OTHER INFORMATION: /note= "Xaa at position 67 is Leu,
Gln, Gly, Ala, Trp, Arg, Val, or Lys"

( i x ) FEATURE:
    ( A ) NAME/KEY: Modified-site
    ( B ) LOCATION: 68
    ( D ) OTHER INFORMATION: /note= "Xaa at position 68 is Leu,
Gln, Lys, Trp, Arg, Asp, Glu, Asn, His, Thr, Ser, Ala,
Tyr, Phe, Ile, Met, or Val"

( i x ) FEATURE:
    ( A ) NAME/KEY: Modified-site
    ( B ) LOCATION: 69
    ( D ) OTHER INFORMATION: /note= "Xaa at position 69 is Pro,
Ala, Thr, Trp, Arg, or Met"

( i x ) FEATURE:
    ( A ) NAME/KEY: Modified-site
    ( B ) LOCATION: 70
    ( D ) OTHER INFORMATION: /note= "Xaa at position 70 is Cys,
Glu, Gly, Arg, Met, or Val"

( i x ) FEATURE:
    ( A ) NAME/KEY: Modified-site
    ( B ) LOCATION: 71
    ( D ) OTHER INFORMATION: /note= "Xaa at position 71 is Leu,
Asn, Val, or Gln"

( i x ) FEATURE:
    ( A ) NAME/KEY: Modified-site
    ( B ) LOCATION: 72

```
            ( D ) OTHER INFORMATION: /note= "Xaa at position 72 is Pro,
                    Cys, Arg, Ala, or Lys"

( i x ) FEATURE:
            ( A ) NAME/KEY: Modified-site
            ( B ) LOCATION: 73
            ( D ) OTHER INFORMATION: /note= "Xaa at position 73 is Leu,
                    Ser, Trp, or Gly"

( i x ) FEATURE:
            ( A ) NAME/KEY: Modified-site
            ( B ) LOCATION: 74
            ( D ) OTHER INFORMATION: /note= "Xaa at position 74 is Ala,
                    Lys, Arg, Val, or Trp"

( i x ) FEATURE:
            ( A ) NAME/KEY: Modified-site
            ( B ) LOCATION: 75
            ( D ) OTHER INFORMATION: /note= "Xaa at position 75 is Thr,
                    Asp, Cys, Leu, Val, Glu, His, Asn, or Ser"

( i x ) FEATURE:
            ( A ) NAME/KEY: Modified-site
            ( B ) LOCATION: 76
            ( D ) OTHER INFORMATION: /note= "Xaa at position 76 is Ala,
                    Pro, Ser, Thr, Gly, Asp, Ile, or Met"

( i x ) FEATURE:
            ( A ) NAME/KEY: Modified-site
            ( B ) LOCATION: 77
            ( D ) OTHER INFORMATION: /note= "Xaa at position 77 is Ala,
                    Pro, Ser, Thr, Phe, Leu, Asp, or His"

( i x ) FEATURE:
            ( A ) NAME/KEY: Modified-site
            ( B ) LOCATION: 78
            ( D ) OTHER INFORMATION: /note= "Xaa at position 78 is Pro,
                    Phe, Arg, Ser, Lys, His, Ala, Gly, Ile, or Leu"

( i x ) FEATURE:
            ( A ) NAME/KEY: Modified-site
            ( B ) LOCATION: 79
            ( D ) OTHER INFORMATION: /note= "Xaa at position 79 is Thr,
                    Asp, Ser, Asn, Pro, Ala, Leu, or Arg"

( i x ) FEATURE:
            ( A ) NAME/KEY: Modified-site
            ( B ) LOCATION: 80
            ( D ) OTHER INFORMATION: /note= "Xaa at position 80 is Arg,
                    Ile, Ser, Glu, Leu, Val, Gln, Lys, His, Ala, or Pro"

( i x ) FEATURE:
            ( A ) NAME/KEY: Modified-site
            ( B ) LOCATION: 81
            ( D ) OTHER INFORMATION: /note= "Xaa at position 81 is His,
                    Gln, Pro, Arg, Val, Leu, Gly, Thr, Asn, Lys, Ser,
                    Ala, Trp, Phe, Ile, or Tyr"

( i x ) FEATURE:
            ( A ) NAME/KEY: Modified-site
            ( B ) LOCATION: 82
            ( D ) OTHER INFORMATION: /note= "Xaa at position 82 is Pro,
                    Lys, Tyr, Gly, Ile, or Thr"

( i x ) FEATURE:
            ( A ) NAME/KEY: Modified-site
            ( B ) LOCATION: 83
            ( D ) OTHER INFORMATION: /note= "Xaa at position 83 is Ile,
                    Val, Lys, Ala, or Asn"

( i x ) FEATURE:
            ( A ) NAME/KEY: Modified-site
            ( B ) LOCATION: 84
            ( D ) OTHER INFORMATION: /note= "Xaa at position 84 is His,
                    Ile, Asn, Leu, Asp, Ala, Thr, Leu, Glu, Gln, Ser,
                    Phe, Met, Val, Lys, Arg, Tyr, or Pro"

( i x ) FEATURE:
            ( A ) NAME/KEY: Modified-site
            ( B ) LOCATION: 85
```

(D) OTHER INFORMATION: /note= "Xaa at position 85 is
Ile, Leu, Arg, Asp, Val, Pro, Gln, Gly, Ser,
Phe, or His"

(ix) FEATURE:
(A) NAME/KEY: Modified-site
(B) LOCATION: 86
(D) OTHER INFORMATION: /note= "Xaa at position 86 is
Lys, Tyr, Leu, His, Arg, Ile, Ser, Gln, or Pro"

(ix) FEATURE:
(A) NAME/KEY: Modified-site
(B) LOCATION: 87
(D) OTHER INFORMATION: /note= "Xaa at position 87 is
Asp, Pro, Met, Lys, His, Thr, Val, Tyr, Glu, Asn,
Ser, Ala, Gly, Ile, Leu, or Gln"

(ix) FEATURE:
(A) NAME/KEY: Modified-site
(B) LOCATION: 88
(D) OTHER INFORMATION: /note= "Xaa at position 88 Gly,
Leu, Glu, Lys, Ser, Tyr, or Pro"

(ix) FEATURE:
(A) NAME/KEY: Modified-site
(B) LOCATION: 89
(D) OTHER INFORMATION: /note= "Xaa at position 89 is Asp
or Ser"

(ix) FEATURE:
(A) NAME/KEY: Modified-site
(B) LOCATION: 90
(D) OTHER INFORMATION: /note= "Xaa at position 90 is
Trp, Val, Cys, Tyr, Thr, Met, Pro, Leu, Gln, Lys,
Ala, Phe, or Gly"

(ix) FEATURE:
(A) NAME/KEY: Modified-site
(B) LOCATION: 91
(D) OTHER INFORMATION: /note= "Xaa at position 91 is
Asn, Pro, Ala, Phe, Ser, Trp, Gln, Tyr, Leu, Lys,
Ile, Asp, or His"

(ix) FEATURE:
(A) NAME/KEY: Modified-site
(B) LOCATION: 92
(D) OTHER INFORMATION: /note= "Xaa at position 92 is Glu,
Ser, Ala, Lys, Thr, Ile, Gly, or Pro"

(ix) FEATURE:
(A) NAME/KEY: Modified-site
(B) LOCATION: 94
(D) OTHER INFORMATION: /note= "Xaa at position 94 is Arg,
Lys, Asp, Leu, Thr, Ile, Gln, His, Ser, Ala, or Pro"

(ix) FEATURE:
(A) NAME/KEY: Modified-site
(B) LOCATION: 95
(D) OTHER INFORMATION: /note= "Xaa at position 95 is Arg,
Thr, Pro, Glu, Tyr, Leu, Ser, or Gly"

(ix) FEATURE:
(A) NAME/KEY: Modified-site
(B) LOCATION: 96
(D) OTHER INFORMATION: /note= "Xaa at position 96 is Lys,
Asn, Thr, Leu, Gln, Arg, His, Glu, Ser, Ala,
or Trp"

(ix) FEATURE:
(A) NAME/KEY: Modified-site
(B) LOCATION: 97
(D) OTHER INFORMATION: /note= "Xaa at position 97 is Leu,
Ile, Arg, Asp, or Met"

(ix) FEATURE:
(A) NAME/KEY: Modified-site
(B) LOCATION: 98
(D) OTHER INFORMATION: /note= "Xaa at position 98 is Thr,
Val, Gln, Tyr, Glu, His, Ser, or Phe"

( i x ) FEATURE:
  ( A ) NAME/KEY: Modified-site
  ( B ) LOCATION: 99
  ( D ) OTHER INFORMATION: /note= "Xaa at position 99 is Phe, Ser, Cys, His, Gly, Trp, Tyr, Asp, Lys, Leu, Ile, Val, or Asn"

( i x ) FEATURE:
  ( A ) NAME/KEY: Modified-site
  ( B ) LOCATION: 100
  ( D ) OTHER INFORMATION: /note= "Xaa at position 100 is Tyr, Cys, His, Ser, Trp, Arg, or Leu"

( i x ) FEATURE:
  ( A ) NAME/KEY: Modified-site
  ( B ) LOCATION: 101
  ( D ) OTHER INFORMATION: /note= "Xaa at position 101 is Leu, Asn, Val, Pro, Arg, Ala, His, Thr, Trp, or Met"

( i x ) FEATURE:
  ( A ) NAME/KEY: Modified-site
  ( B ) LOCATION: 102
  ( D ) OTHER INFORMATION: /note= "Xaa at position 102 is Lys, Leu, Pro, Thr, Met, Asp, Val, Glu, Arg, Trp, Ser, Asn, His, Ala, Tyr, Phe, Gln, or Ile"

( i x ) FEATURE:
  ( A ) NAME/KEY: Modified-site
  ( B ) LOCATION: 103
  ( D ) OTHER INFORMATION: /note= "Xaa at position 103 is Thr, Ser, Asn, Ile, Trp, Lys, or Pro"

( i x ) FEATURE:
  ( A ) NAME/KEY: Modified-site
  ( B ) LOCATION: 104
  ( D ) OTHER INFORMATION: /note= "Xaa at position 104 is Leu, Ser, Pro, Ala, Glu, Cys, Asp, or Tyr"

( i x ) FEATURE:
  ( A ) NAME/KEY: Modified-site
  ( B ) LOCATION: 105
  ( D ) OTHER INFORMATION: /note= "Xaa at position 105 is Glu, Ser, Lys, Pro, Leu, Thr, Tyr, or Arg"

( i x ) FEATURE:
  ( A ) NAME/KEY: Modified-site
  ( B ) LOCATION: 106
  ( D ) OTHER INFORMATION: /note= "Xaa at position 106 is Asn, Ala, Pro, Leu, His, Val or Gln"

( i x ) FEATURE:
  ( A ) NAME/KEY: Modified-site
  ( B ) LOCATION: 107
  ( D ) OTHER INFORMATION: /note= "Xaa at position 107 is Ala, Ser, Ile, Asn, Pro, Lys, Asp, or Gly"

( i x ) FEATURE:
  ( A ) NAME/KEY: Modified-site
  ( B ) LOCATION: 108
  ( D ) OTHER INFORMATION: /note= "Xaa at position 108 is Gln, Ser, Met, Trp, Arg, Phe, Pro, His, Ile, Tyr, or Cys"

( i x ) FEATURE:
  ( A ) NAME/KEY: Modified-site
  ( B ) LOCATION: 109
  ( D ) OTHER INFORMATION: /note= "Xaa at position 109 is Ala, Met, Glu, His, Ser, Pro, Tyr, or Leu"

( x i ) SEQUENCE DESCRIPTION: SEQ ID NO:4:

Asn Cys Xaa Xaa Xaa Xaa Xaa Xaa Xaa Xaa Xaa Xaa Xaa Xaa Xaa Xaa
1               5                              10                          15

Xaa Xaa Xaa Xaa Xaa Xaa Xaa Xaa Asn Xaa Xaa Xaa Xaa Xaa Xaa Xaa
            20                          25                          30

Xaa Xaa Xaa Xaa Xaa Xaa Xaa Xaa Xaa Xaa Xaa Xaa Xaa Xaa Xaa Xaa
            35                          40                          45

```
Xaa  Xaa  Xaa  Xaa  Xaa  Xaa  Xaa  Xaa  Xaa  Xaa  Xaa  Xaa  Xaa  Xaa  Xaa  Xaa
 50                          55                      60

Xaa  Xaa  Xaa  Xaa  Xaa  Xaa  Xaa  Xaa  Xaa  Xaa  Xaa  Xaa  Xaa  Xaa  Xaa  Xaa
 65                      70                  75                              80

Xaa  Xaa  Xaa  Xaa  Xaa  Xaa  Xaa  Xaa  Xaa  Xaa  Xaa  Xaa  Phe  Xaa  Xaa  Xaa
                 85                      90                              95

Xaa  Xaa  Xaa  Xaa  Xaa  Xaa  Xaa  Xaa  Xaa  Xaa  Xaa  Xaa  Xaa  Gln  Gln
                100                     105                     110
```

( 2 ) INFORMATION FOR SEQ ID NO:5:

( i ) SEQUENCE CHARACTERISTICS:
    ( A ) LENGTH: 111 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Met- or Met-Ala- may or may
      not precede the amino acid in position 1"

( i x ) FEATURE:
    ( A ) NAME/KEY: Modified-site
    ( B ) LOCATION: 3
    ( D ) OTHER INFORMATION: /note= "Xaa at position 3 is Ser,
      Gly, Asp, Met, or Gln"

( i x ) FEATURE:
    ( A ) NAME/KEY: Modified-site
    ( B ) LOCATION: 4
    ( D ) OTHER INFORMATION: /note= "Xaa at position 4 is Asn,
      His, or Ile"

( i x ) FEATURE:
    ( A ) NAME/KEY: Modified-site
    ( B ) LOCATION: 5
    ( D ) OTHER INFORMATION: /note= "Xaa at position 5 is Met
      or Ile"

( i x ) FEATURE:
    ( A ) NAME/KEY: Modified-site
    ( B ) LOCATION: 7
    ( C ) OTHER INFORMATION: /note= "Xaa at position 7 is Asp or
      Glu"

( i x ) FEATURE:
    ( A ) NAME/KEY: Modified-site
    ( B ) LOCATION: 9
    ( D ) OTHER INFORMATION: /note= "Xaa at position 9 is Ile,
      Ala, Leu, or Gly"

( i x ) FEATURE:
    ( A ) NAME/KEY: Modified-site
    ( B ) LOCATION: 10
    ( D ) OTHER INFORMATION: /note= "Xaa at position 10 is Ile,
      Val, or Leu"

( i x ) FEATURE:
    ( A ) NAME/KEY: Modified-site
    ( B ) LOCATION: 11
    ( D ) OTHER INFORMATION: /note= "Xaa at position 11 is Thr,
      His, Gln, or Ala"

( i x ) FEATURE:
    ( A ) NAME/KEY: Modified-site
    ( B ) LOCATION: 12
    ( D ) OTHER INFORMATION: /note= "Xaa at position 12 is His
      or Ala"

( i x ) FEATURE:
    ( A ) NAME/KEY: Modified-site
    ( B ) LOCATION: 15
    ( D ) OTHER INFORMATION: /note= "Xaa at position 15 is Gln, -continued Asn, or Val"

( i x ) FEATURE:
 ( A ) NAME/KEY: Modified-site
 ( B ) LOCATION: 16
 ( D ) OTHER INFORMATION: /note= "Xaa at position 16 is Pro,
  Gly, or Gln"

( i x ) FEATURE:
 ( A ) NAME/KEY: Modified-site
 ( B ) LOCATION: 17
 ( D ) OTHER INFORMATION: /note= "Xaa at position 17 is Pro,
  Asp, Gly, or Gln"

( i x ) FEATURE:
 ( A ) NAME/KEY: Modified-site
 ( B ) LOCATION: 18
 ( D ) OTHER INFORMATION: /note= "Xaa at position 18 is Leu,
  Arg, Gln, Asn, Gly, Ala, or Glu"

( i x ) FEATURE:
 ( A ) NAME/KEY: Modified-site
 ( B ) LOCATION: 19
 ( D ) OTHER INFORMATION: /note= "Xaa at position 19 is Pro
  or Glu"

( i x ) FEATURE:
 ( A ) NAME/KEY: Modified-site
 ( B ) LOCATION: 20
 ( D ) OTHER INFORMATION: /note= "Xaa at position 20 is Leu,
  Val, Gly, Ser, Lys, Ala, Arg, Gln, Glu, Ile, Phe,
  Thr, or Met"

( i x ) FEATURE:
 ( A ) NAME/KEY: Modified-site
 ( B ) LOCATION: 21
 ( D ) OTHER INFORMATION: /note= "Xaa at position 21 is Leu,
  Ala, Asn, Pro, Gln, or Val"

( i x ) FEATURE:
 ( A ) NAME/KEY: Modified-site
 ( B ) LOCATION: 23
 ( D ) OTHER INFORMATION: /note= "Xaa at position 23 is Phe,
  Ser, Pro, or Trp"

( i x ) FEATURE:
 ( A ) NAME/KEY: Modified-site
 ( B ) LOCATION: 24
 ( D ) OTHER INFORMATION: /note= "Xaa at position 24 is Asn
  or Ala"

( i x ) FEATURE:
 ( A ) NAME/KEY: Modified-site
 ( B ) LOCATION: 28
 ( D ) OTHER INFORMATION: /note= "Xaa at position 28 is Gly,
  Asp, Ser, Cys, Ala, Asn, Ile, Leu, Met, Tyr, or Arg"

( i x ) FEATURE:
 ( A ) NAME/KEY: Modified-site
 ( B ) LOCATION: 30
 ( D ) OTHER INFORMATION: /note= "Xaa at position 30 is Asp
  or Glu"

( i x ) FEATURE:
 ( A ) NAME/KEY: Modified-site
 ( B ) LOCATION: 31
 ( D ) OTHER INFORMATION: /note= "Xaa at position 31 is Gln,
  Val, Met, Leu, Thr, Ala, Asn, Glu, Ser, or Lys"

( i x ) FEATURE:
 ( A ) NAME/KEY: Modified-site
 ( B ) LOCATION: 32
 ( D ) OTHER INFORMATION: /note= "Xaa at position 32 is Asp,
  Phe, Ser, Thr, Ala, Asn, Gln, Glu, His, Ile, Lys,
  Tyr, Val, or Cys"

( i x ) FEATURE:
 ( A ) NAME/KEY: Modified-site
 ( B ) LOCATION: 36
 ( D ) OTHER INFORMATION: /note= "Xaa at position 36 is Glu, Ala, Asn, Ser, or Asp"

( i x ) FEATURE:
    ( A ) NAME/KEY: Modified-site
    ( B ) LOCATION: 37
    ( D ) OTHER INFORMATION: /note= "Xaa at position 37 is Asn, Arg, Met, Pro, Ser, Thr, or His"

( i x ) FEATURE:
    ( A ) NAME/KEY: Modified-site
    ( B ) LOCATION: 40
    ( D ) OTHER INFORMATION: /note= "Xaa at position 40 is Arg or Ala"

( i x ) FEATURE:
    ( A ) NAME/KEY: Modified-site
    ( B ) LOCATION: 41
    ( D ) OTHER INFORMATION: /note= "Xaa at position 41 is Arg, Thr, Val, Leu, or Gly"

( i x ) FEATURE:
    ( A ) NAME/KEY: Modified-site
    ( B ) LOCATION: 42
    ( D ) OTHER INFORMATION: /note= "Xaa at position 42 is Pro, Gly, Ser, Gln, Ala, Arg, Asn, Glu, Leu, Thr, Val, or Lys"

( i x ) FEATURE:
    ( A ) NAME/KEY: Modified-site
    ( B ) LOCATION: 46
    ( D ) OTHER INFORMATION: /note= "Xaa at position 46 is Ala or Ser"

( i x ) FEATURE:
    ( A ) NAME/KEY: Modified-site
    ( B ) LOCATION: 48
    ( D ) OTHER INFORMATION: /note= "Xaa at position 48 is Asn, Pro, Thr, or Ile"

( i x ) FEATURE:
    ( A ) NAME/KEY: Modified-site
    ( B ) LOCATION: 49
    ( D ) OTHER INFORMATION: /note= "Xaa at position 49 is Arg or Lys"

( i x ) FEATURE:
    ( A ) NAME/KEY: Modified-site
    ( B ) LOCATION: 50
    ( D ) OTHER INFORMATION: /note= "Xaa at position 50 is Ala or Asn"

( i x ) FEATURE:
    ( A ) NAME/KEY: Modified-site
    ( B ) LOCATION: 51
    ( D ) OTHER INFORMATION: /note= "Xaa at position 51 is Val or Thr"

( i x ) FEATURE:
    ( A ) NAME/KEY: Modified-site
    ( B ) LOCATION: 52
    ( D ) OTHER INFORMATION: /note= "Xaa at position 52 is Lys or Arg"

( i x ) FEATURE:
    ( A ) NAME/KEY: Modified-site
    ( B ) LOCATION: 53
    ( D ) OTHER INFORMATION: /note= "Xaa at position 53 is Ser, Phe, or His"

( i x ) FEATURE:
    ( A ) NAME/KEY: Modified-site
    ( B ) LOCATION: 54
    ( D ) OTHER INFORMATION: /note= "Xaa at position 54 is Leu, Ile, Phe, or His"

( i x ) FEATURE:
    ( A ) NAME/KEY: Modified-site
    ( B ) LOCATION: 55
    ( D ) OTHER INFORMATION: /note= "Xaa at position 55 is Gln, Ala, Pro, Thr, Glu, Arg, or Gly"

( i x ) FEATURE:
  ( A ) NAME/KEY: Modified-site
  ( B ) LOCATION: 57
  ( D ) OTHER INFORMATION: /note= "Xaa at position 57 is Ala,
    Pro, or Arg"

( i x ) FEATURE:
  ( A ) NAME/KEY: Modified-site
  ( B ) LOCATION: 58
  ( D ) OTHER INFORMATION: /note= "Xaa at position 58 is Ser,
    Glu, Arg, or Asp"

( i x ) FEATURE:
  ( A ) NAME/KEY: Modified-site
  ( B ) LOCATION: 59
  ( D ) OTHER INFORMATION: /note= "Xaa at position 59 is Ala
    or Leu"

( i x ) FEATURE:
  ( A ) NAME/KEY: Modified-site
  ( B ) LOCATION: 62
  ( D ) OTHER INFORMATION: /note= "Xaa at position 62 is Ser,
    Val, Ala, Asn, Glu, Pro, or Gly"

( i x ) FEATURE:
  ( A ) NAME/KEY: Modified-site
  ( B ) LOCATION: 63
  ( D ) OTHER INFORMATION: /note= "Xaa at position 63 is Ile
    or Leu"

( i x ) FEATURE:
  ( A ) NAME/KEY: Modified-site
  ( B ) LOCATION: 65
  ( D ) OTHER INFORMATION: /note= "Xaa at position 65 is Lys,
    Thr, Gly, Asn, Met, Arg, Ile, or Asp"

( i x ) FEATURE:
  ( A ) NAME/KEY: Modified-site
  ( B ) LOCATION: 66
  ( D ) OTHER INFORMATION: /note= "Xaa at position 66 is Asn,
    Gly, Glu, or Arg"

( i x ) FEATURE:
  ( A ) NAME/KEY: Modified-site
  ( B ) LOCATION: 68
  ( D ) OTHER INFORMATION: /note= "Xaa at position 68 is Leu,
    Gln, Trp, Arg, Asp, Ala, Asn, Glu, His, Ile, Met,
    Phe, Ser, Thr, Tyr, or Val"

( i x ) FEATURE:
  ( A ) NAME/KEY: Modified-site
  ( B ) LOCATION: 69
  ( D ) OTHER INFORMATION: /note= "Xaa at position 69 is Pro
    or Thr"

( i x ) FEATURE:
  ( A ) NAME/KEY: Modified-site
  ( B ) LOCATION: 71
  ( D ) OTHER INFORMATION: /note= "Xaa at position 71 is Leu
    or Val"

( i x ) FEATURE:
  ( A ) NAME/KEY: Modified-site
  ( B ) LOCATION: 73
  ( D ) OTHER INFORMATION: /note= "Xaa at position 73 is Leu
    or Ser"

( i x ) FEATURE:
  ( A ) NAME/KEY: Modified-site
  ( B ) LOCATION: 74
  ( D ) OTHER INFORMATION: /note= "Xaa at position 74 is Ala
    or Trp"

( i x ) FEATURE:
  ( A ) NAME/KEY: Modified-site
  ( B ) LOCATION: 77
  ( D ) OTHER INFORMATION: /note= "Xaa at position 77 is Ala
    or Pro"

( i x ) FEATURE:
        ( A ) NAME/KEY: Modified-site
        ( B ) LOCATION: 79
        ( D ) OTHER INFORMATION: /note= "Xaa at position 79 is Thr,
              Asp, Ser, Pro, Ala, Leu, or Arg"

( i x ) FEATURE:
        ( A ) NAME/KEY: Modified-site
        ( B ) LOCATION: 81
        ( D ) OTHER INFORMATION: /note= "Xaa at position 81 is His,
              Pro, Arg, Val, Leu, Gly, Asn, Phe, Ser, or Thr"

( i x ) FEATURE:
        ( A ) NAME/KEY: Modified-site
        ( B ) LOCATION: 82
        ( D ) OTHER INFORMATION: /note= "Xaa at position 82 is Pro
              or Tyr"

( i x ) FEATURE:
        ( A ) NAME/KEY: Modified-site
        ( B ) LOCATION: 83
        ( D ) OTHER INFORMATION: /note= "Xaa at position 83 is Ile
              or Val"

( i x ) FEATURE:
        ( A ) NAME/KEY: Modified-site
        ( B ) LOCATION: 84
        ( D ) OTHER INFORMATION: /note= "Xaa at position 84 is His,
              Ile, Asn, Leu, Ala, Thr, Arg, Gln, Lys,
              Met, Ser, Tyr, Val, or Pro"

( i x ) FEATURE:
        ( A ) NAME/KEY: Modified-site
        ( B ) LOCATION: 85
        ( D ) OTHER INFORMATION: /note= "Xaa at position 85 is Ile,
              Leu, or Val"

( i x ) FEATURE:
        ( A ) NAME/KEY: Modified-site
        ( B ) LOCATION: 86
        ( D ) OTHER INFORMATION: /note= "Xaa at position 86 is Lys,
              Arg, Ile, Ser, Gln, Pro, or Ser"

( i x ) FEATURE:
        ( A ) NAME/KEY: Modified-site
        ( B ) LOCATION: 87
        ( D ) OTHER INFORMATION: /note= "Xaa at position 87 is Asp,
              Pro, Met, Lys, His, Thr, Asn, Ile, Leu, or Tyr"

( i x ) FEATURE:
        ( A ) NAME/KEY: Modified-site
        ( B ) LOCATION: 90
        ( D ) OTHER INFORMATION: /note= "Xaa at position 90 is Trp
              or Leu"

( i x ) FEATURE:
        ( A ) NAME/KEY: Modified-site
        ( B ) LOCATION: 91
        ( D ) OTHER INFORMATION: /note="Xaa at position 91 is Asn,
              Pro, Ala, Ser, Trp, Gln, Tyr, Leu, Lys, Ile, Asp,
              or His"

( i x ) FEATURE:
        ( A ) NAME/KEY: Modified-site
        ( B ) LOCATION: 92
        ( D ) OTHER INFORMATION: /note= "Xaa at position 92 is Glu
              or Gly"

( i x ) FEATURE:
        ( A ) NAME/KEY: Modified-site
        ( B ) LOCATION: 94
        ( C ) OTHER INFORMATION: /note= "Xaa at position 94 is Arg,
              Ala, or Ser"

( i x ) FEATURE:
        ( A ) NAME/KEY: Modified-site
        ( B ) LOCATION: 95
        ( D ) OTHER INFORMATION: /note= "Xaa at position 95 is Arg,
              Thr, Glu, Leu, or Ser"

-continued

```
    ( i x ) FEATURE:
            ( A ) NAME/KEY: Modified-site
            ( B ) LOCATION: 98
            ( D ) OTHER INFORMATION: /note= "Xaa at position 98 is Thr,
                    Val, or Gln"

( i x ) FEATURE:
            ( A ) NAME/KEY: Modified-site
            ( B ) LOCATION: 100
            ( D ) OTHER INFORMATION: /note= "Xaa at position 100 is Tyr
                    or Trp"

( i x ) FEATURE:
            ( A ) NAME/KEY: Modified-site
            ( B ) LOCATION: 101
            ( D ) OTHER INFORMATION: /note= "Xaa at position 101 is Leu
                    or Ala"

( i x ) FEATURE:
            ( A ) NAME/KEY: Modified-site
            ( B ) LOCATION: 102
            ( D ) OTHER INFORMATION: /note= "Xaa at position 102 is Lys,
                    Thr, Val, Trp, Ser, Ala, His, Met, Phe, Tyr, or Ile"

( i x ) FEATURE:
            ( A ) NAME/KEY: Modified-site
            ( B ) LOCATION: 103
            ( D ) OTHER INFORMATION: /note= "Xaa at position 103 is Thr
                    or Ser"

( i x ) FEATURE:
            ( A ) NAME/KEY: Modified-site
            ( B ) LOCATION: 106
            ( D ) OTHER INFORMATION: /note= "Xaa at position 106 is Asn,
                    Pro, Leu, His, Val, or Gln"

( i x ) FEATURE:
            ( A ) NAME/KEY: Modified-site
            ( B ) LOCATION: 107
            ( D ) OTHER INFORMATION: /note= "Xaa at position 107 is Ala,
                    Ser, Ile, Asn, Pro, Asp, or Gly"

( i x ) FEATURE:
            ( A ) NAME/KEY: Modified-site
            ( B ) LOCATION: 108
            ( D ) OTHER INFORMATION: /note= "Xaa at position 108 is Gln,
                    Ser, Met, Trp, Arg, Phe, Pro, His, Ile, Tyr, or Cys"

( i x ) FEATURE:
            ( A ) NAME/KEY: Modified-site
            ( B ) LOCATION: 109
            ( D ) OTHER INFORMATION: /note= "Xaa at position 109 is Ala,
                    Met, Glu, His, Ser, Pro, Tyr, or Leu"

( x i ) SEQUENCE DESCRIPTION: SEQ ID NO:5:

Asn  Cys  Xaa  Xaa  Xaa  Ile  Xaa  Glu  Xaa  Xaa  Xaa  Xaa  Leu  Lys  Xaa  Xaa
    1                   5                        10                            15

Xaa  Xaa  Xaa  Xaa  Xaa  Asp  Xaa  Xaa  Asn  Leu  Asn  Xaa  Glu  Xaa  Xaa  Xaa
                   20                   25                        30

Ile  Leu  Met  Xaa  Xaa  Asn  Leu  Xaa  Xaa  Xaa  Asn  Leu  Glu  Xaa  Phe  Xaa
              35                        40                   45

Xaa  Xaa  Xaa  Xaa  Xaa  Xaa  Xaa  Asn  Xaa  Xaa  Xaa  Ile  Glu  Xaa  Xaa  Leu
              50                        55                        60

Xaa  Xaa  Leu  Xaa  Xaa  Cys  Xaa  Pro  Xaa  Xaa  Thr  Ala  Xaa  Pro  Xaa  Arg
    65                        70                        75                        80

Xaa  Xaa  Xaa  Xaa  Xaa  Xaa  Xaa  Gly  Asp  Xaa  Xaa  Xaa  Phe  Xaa  Xaa  Lys
                        85                        90                        95

Leu  Xaa  Phe  Xaa  Xaa  Xaa  Xaa  Leu  Glu  Xaa  Xaa  Xaa  Xaa  Gln  Gln
                        100                       105                       110

( 2 ) INFORMATION FOR SEQ ID NO:6:
```

( i ) SEQUENCE CHARACTERISTICS:
    ( A ) LENGTH: 111 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Met- or Met-Ala- may or may not precede the amino acid in position 1"

( i x ) FEATURE:
    ( A ) NAME/KEY: Modified-site
    ( B ) LOCATION: 3
    ( D ) OTHER INFORMATION: /note= "Xaa at position 3 is Ser, Gly, Asp, or Gln"

( i x ) FEATURE:
    ( A ) NAME/KEY: Modified-site
    ( B ) LOCATION: 4
    ( D ) OTHER INFORMATION: /note= "Xaa at position 4 is Asn, His, or Ile"

( i x ) FEATURE:
    ( A ) NAME/KEY: Modified-site
    ( B ) LOCATION: 9
    ( D ) OTHER INFORMATION: /note= "Xaa at position 9 is Ile, Ala, Leu, or Gly"

( i x ) FEATURE:
    ( A ) NAME/KEY: Modified-site
    ( B ) LOCATION: 11
    ( D ) OTHER INFORMATION: /note= "Xaa at position 11 is Thr, His, or Gln"

( i x ) FEATURE:
    ( A ) NAME/KEY: Modified-site
    ( B ) LOCATION: 12
    ( D ) OTHER INFORMATION: /note= "Xaa at position 12 is His or Ala"

( i x ) FEATURE:
    ( A ) NAME/KEY: Modified-site
    ( B ) LOCATION: 15
    ( D ) OTHER INFORMATION: /note= "Xaa at position 15 is Gln or Asn"

( i x ) FEATURE:
    ( A ) NAME/KEY: Modified-site
    ( B ) LOCATION: 16
    ( D ) OTHER INFORMATION: /note= "Xaa at position 16 is Pro or Gly"

( i x ) FEATURE:
    ( A ) NAME/KEY: Modified-site
    ( B ) LOCATION: 18
    ( D ) OTHER INFORMATION: /note= "Xaa at position 18 is Leu, Arg, Asn, or Ala"

( i x ) FEATURE:
    ( A ) NAME/KEY: Modified-site
    ( B ) LOCATION: 20
    ( D ) OTHER INFORMATION: /note= "Xaa at position 20 is Leu, Val, Ser, Ala, Arg, Gln, Glu, Ile, Phe, Thr, or Met"

( i x ) FEATURE:
    ( A ) NAME/KEY: Modified-site
    ( B ) LOCATION: 21
    ( D ) OTHER INFORMATION: /note= "Xaa at position 21 is Leu, Ala, Asn, or Pro"

( i x ) FEATURE:
    ( A ) NAME/KEY: Modified-site
    ( B ) LOCATION: 24
    ( D ) OTHER INFORMATION: /note= "Xaa at position 24 is Asn or Ala"

( i x ) FEATURE:

(A) NAME/KEY: Modified-site
(B) LOCATION: 28
(D) OTHER INFORMATION: /note= "Xaa at position 28 is Gly,
Asp, Ser, Ala, Asn, Ile, Leu, Met, Tyr, or Arg"

(ix) FEATURE:
(A) NAME/KEY: Modified-site
(B) LOCATION: 31
(D) OTHER INFORMATION: /note= "Xaa at position 31 is Gln,
Val, Met, Leu, Ala, Asn, Glu, or Lys"

(ix) FEATURE:
(A) NAME/KEY: Modified-site
(B) LOCATION: 32
(D) OTHER INFORMATION: /note= "Xaa at position 32 is Asp,
Phe, Ser, Ala, Gln, Glu, His, Val, or Thr"

(ix) FEATURE:
(A) NAME/KEY: Modified-site
(B) LOCATION: 36
(D) OTHER INFORMATION: /note= "Xaa at position 36 is Glu,
Asn, Ser, or Asp"

(ix) FEATURE:
(A) NAME/KEY: Modified-site
(B) LOCATION: 37
(D) OTHER INFORMATION: /note= "Xaa at position 37 is Asn,
Arg, Pro, Thr, or His"

(ix) FEATURE:
(A) NAME/KEY: Modified-site
(B) LOCATION: 41
(D) OTHER INFORMATION: /note= "Xaa at position 41 is Arg,
Leu, or Gly"

(ix) FEATURE:
(A) NAME/KEY: Modified-site
(B) LOCATION: 42
(D) OTHER INFORMATION: /note= "Xaa at position 42 is Pro,
Gly, Ser, Ala, Asn, Val, Leu, or Gln"

(ix) FEATURE:
(A) NAME/KEY: Modified-site
(B) LOCATION: 48
(D) OTHER INFORMATION: /note= "Xaa at position 48 is Asn,
Pro, or Thr"

(ix) FEATURE:
(A) NAME/KEY: Modified-site
(B) LOCATION: 50
(D) OTHER INFORMATION: /note= "Xaa at position 50 is Ala
or Asn"

(ix) FEATURE:
(A) NAME/KEY: Modified-site
(B) LOCATION: 51
(D) OTHER INFORMATION: /note= "Xaa at position 51 is Val
or Thr"

(ix) FEATURE:
(A) NAME/KEY: Modified-site
(B) LOCATION: 53
(D) OTHER INFORMATION: /note= "Xaa at position 53 is Ser
or Phe"

(ix) FEATURE:
(A) NAME/KEY: Modified-site
(B) LOCATION: 54
(D) OTHER INFORMATION: /note= "Xaa at position 54 is Leu
or Phe"

(ix) FEATURE:
(A) NAME/KEY: Modified-site
(B) LOCATION: 55
(D) OTHER INFORMATION: /note= "Xaa at position 55 is Gln,
Ala, Glu, or Arg"

(ix) FEATURE:
(A) NAME/KEY: Modified-site
(B) LOCATION: 62

(D) OTHER INFORMATION: /note= "Xaa at position 62 is Ser, Val, Asn, Pro, or Gly"

(ix) FEATURE:
 (A) NAME/KEY: Modified-site
 (B) LOCATION: 63
 (D) OTHER INFORMATION: /note= "Xaa at position 63 is Ile or Leu"

(ix) FEATURE:
 (A) NAME/KEY: Modified-site
 (B) LOCATION: 65
 (D) OTHER INFORMATION: /note= "Xaa at position 65 is Lys, Asn, Met, Arg, Ile, or Gly"

(ix) FEATURE:
 (A) NAME/KEY: Modified-site
 (B) LOCATION: 66
 (D) OTHER INFORMATION: /note= "Xaa at position 66 is Asn, Gly, Glu, or Arg"

(ix) FEATURE:
 (A) NAME/KEY: Modified-site
 (B) LOCATION: 68
 (D) OTHER INFORMATION: /note= "Xaa at position 68 is Leu, Gln, Trp, Arg, Asp, Asn, Glu, His, Met, Phe, Ser, Thr, Tyr, or Val"

(ix) FEATURE:
 (A) NAME/KEY: Modified-site
 (B) LOCATION: 73
 (D) OTHER INFORMATION: /note= "Xaa at position 73 is Leu or Ser"

(ix) FEATURE:
 (A) NAME/KEY: Modified-site
 (B) LOCATION: 74
 (D) OTHER INFORMATION: /note= "Xaa at position 74 is Ala or Trp"

(ix) FEATURE:
 (A) NAME/KEY: Modified-site
 (B) LOCATION: 77
 (D) OTHER INFORMATION: /note= "Xaa at position 77 is Ala or Pro"

(ix) FEATURE:
 (A) NAME/KEY: Modified-site
 (B) LOCATION: 79
 (D) OTHER INFORMATION: /note= "Xaa at position 79 is Thr, Asp, or Ala"

(ix) FEATURE:
 (A) NAME/KEY: Modified-site
 (B) LOCATION: 81
 (D) OTHER INFORMATION: /note= "Xaa at position 81 is His, Pro, Arg, Val, Gly, Asn, Ser, or Thr"

(ix) FEATURE:
 (A) NAME/KEY: Modified-site
 (B) LOCATION: 84
 (D) OTHER INFORMATION: /note= "Xaa at position 84 is His, Ile, Asn, Leu, Ala, Thr, Arg, Gln, Glu, Lys, Met, Ser, Tyr, Val, or Leu"

(ix) FEATURE:
 (A) NAME/KEY: Modified-site
 (B) LOCATION: 85
 (D) OTHER INFORMATION: /note= "Xaa at position 85 is Ile or Leu"

(ix) FEATURE:
 (A) NAME/KEY: Modified-site
 (B) LOCATION: 86
 (D) OTHER INFORMATION: /note= "Xaa at position 86 is Lys or Arg"

(ix) FEATURE:
 (A) NAME/KEY: Modified-site
 (B) LOCATION: 87

(D) OTHER INFORMATION: /note= "Xaa at position 87 is Asp,
Pro, Met, Lys, His, Pro, Asn, Ile, Leu, or Tyr"

(ix) FEATURE:
 (A) NAME/KEY: Modified-site
 (B) LOCATION: 91
 (D) OTHER INFORMATION: /note= "Xaa at position 91 is Asn,
Pro, Ser, Ile, or Asp"

(ix) FEATURE:
 (A) NAME/KEY: Modified-site
 (B) LOCATION: 94
 (D) OTHER INFORMATION: /note="Xaa at position 94 is Arg,
Ala, or Ser"

(ix) FEATURE:
 (A) NAME/KEY: Modified-site
 (B) LOCATION: 95
 (D) OTHER INFORMATION: /note= "Xaa at position 95 is Arg,
Thr, Glu, Leu, or Ser"

(ix) FEATURE:
 (A) NAME/KEY: Modified-site
 (B) LOCATION: 98
 (D) OTHER INFORMATION: /note= "Xaa at position 98 is Thr
or Gln"

(ix) FEATURE:
 (A) NAME/KEY: Modified-site
 (B) LOCATION: 102
 (D) OTHER INFORMATION: /note= "Xaa at position 102 is Lys,
Val, Trp, or Ile"

(ix) FEATURE:
 (A) NAME/KEY: Modified-site
 (B) LOCATION: 103
 (D) OTHER INFORMATION: /note= "Xaa at position 103 is Thr,
Ala, His, Phe, Tyr, or Ser"

(ix) FEATURE:
 (A) NAME/KEY: Modified-site
 (B) LOCATION: 106
 (D) OTHER INFORMATION: /note= "Xaa at position 106 is Asn,
Pro, Leu, His, Val, or Gln"

(ix) FEATURE:
 (A) NAME/KEY: Modified-site
 (B) LOCATION: 107
 (D) OTHER INFORMATION: /note= "Xaa at position 107 is Ala,
Ser, Ile, Pro, or Asp"

(ix) FEATURE:
 (A) NAME/KEY: Modified-site
 (B) LOCATION: 108
 (D) OTHER INFORMATION: /note= "Xaa at position 108 is Gln,
Met, Trp, Phe, Pro, His, Ile, or Tyr"

(ix) FEATURE:
 (A) NAME/KEY: Modified-site
 (B) LOCATION: 109
 (D) OTHER INFORMATION: /note= "Xaa at position 109 is Ala,
Met, Glu, Ser, or Leu"

(xi) SEQUENCE DESCRIPTION: SEQ ID NO:6:

```
Asn Cys Xaa Xaa Met Ile Asp Glu Xaa Ile Xaa Xaa Leu Lys Xaa Xaa
1               5                   10                  15

Pro Xaa Pro Xaa Xaa Asp Phe Xaa Asn Leu Asn Xaa Glu Asp Xaa Xaa
            20                  25                  30

Ile Leu Met Xaa Xaa Asn Leu Arg Xaa Xaa Asn Leu Glu Ala Phe Xaa
            35                  40                  45

Arg Xaa Xaa Lys Xaa Xaa Xaa Asn Ala Ser Ala Ile Glu Xaa Xaa Leu
    50                  55                  60

Xaa Xaa Leu Xaa Pro Cys Leu Pro Xaa Xaa Thr Ala Xaa Pro Xaa Arg
65              70                  75                      80
```

```
Xaa Pro Ile Xaa Xaa Xaa Xaa Gly Asp Trp Xaa Glu Phe Xaa Xaa Lys
            85              90                      95
Leu Xaa Phe Tyr Leu Xaa Xaa Leu Glu Xaa Xaa Xaa Xaa Gln Gln
        100             105                 110
```

( 2 ) INFORMATION FOR SEQ ID NO:7:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Met- may or may not precede the amino acid in position 1"

( i x ) FEATURE:
        ( A ) NAME/KEY: Modified-site
        ( B ) LOCATION: 18
        ( D ) OTHER INFORMATION: /note= "Xaa at position 18 is Asn or Ile"

( i x ) FEATURE:
        ( A ) NAME/KEY: Modified-site
        ( B ) LOCATION: 19
        ( D ) OTHER INFORMATION: /note= "Xaa at position 19 is Met, Ala, or Ile"

( i x ) FEATURE:
        ( A ) NAME/KEY: Modified-site
        ( B ) LOCATION: 20
        ( D ) OTHER INFORMATION: /note= "Xaa at position 20 is Ile, Pro, or Leu"

( i x ) FEATURE:
        ( A ) NAME/KEY: Modified-site
        ( B ) LOCATION: 23
        ( D ) OTHER INFORMATION: /note= "Xaa at position 23 is Ile, Ala, or Leu"

( i x ) FEATURE:
        ( A ) NAME/KEY: Modified-site
        ( B ) LOCATION: 25
        ( D ) OTHER INFORMATION: /note= "Xaa at position 25 is Thr or His"

( i x ) FEATURE:
        ( A ) NAME/KEY: Modified-site
        ( B ) LOCATION: 29
        ( D ) OTHER INFORMATION: /note= "Xaa at position 29 is Gln, Arg, Val, or Ile"

( i x ) FEATURE:
        ( A ) NAME/KEY: Modified-site
        ( B ) LOCATION: 32
        ( D ) OTHER INFORMATION: /note= "Xaa at position 32 is Leu, Ala, Asn, or Arg"

( i x ) FEATURE:
        ( A ) NAME/KEY: Modified-site
        ( B ) LOCATION: 34
        ( D ) OTHER INFORMATION: /note= "Xaa at position 34 is Leu or Ser"

( i x ) FEATURE:
        ( A ) NAME/KEY: Modified-site
        ( B ) LOCATION: 37
        ( D ) OTHER INFORMATION: /note= "Xaa at position 37 is Phe, Pro, or Ser"

( i x ) FEATURE:
        ( A ) NAME/KEY: Modified-site
        ( B ) LOCATION:; 38
        ( D ) OTHER INFORMATION: /note= "Xaa at position 38 is Asn or Ala"

( i x ) FEATURE:
    ( A ) NAME/KEY: Modified-site
    ( B ) LOCATION: 42
    ( D ) OTHER INFORMATION: /note= "Xaa at position 42 is Gly,
        Ala, Ser, Asp, or Asn"

( i x ) FEATURE:
    ( A ) NAME/KEY: Modified-site
    ( B ) LOCATION: 45
    ( D ) OTHER INFORMATION: /note= "Xaa at position 45 is Gln,
        Val, or Met"

( i x ) FEATURE:
    ( A ) NAME/KEY: Modified-site
    ( B ) LOCATION: 46
    ( D ) OTHER INFORMATION: /note= "Xaa at position 46 is Asp
        or Ser"

( i x ) FEATURE:
    ( A ) NAME/KEY: Modified-site
    ( B ) LOCATION: 49
    ( D ) OTHER INFORMATION: /note= "Xaa at position 49 is Met,
        Ile, Leu, or Asp"

( i x ) FEATURE:
    ( A ) NAME/KEY: Modified-site
    ( B ) LOCATION: 50
    ( D ) OTHER INFORMATION: /note= "Xaa at position 50 is Glu
        or Asp"

( i x ) FEATURE:
    ( A ) NAME/KEY: Modified-site
    ( B ) LOCATION: 51
    ( D ) OTHER INFORMATION: /note= "Xaa at position 51 is Asn,
        Arg, or Ser"

( i x ) FEATURE:
    ( A ) NAME/KEY: Modified-site
    ( B ) LOCATION: 55
    ( D ) OTHER INFORMATION: /note= "Xaa at position 55 is Arg,
        Leu, or Thr"

( i x ) FEATURE:
    ( A ) NAME/KEY: Modified-site
    ( B ) LOCATION: 56
    ( D ) OTHER INFORMATION: /note= "Xaa at position 56 is Pro
        or Ser"

( i x ) FEATURE:
    ( A ) NAME/KEY: Modified-site
    ( B ) LOCATION: 59
    ( D ) OTHER INFORMATION: /note= "Xaa at position 59 is Glu
        or Leu"

( i x ) FEATURE:
    ( A ) NAME/KEY: Modified-site
    ( B ) LOCATION: 60
    ( D ) OTHER INFORMATION: /note= "Xaa at position 60 is Ala
        or Ser"

( i x ) FEATURE:
    ( A ) NAME/KEY: Modified-site
    ( B ) LOCATION: 62
    ( D ) OTHER INFORMATION: /note= "Xaa at position 62 is Asn
        Val, or Pro"

( i x ) FEATURE:
    ( A ) NAME/KEY: Modified-site
    ( B ) LOCATION: 63
    ( D ) OTHER INFORMATION: /note= "Xaa at position 63 is Arg
        or His"

( i x ) FEATURE:
    ( A ) NAME/KEY: Modified-site
    ( B ) LOCATION: 65
    ( D ) OTHER INFORMATION: /note= "Xaa at position 65 is Val
        or Ser"

( i x ) FEATURE:
- ( A ) NAME/KEY: Modified-site
- ( B ) LOCATION: 67
- ( D ) OTHER INFORMATION: /note= "Xaa at position 67 is Ser, Asn, His, or Gln"

( i x ) FEATURE:
- ( A ) NAME/KEY: Modified-site
- ( B ) LOCATION: 69
- ( D ) OTHER INFORMATION: /note= "Xaa at position 69 is Gln or Glu"

( i x ) FEATURE:
- ( A ) NAME/KEY: Modified-site
- ( B ) LOCATION: 73
- ( D ) OTHER INFORMATION: /note= "Xaa at position 73 is Ala or Gly"

( i x ) FEATURE:
- ( A ) NAME/KEY: Modified-site
- ( B ) LOCATION: 76
- ( D ) OTHER INFORMATION: /note= "Xaa at position 76 is Ser, Ala, or Pro"

( i x ) FEATURE:
- ( A ) NAME/KEY: Modified-site
- ( B ) LOCATION: 79
- ( D ) OTHER INFORMATION: /note= "Xaa at position 79 is Lys, Arg, or Ser"

( i x ) FEATURE:
- ( A ) NAME/KEY: Modified-site
- ( B ) LOCATION: 82
- ( D ) OTHER INFORMATION: /note= "Xaa at position 82 is Leu, Glu, Val, or Trp"

( i x ) FEATURE:
- ( A ) NAME/KEY: Modified-site
- ( B ) LOCATION: 85
- ( D ) OTHER INFORMATION: /note= "Xaa at position 85 is Leu or Val"

( i x ) FEATURE:
- ( A ) NAME/KEY: Modified-site
- ( B ) LOCATION: 87
- ( D ) OTHER INFORMATION: /note= "Xaa at position 87 is Leu, Ser, or Tyr"

( i x ) FEATURE:
- ( A ) NAME/KEY: Modified-site
- ( B ) LOCATION: 88
- ( D ) OTHER INFORMATION: /note= "Xaa at position 88 is Ala or Trp"

( i x ) FEATURE:
- ( A ) NAME/KEY: Modified-site
- ( B ) LOCATION: 91
- ( D ) OTHER INFORMATION: /note= "Xaa at position 91 is Ala or Pro"

( i x ) FEATURE:
- ( A ) NAME/KEY: Modified-site
- ( B ) LOCATION: 93
- ( D ) OTHER INFORMATION: /note= "Xaa at position 93 is Pro or Ser"

( i x ) FEATURE:
- ( A ) NAME/KEY: Modified-site
- ( B ) LOCATION: 95
- ( D ) OTHER INFORMATION: /note= "Xaa at position 95 is His or Thr"

( i x ) FEATURE:
- ( A ) NAME/KEY: Modified-site
- ( B ) LOCATION: 98
- ( D ) OTHER INFORMATION: /note= "Xaa at position 98 is His, Ile, or Thr"

( i x ) FEATURE:
- ( A ) NAME/KEY: Modified-site (B) LOCATION: 100
(D) OTHER INFORMATION: /note= "Xaa at position 100 is Lys or Arg"

(ix) FEATURE:
(A) NAME/KEY: Modified-site
(B) LOCATION: 101
(D) OTHER INFORMATION: /note= "Xaa at position 101 is Asp, Ala, or Met"

(ix) FEATURE:
(A) NAME/KEY: Modified-site
(B) LOCATION: 105
(D) OTHER INFORMATION: /note= "Xaa at position 105 is Asn or Glu"

(ix) FEATURE:
(A) NAME/KEY: Modified-site
(B) LOCATION: 109
(D) OTHER INFORMATION: /note= "Xaa at position 109 is Arg, Glu, or Leu"

(ix) FEATURE:
(A) NAME/KEY: Modified-site
(B) LOCATION: 112
(D) OTHER INFORMATION: /note= "Xaa at position 112 is Thr or Gln"

(ix) FEATURE:
(A) NAME/KEY: Modified-site
(B) LOCATION: 116
(D) OTHER INFORMATION: /note= "Xaa at position 116 is Lys, Val, Trp, or Ser"

(ix) FEATURE:
(A) NAME/KEY: Modified-site
(B) LOCATION: 117
(D) OTHER INFORMATION: /note= "Xaa at position 117 is Thr or Ser"

(ix) FEATURE:
(A) NAME/KEY: Modified-site
(B) LOCATION: 120
(D) OTHER INFORMATION: /note= "Xaa at position 120 is Asn, Gln, or His"

(ix) FEATURE:
(A) NAME/KEY: Modified-site
(B) LOCATION: 123
(D) OTHER INFORMATION: /note= "Xaa at position 123 is Ala or Glu"

(xi) SEQUENCE DESCRIPTION: SEQ ID NO:7:

```
Ala Pro Met Thr Gln Thr Thr Ser Leu Lys Thr Ser Trp Val Asn Cys
1               5                   10                  15

Ser Xaa Xaa Xaa Asp Glu Xaa Ile Xaa His Leu Lys Xaa Pro Pro Xaa
            20                  25                  30

Pro Xaa Leu Asp Xaa Xaa Asn Leu Asn Xaa Glu Asp Xaa Xaa Ile Leu
        35                  40                  45

Xaa Xaa Xaa Asn Leu Arg Xaa Xaa Asn Leu Xaa Xaa Phe Xaa Xaa Ala
    50                  55                      60

Xaa Lys Xaa Leu Xaa Asn Ala Ser Xaa Ile Glu Xaa Ile Leu Xaa Asn
65                      70              75                  80

Leu Xaa Pro Cys Xaa Pro Xaa Xaa Thr Ala Xaa Pro Xaa Arg Xaa Pro
                85                  90                  95

Ile Xaa Ile Xaa Xaa Gly Asp Trp Xaa Glu Phe Arg Xaa Lys Leu Xaa
            100                 105                 110

Phe Tyr Leu Xaa Xaa Leu Glu Xaa Ala Gln Xaa Gln Gln Thr Thr Leu
        115                 120                 125

Ser Leu Ala Ile Phe
    130
```

( 2 ) INFORMATION FOR SEQ ID NO:8:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Met- or Met-Ala may or may
            not precede the amino acid in position 1"

( i x ) FEATURE:
        ( A ) NAME/KEY: Modified-site
        ( B ) LOCATION: 4
        ( D ) OTHER INFORMATION: /note= "Xaa at position 4 is Asn or
            Ile"

( i x ) FEATURE:
        ( A ) NAME/KEY: Modified-site
        ( B ) LOCATION: 5
        ( D ) OTHER INFORMATION: /note= "Xaa at position 5 is Met,
            Ala, or Ile"

( i x ) FEATURE:
        ( A ) NAME/KEY: Modified-site
        ( B ) LOCATION: 6
        ( D ) OTHER INFORMATION: /note= "Xaa at position 6 is Ile,
            Pro, or Leu"

( i x ) FEATURE:
        ( A ) NAME/KEY: Modified-site
        ( B ) LOCATION: 9
        ( D ) OTHER INFORMATION: /note= "Xaa at position 9 is Ile,
            Ala, or Leu"

( i x ) FEATURE:
        ( A ) NAME/KEY: Modified-site
        ( B ) LOCATION: 11
        ( D ) OTHER INFORMATION: /note= "Xaa at position 11 is Thr
            or His"

( i x ) FEATURE:
        ( A ) NAME/KEY: Modified-site
        ( B ) LOCATION: 15
        ( D ) OTHER INFORMATION: /note= "Xaa at position 15 is Gln,
            Arg, Val, or Ile"

( i x ) FEATURE:
        ( A ) NAME/KEY: Modified-site
        ( B ) LOCATION: 18
        ( D ) OTHER INFORMATION: /note= "Xaa at position 18 is Leu,
            Ala, Asn, or Arg"

( i x ) FEATURE:
        ( A ) NAME/KEY: Modified-site
        ( B ) LOCATION: 20
        ( D ) OTHER INFORMATION: /note= "Xaa at position 20 is Leu
            or Ser"

( i x ) FEATURE:
        ( A ) NAME/KEY: Modified-site
        ( B ) LOCATION: 23
        ( D ) OTHER INFORMATION: /note= "Xaa at position 23 is Phe,
            Pro, or Ser"

( i x ) FEATURE:
        ( A ) NAME/KEY: Modified-site
        ( B ) LOCATION: 24
        ( D ) OTHER INFORMATION: /note= "Xaa at position 24 is Asn
            or Ala"

( i x ) FEATURE:
        ( A ) NAME/KEY: Modified-site
        ( B ) LOCATION: 28

( D ) OTHER INFORMATION: /note= "Xaa at position 28 is Gly,
Ala, Ser, Asp, or Asn"

( i x ) FEATURE:
    ( A ) NAME/KEY: Modified-site
    ( B ) LOCATION: 31
    ( D ) OTHER INFORMATION: /note= "Xaa at position 31 is Gln,
Val, or Met"

( i x ) FEATURE:
    ( A ) NAME/KEY: Modified-site
    ( B ) LOCATION: 32
    ( D ) OTHER INFORMATION: /note= "Xaa at position 32 is Asp
or Ser"

( i x ) FEATURE:
    ( A ) NAME/KEY: Modified-site
    ( B ) LOCATION: 35
    ( D ) OTHER INFORMATION: /note= "Xaa at position 35 is Met,
Ile, or Asp"

( i x ) FEATURE:
    ( A ) NAME/KEY: Modified-site
    ( B ) LOCATION: 36
    ( D ) OTHER INFORMATION: /note= "Xaa at position 36 is Glu
or Asp"

( i x ) FEATURE:
    ( A ) NAME/KEY: Modified-site
    ( B ) LOCATION: 37
    ( D ) OTHER INFORMATION: /note= "Xaa at position 37 is Asn,
Arg, or Ser"

( i x ) FEATURE:
    ( A ) NAME/KEY: Modified-site
    ( B ) LOCATION: 41
    ( D ) OTHER INFORMATION: /note= "Xaa at position 41 is Arg,
Leu, or Thr"

( i x ) FEATURE:
    ( A ) NAME/KEY: Modified-site
    ( B ) LOCATION: 42
    ( D ) OTHER INFORMATION: /note= "Xaa at position 42 is Pro
or Ser"

( i x ) FEATURE:
    ( A ) NAME/KEY: Modified-site
    ( B ) LOCATION: 45
    ( D ) OTHER INFORMATION: /note= "Xaa at position 45 is Glu
or Leu"

( i x ) FEATURE:
    ( A ) NAME/KEY: Modified-site
    ( B ) LOCATION: 46
    ( D ) OTHER INFORMATION: /note= "Xaa at position 46 is Ala
or Ser"

( i x ) FEATURE:
    ( A ) NAME/KEY: Modified-site
    ( B ) LOCATION: 48
    ( D ) OTHER INFORMATION: /note= "Xaa at position 48 is Asn,
Val, or Pro"

( i x ) FEATURE:
    ( A ) NAME/KEY: Modified-site
    ( B ) LOCATION: 49
    ( D ) OTHER INFORMATION: /note= "Xaa at position 49 is Arg
or His"

( i x ) FEATURE:
    ( A ) NAME/KEY: Modified-site
    ( B ) LOCATION: 51
    ( D ) OTHER INFORMATION: /note= "Xaa at position 51 is Val
or Ser"

( i x ) FEATURE:
    ( A ) NAME/KEY: Modified-site
    ( B ) LOCATION: 53
    ( D ) OTHER INFORMATION: /note= "Xaa at position 53 is Ser,
Asn, His, or Gln"

( i x ) FEATURE:
    ( A ) NAME/KEY: Modified-site
    ( B ) LOCATION: 55
    ( D ) OTHER INFORMATION: /note= "Xaa at position 55 is Gln
        or Glu"

( i x ) FEATURE:
    ( A ) NAME/KEY: Modified-site
    ( B ) LOCATION: 59
    ( D ) OTHER INFORMATION: /note= "Xaa at position 59 is Ala
        or Gly"

( i x ) FEATURE:
    ( A ) NAME/KEY: Modified-site
    ( B ) LOCATION: 62
    ( D ) OTHER INFORMATION: /note= "Xaa at position 62 is Ser,
        Ala, or Pro"

( i x ) FEATURE:
    ( A ) NAME/KEY: Modified-site
    ( B ) LOCATION: 65
    ( D ) OTHER INFORMATION: /note= "Xaa at position 65 is Lys,
        Arg, or Ser"

( i x ) FEATURE:
    ( A ) NAME/KEY: Modified-site
    ( B ) LOCATION: 67
    ( D ) OTHER INFORMATION: /note= "Xaa at position 67 is Leu,
        Glu, or Val"

( i x ) FEATURE:
    ( A ) NAME/KEY: Modified-site
    ( B ) LOCATION: 68
    ( D ) OTHER INFORMATION: /note= "Xaa at position 68 is Leu,
        Glu, Val, or Trp"

( i x ) FEATURE:
    ( A ) NAME/KEY: Modified-site
    ( B ) LOCATION: 71
    ( D ) OTHER INFORMATION: /note= "Xaa at position 71 is Leu
        or Val"

( i x ) FEATURE:
    ( A ) NAME/KEY: Modified-site
    ( B ) LOCATION: 73
    ( D ) OTHER INFORMATION: /note= "Xaa at position 73 is Leu,
        Ser, or Tyr"

( i x ) FEATURE:
    ( A ) NAME/KEY: Modified-site
    ( B ) LOCATION: 74
    ( D ) OTHER INFORMATION: /note= "Xaa at position 74 is Ala
        or Trp"

( i x ) FEATURE:
    ( A ) NAME/KEY: Modified-site
    ( B ) LOCATION: 77
    ( D ) OTHER INFORMATION: /note= "Xaa at position 77 is Ala
        or Pro"

( i x ) FEATURE:
    ( A ) NAME/KEY: Modified-site
    ( B ) LOCATION: 79
    ( D ) OTHER INFORMATION: /note= "Xaa at position 79 is Pro
        or Ser"

( i x ) FEATURE:
    ( A ) NAME/KEY: Modified-site
    ( B ) LOCATION: 81
    ( D ) OTHER INFORMATION: /note= "Xaa at position 81 is His
        or Thr"

( i x ) FEATURE:
    ( A ) NAME/KEY: Modified-site
    ( B ) LOCATION: 84
    ( D ) OTHER INFORMATION: /note= "Xaa at position 84 is His,
        Ile, or Thr"

( i x ) FEATURE:

(A) NAME/KEY: Modified-site
(B) LOCATION: 86
(D) OTHER INFORMATION: /note= "Xaa at position 86 is Lys or Arg"

(ix) FEATURE:
(A) NAME/KEY: Modified-site
(B) LOCATION: 87
(D) OTHER INFORMATION: /note= "Xaa at position 87 is Asp, Ala, or Met"

(ix) FEATURE:
(A) NAME/KEY: Modified-site
(B) LOCATION: 91
(D) OTHER INFORMATION: /note= "Xaa at position 91 is Asn or Glu"

(ix) FEATURE:
(A) NAME/KEY: Modified-site
(B) LOCATION: 95
(D) OTHER INFORMATION: /note= "Xaa at position 95 is Arg, Glu, or Leu"

(ix) FEATURE:
(A) NAME/KEY: Modified-site
(B) LOCATION: 98
(D) OTHER INFORMATION: /note= "Xaa at position 98 is Thr or Gln"

(ix) FEATURE:
(A) NAME/KEY: Modified-site
(B) LOCATION: 102
(D) OTHER INFORMATION: /note= "Xaa at position 102 is Lys, Val, Trp, or Ser"

(ix) FEATURE:
(A) NAME/KEY: Modified-site
(B) LOCATION: 103
(D) OTHER INFORMATION: /note= "Xaa at position 103 is Thr or Ser"

(ix) FEATURE:
(A) NAME/KEY: Modified-site
(B) LOCATION: 106
(D) OTHER INFORMATION: /note= "Xaa at position 106 is Asn, Gln, or His"

(ix) FEATURE:
(A) NAME/KEY: Modified-site
(B) LOCATION: 109
(D) OTHER INFORMATION: /note= "Xaa at position 109 is Ala or Glu"

(xi) SEQUENCE DESCRIPTION: SEQ ID NO:8:

```
Asn Cys Ser Xaa Xaa Xaa Asp Glu Xaa Ile Xaa His Leu Lys Xaa Pro
 1               5                   10                  15
Pro Xaa Pro Xaa Leu Asp Xaa Xaa Asn Leu Asn Xaa Glu Asp Xaa Xaa
             20                  25                  30
Ile Leu Xaa Xaa Xaa Asn Leu Arg Xaa Xaa Asn Leu Xaa Xaa Phe Xaa
         35                  40                  45
Xaa Ala Xaa Lys Xaa Leu Xaa Asn Ala Ser Xaa Ile Glu Xaa Ile Leu
     50                  55                  60
Xaa Asn Xaa Xaa Pro Cys Xaa Pro Xaa Xaa Thr Ala Xaa Pro Xaa Arg
 65                  70                  75                  80
Xaa Pro Ile Xaa Ile Xaa Xaa Gly Asp Trp Xaa Glu Phe Arg Xaa Lys
                 85                  90                  95
Leu Xaa Phe Tyr Leu Xaa Xaa Leu Glu Xaa Ala Gln Xaa Gln Gln
             100                 105                 110
```

(2) INFORMATION FOR SEQ ID NO:9:

(i) SEQUENCE CHARACTERISTICS:

(A) LENGTH: 134 amino acids
(B) TYPE: amino acid
(D) TOPOLOGY: linear (ii) MOLECULE TYPE: peptide (xi) SEQUENCE DESCRIPTION: SEQ ID NO:9:

| Met | Ala | Pro | Met | Thr | Gln | Thr | Thr | Ser | Leu | Lys | Thr | Ser | Trp | Val | Asn |
|---|---|---|---|---|---|---|---|---|---|---|---|---|---|---|---|
| 1 | | | | 5 | | | | | 10 | | | | | 15 | |
| Cys | Ser | Asn | Met | Ile | Asp | Glu | Ile | Ile | Thr | His | Leu | Lys | Gln | Pro | Pro |
| | | | 20 | | | | | 25 | | | | | 30 | | |
| Leu | Pro | Leu | Leu | Asp | Phe | Asn | Asn | Leu | Asn | Gly | Glu | Asp | Gln | Asp | Ile |
| | | 35 | | | | | 40 | | | | | 45 | | | |
| Leu | Met | Glu | Asn | Asn | Leu | Arg | Arg | Pro | Asn | Leu | Glu | Ala | Phe | Asn | Arg |
| | 50 | | | | | 55 | | | | | 60 | | | | |
| Ala | Val | Lys | Ser | Leu | Gln | Asn | Ala | Ser | Ala | Ile | Glu | Ser | Ile | Leu | Lys |
| 65 | | | | | 70 | | | | | 75 | | | | | 80 |
| Asn | Leu | Leu | Pro | Cys | Leu | Pro | Leu | Ala | Thr | Ala | Ala | Pro | Thr | Arg | His |
| | | | | 85 | | | | | 90 | | | | | 95 | |
| Pro | Ile | His | Ile | Lys | Asp | Gly | Asp | Trp | Asn | Glu | Phe | Arg | Arg | Lys | Leu |
| | | | 100 | | | | | 105 | | | | | 110 | | |
| Thr | Phe | Tyr | Leu | Lys | Thr | Leu | Glu | Asn | Ala | Gln | Ala | Gln | Gln | Thr | Thr |
| | | 115 | | | | | 120 | | | | | 125 | | | |
| Leu | Ser | Leu | Ala | Ile | Phe | | | | | | | | | | |
| | | 130 | | | | | | | | | | | | | |

(2) INFORMATION FOR SEQ ID NO:10:

(i) SEQUENCE CHARACTERISTICS:
(A) LENGTH: 408 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:10:

| ATGGCTCCAA | TGACTCAGAC | TACTTCTCTT | AAGACTTCTT | GGGTTAACTG | CTCTAACATG | 60 |
| ATCGATGAAA | TTATAACACA | CTTAAAGCAG | CCACCTTTGC | CTTTGCTGGA | CTTCAACAAC | 120 |
| CTCAATGGGG | AAGACCAAGA | CATTCTGATG | GAAAATAACC | TTCGAAGGCC | AAACCTGGAG | 180 |
| GCATTCAACA | GGGCTGTCAA | GAGTTTACAG | AATGCATCAG | CAATTGAGAG | CATTCTTAAA | 240 |
| AATCTCCTGC | CATGTCTGCC | CCTGGCCACG | GCCGCACCCA | CGCGACATCC | AATCCATATC | 300 |
| AAGGACGGTG | ACTGGAATGA | ATTCCGTCGT | AAACTGACCT | TCTATCTGAA | AACCTTGGAG | 360 |
| AACGCGCAGG | CTCAACAGAC | CACTCTGTCG | CTAGCGATCT | TTTAATAA | | 408 |